United States Patent
Congreve et al.

(10) Patent No.: US 9,907,805 B2
(45) Date of Patent: Mar. 6, 2018

(54) MUSCARINIC M1 RECEPTOR AGONISTS

(71) Applicant: Heptares Therapeutics Limited, Welwyn Garden City (GB)

(72) Inventors: Miles Stuart Congreve, Welwyn Garden City (GB); Giles Albert Brown, Welwyn Garden City (GB); Julie Elaine Cansfield, Welwyn Garden City (GB); Benjamin Gerald Tehan, Welwyn Garden City (GB)

(73) Assignee: Heptares Therapeutics Limited, Welwyn Garden (GB)

(*) Notice: Subject to any disclaimer, the term of this patent is extended or adjusted under 35 U.S.C. 154(b) by 0 days.

(21) Appl. No.: 15/436,224

(22) Filed: Feb. 17, 2017

(65) Prior Publication Data

US 2017/0157139 A1 Jun. 8, 2017

Related U.S. Application Data

(60) Division of application No. 14/941,328, filed on Nov. 13, 2015, now Pat. No. 9,573,929, which is a continuation of application No. 14/358,984, filed as application No. PCT/GB2012/052857 on Nov. 16, 2012, now Pat. No. 9,187,451.

(60) Provisional application No. 61/632,813, filed on Nov. 18, 2011.

(51) Int. Cl.
*A61K 31/55* (2006.01)
*A61K 31/4545* (2006.01)

(52) U.S. Cl.
CPC .......... *A61K 31/55* (2013.01); *A61K 31/4545* (2013.01)

(58) Field of Classification Search
CPC ..................................................... A61K 31/55
USPC ................................................... 514/217.04
See application file for complete search history.

(56) References Cited

U.S. PATENT DOCUMENTS

| 5,854,245 A | 12/1998 | Duggan et al. |
| 9,187,451 B2 | 11/2015 | Congreve et al. |
| 2006/0194844 A1 | 8/2006 | Sugasawa et al. |
| 2008/0015179 A1 | 1/2008 | Makings et al. |
| 2009/0076078 A1 | 3/2009 | Cheng et al. |

FOREIGN PATENT DOCUMENTS

| EP | 1647553 A1 | 4/2006 |
| WO | 9932479 A1 | 7/1999 |
| WO | 2007/076070 A2 | 7/2007 |
| WO | 2009/034380 A1 | 3/2009 |

OTHER PUBLICATIONS

Geyer et al, Handbook of Experimental Pharmacology 213, Springer-Verlag Berlin Heidelberg 2012, p. 239.*
Kuduk, Expert Opin. Ther. Patents (2012) 22(12):1385-1398.*
Lankin et al. J. Am. Chem. Soc. 1993,115, 3356-3357.
Venkatesh et al., J. Pharm. Sci. 89, 145-54 (2000).
Snyder et al. J. Am. Chem. Soc. 2000, 122, 544-545.
International Search Report for PCT/GB2012/052857, dated Jan. 17, 2013, Sahag n, Krause H.

* cited by examiner

*Primary Examiner* — Nizal Chandrakumar
(74) *Attorney, Agent, or Firm* — McCarter & English, LLP; Steven G. Davis; Mei Bai

(57) ABSTRACT

This invention relates to compounds that are agonists of the muscarinic M1 receptor and which are useful in the treatment of muscarinic M1 receptor mediated diseases. Also provided are pharmaceutical compositions containing the compounds and the therapeutic uses of the compounds. Compounds provided are of formula I, where n is 1 or 2; p is 0, 1 or 2; q is 0, 1 or 2; and $R_1$-$R_6$ are as defined herein.

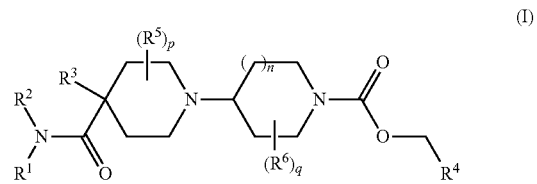

(I)

10 Claims, 2 Drawing Sheets

Figure 1:
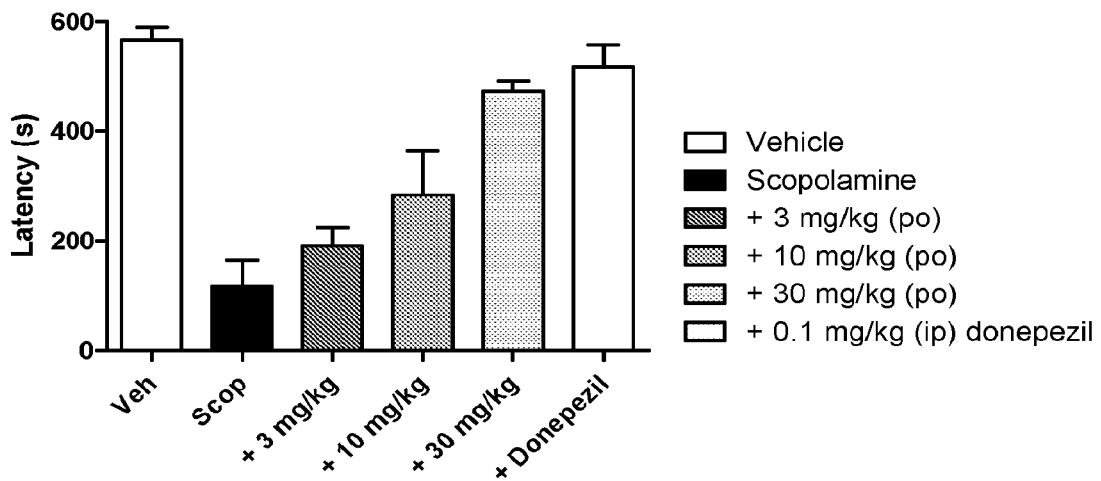

* p<0.05 verses vehicle
Bonferroni post test

Drug dose of 3, 10 and 30 mg/kg (po), Donepezil 0.1 mg/kg (ip) and galanthamine 3 mg/kg (ip)

MUSCARINIC M1 RECEPTOR AGONISTS

RELATED APPLICATION INFORMATION

This application is a divisional of U.S. patent application Ser. No. 14/941,328, filed Nov. 13, 2015, which is a continuation of U.S. patent application Ser. No. 14/358,984, filed May 16, 2014, which is a 371 of International Application No. PCT/GB2012/052857, filed Nov. 16, 2012, which claims to U.S. Provisional Application No. 61/632,813, filed Nov. 18, 2011, all of which are herein incorporated by reference.

This invention relates to compounds that are agonists of the muscarinic M1 receptor and which are useful in the treatment of muscarinic M1 receptor mediated diseases. Also provided are pharmaceutical compositions containing the compounds and the therapeutic uses of the compounds.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which also has cognitive impairment as an important component of the clinical picture, mAChR density is reduced in the pre-frontal cortex, hippocampus and caudate putamen of schizophrenic subjects (Dean et al., 2002 *Mol Psychiatry*). Furthermore, in animal models, blockade or damage to central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting adverse events resulting from stimulation of peripheral $M_2$ and $M_3$ mAChRs including disturbed gastrointestinal motility, bradycardia, nausea and vomiting (http://www.drugs.com/pro/donepezil.html; http://www.drugs.com/pro/rivastigmine.html).

Further discovery efforts have targeted the identification of direct $M_1$ mAChR agonists with the aim of inducing selective improvements in cognitive function with a favourable adverse effect profile. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain pathologies: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, nonamyloidogenic and amyloidogenic. Cleavage of APP by γ-secretase is common to both pathways, but in the former APP is cleaved by an α-secretase to yield soluble APPα. However, in the amyloidogenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 *Neuron*). The mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Preclinical studies have suggested that mAChR agonists display an atypical antipsychotic-like profile in a range of pre-clinical paradigms. The mAChR agonist, xanomeline, reverses a number of dopamine mediated behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*).

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 *Arch Neurol*). This compound was also assessed in a small Phase II study of schizophrenics and gave a significant reduction in positive and negative symptoms when compared to placebo control (Shekhar et al., 2008 *Am J Psych*). However, in all clinical studies xanomeline and other related mAChR agonists have displayed an unacceptable safety margin with respect to cholinergic adverse events, including nausea, gastrointestinal pain, diahorrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage; however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the M1 receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 *Bioorg Med Chem Lett*; Johnson et al., 2010 *Bioorg Med Chem Lett*; Budzik et al., 2010 *ACS Med Chem Lett*). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ mAChR over the $M_2$ and $M_3$ receptor subtypes.

SUMMARY OF THE INVENTION

The present invention provides compounds having activity as muscarinic M1 receptor agonists. More particularly, the invention provides compounds that exhibit selectivity for the M1 receptor relative to the M2, M3 and M4 receptor subtypes. Accordingly, in a first embodiment (Embodiment 1.1), the invention provides a compound of the formula (1):

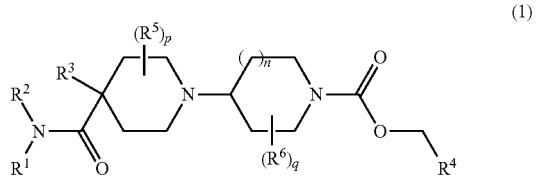

(1)

or a salt thereof, wherein:
n is 1 or 2;
p is 0, 1 or 2;
q is 0, 1 or 2;

$R^1$ is a $C_{1-10}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^2$ is hydrogen or a $C_{1-10}$ non-aromatic hydrocarbon group;

or $R^1$ and $R^2$ together with the nitrogen atom to which they are attached form a non-aromatic heterocyclic group of four to nine ring members, wherein the heterocyclic ring may optionally contain a second heteroatom selected from O, N and S and oxidised forms thereof; and wherein the heterocyclic ring may optionally be substituted with one to six more substitutents selected from $C_{1-2}$ alkyl; fluorine; and cyano;

$R^3$ is selected from hydrogen; halogen; cyano; hydroxy; $C_{1-3}$ alkoxy; and a $C_{1-5}$ non-aromatic hydrocarbon group which is optionally substituted with one to six fluorine atoms and wherein one or two, but not all, carbon atoms of the hydrocarbon group may optionally be replaced by a heteroatom selected from O, N and S;

$R^4$ is a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$ is absent or is fluorine; and
$R^6$ is absent or is fluorine.

FIGURES

Figure 2:
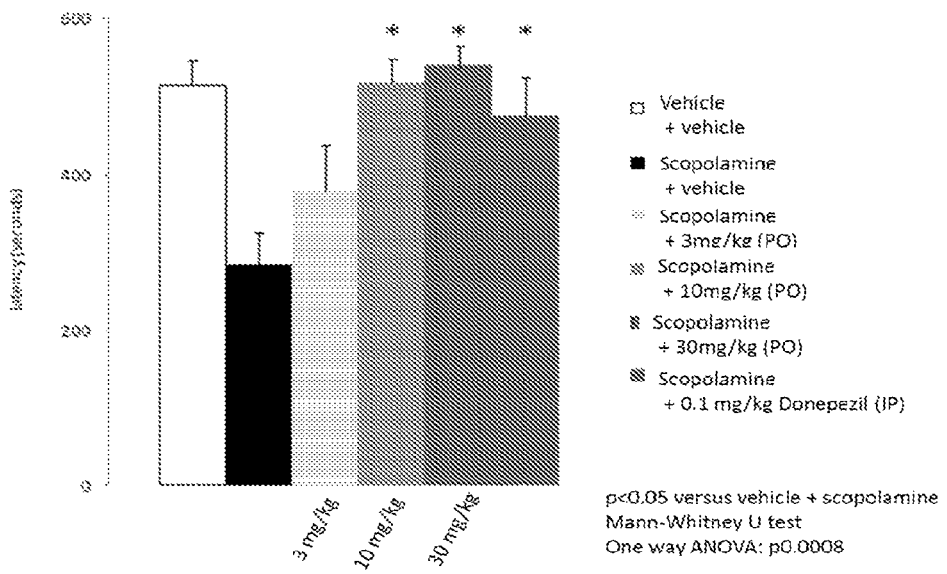
Figure 3:
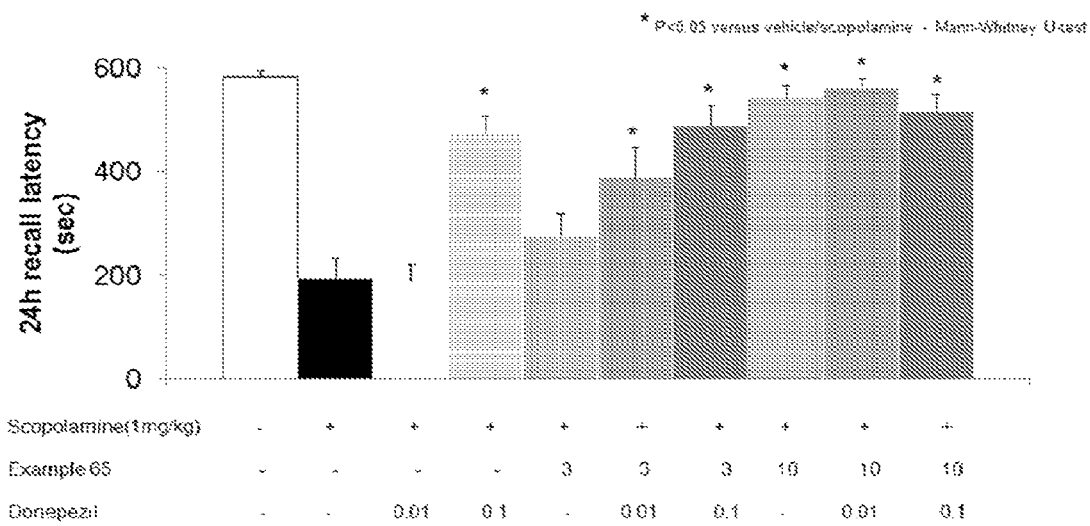

FIGS. 1-4 show the efficacy of the compounds of the invention. FIGS. 1-3 relate to the passive avoidance assay described in part B. Studies were carried out as described previously by Foley et al., (2004) Neuropsychopharmacology. In the passive avoidance task scopolamine administration (1 mg/kg, i.p.) at 6 hours following training rendered animals amnesic of the paradigm. A dose range of 3, 10, and 30 mg/kg (po) free base, administered 90 minutes prior to the training period via oral gavage, was examined.

FIG. 1 shows that Example 27 was found to reverse scopolamine-induced amnesia of the paradigm in a dose-dependent manner, with an approximate $ED_{50}$ of ca. 10 mg/kg (po). The effect of 30 mg/kg was similar to that produced by the cholinesterase inhibitor donepezil (0.1 mg/kg, ip) which served as a positive control.

FIG. 2 shows that Example 65 was found to reverse scopolamine-induced amnesia of the paradigm in a dose-dependent manner, with significant effects observed after acute administration of 10 and 30 mg/kg (p<0.05; Bonferroni post hoc test). The effect at 10 and 30 mg/kg was not significantly different to that produced by the cholinesterase inhibitor donepezil (0.1 mg/kg, i.p.), which served as a positive control.

FIG. 3 shows that Example 65 was found to reverse scopolamine-induced amnesia in a dose-dependent manner, with significant effects observed after acute administration of 10 mg/kg (po) (p<0.05; Bonferroni post hoc test). The effect at 10 mg/kg was not significantly different to that produced by the cholinesterase inhibitor donepezil (0.1 mg/kg, i.p.), which served as a positive control. Combination of Example 65 and donepezil did not result in a loss of activity, rather the combination had an additive effect at each dose combination as analysed by Mann Whitney u-test.

Figure 4:
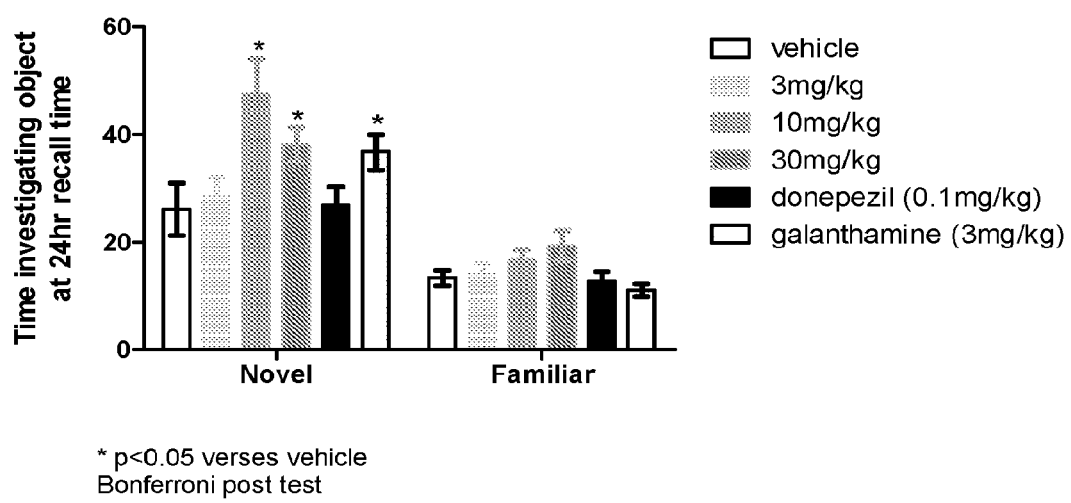

FIG. 4 shows the effects of Example 65 in a rodent object recognition assay described in Example D. Statistical analysis determined that treatment with 10 and 30 mg/kg for Example 65 and 3 mg/kg of the positive control galanthamine significantly improved novel object recognition memory when compared to vehicle-treated controls (p<0.05). Donepezil (0.1 mg/kg) was without effect on novel object recognition. During the 10 minute training period in the apparatus, animals were scored for exploratory behaviour. There was no difference as regards exploration for either object or between vehicle-treated controls and any drug treatment group.

DETAILED DESCRIPTION

The present invention provides compounds having activity as muscarinic M1 receptor agonists. More particularly, the invention provides compounds that exhibit selectivity for the M1 receptor relative to the M2, M3 and M4 receptor subtypes. Accordingly, in a first embodiment (Embodiment 1.1), the invention provides a compound of the formula (1):

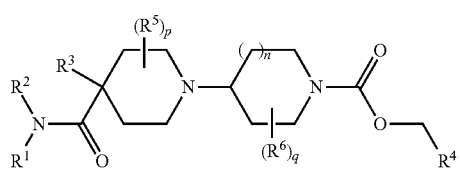

(1)

or a salt thereof, wherein:

n is 1 or 2;
p is 0, 1 or 2;
q is 0, 1 or 2;
$R^1$ is a $C_{1-10}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
$R^2$ is hydrogen or a $C_{1-10}$ non-aromatic hydrocarbon group;
or $R^1$ and $R^2$ together with the nitrogen atom to which they are attached form a non-aromatic heterocyclic group of four to nine ring members, wherein the heterocyclic ring may optionally contain a second heteroatom selected from O, N and S and oxidised forms thereof; and wherein the heterocyclic ring may optionally be substituted with one to six more substitutents selected from $C_{1-2}$ alkyl; fluorine; and cyano;
$R^3$ is selected from hydrogen; halogen; cyano; hydroxy; $C_{1-3}$ alkoxy; and a $C_{1-5}$ non-aromatic hydrocarbon group which is optionally substituted with one to six fluorine atoms and wherein one or two, but not all, carbon atoms of the hydrocarbon group may optionally be replaced by a heteroatom selected from O, N and S;
$R^4$ is a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
$R^5$ is absent or is fluorine; and
$R^6$ is absent or is fluorine.

Particular and preferred compounds of the formula (1) are as defined in the following Embodiments 1.2 to 1.53:

1.2 A compound according to Embodiment 1.1 wherein n is 1.
1.3 A compound according to Embodiment 1.1 wherein n is 2.
1.4 A compound according to any one of Embodiments 1.1 to 1.3 wherein $R^1$ is a $C_{1-10}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof; the $C_{1-10}$ non-aromatic hydrocarbon group containing 0, 1 or 2 carbon-carbon multiple bonds.
1.5 A compound according to any one of Embodiments 1.1 to 1.4 wherein $R^1$ is selected from $C_{1-6}$ alkyl; $C_{2-6}$ alkenyl; $C_{2-6}$ alkynyl; and $C_{1-10}$ non-aromatic hydrocarbon groups consisting of or containing a $C_{3-10}$ cycloalkyl or $C_{5-6}$ cycloalkenyl group; each of the said alkyl, alkenyl, alkynyl and non-aromatic hydrocarbon groups being optionally substituted with one to six fluorine atoms; and wherein one or two, but not all, carbon atoms of each of the alkyl, alkenyl, alkynyl and non-aromatic hydrocarbon groups may optionally be replaced by a heteroatom selected from O, N and S and oxidised forms thereof.
1.6 A compound according to any one of Embodiments 1.1 to 1.5 wherein $R^1$ is selected from:
  $C_{1-6}$ alkyl optionally substituted with 1 to 6 fluorine atoms;
  methoxy-$C_{1-4}$ alkyl optionally substituted with 1 to 6 fluorine atoms;
  $C_{1-6}$ alkoxy;
  $C_{2-6}$ alkenyl;
  $C_{2-6}$ alkynyl;
  $C_{3-6}$ cycloalkyl optionally substituted with one or two methyl groups;
  $C_{4-5}$ cycloalkyl-$CH_2$— wherein the $C_{4-5}$ cycloalkyl moiety is optionally substituted with one $C_{1-2}$ alkyl group and wherein one carbon atom of the $C_{4-5}$ cycloalkyl moiety may optionally be replaced by an oxygen atom;
  cyclopropyl-$C_{1-3}$ alkyl;
  cyclopentenyl; and
  methyl-bicyclo[2.2.2]octanyl.
1.7 A compound according to any one of Embodiments 1.1 to 1.5 wherein $R^1$ is selected from:
  $C_{1-6}$ alkyl optionally substituted with 1 to 6 fluorine atoms;
  $C_{3-6}$ cycloalkyl optionally substituted with one or two methyl groups;
  $C_{4-5}$ cycloalkyl-$CH_2$— wherein the $C_{4-5}$ cycloalkyl moiety is optionally substituted with one $C_{1-2}$ alkyl group and wherein one carbon atom of the $C_{4-5}$ cycloalkyl moiety may optionally be replaced by an oxygen atom;
  cyclopropyl-$C_{1-3}$ alkyl; and
  methyl-bicyclo[2.2.2]octanyl.
1.8 A compound according to any one of Embodiments 1.1 to 1.5 wherein $R^1$ is $C_{1-6}$ alkyl optionally substituted with 1 to 6 fluorine atoms.
1.9 A compound according to any one of Embodiments 1.1 to 1.5 wherein $R^1$ is $C_{3-6}$ cycloalkyl optionally substituted with one or two methyl groups.
1.10 A compound according to any one of Embodiments 1.1 to 1.5 wherein $R^1$ is $C_{4-5}$ cycloalkyl-$CH_2$— wherein the $C_{4-5}$ cycloalkyl moiety is optionally substituted with one $C_{1-2}$ alkyl group and wherein one carbon atom of the $C_{4-5}$ cycloalkyl moiety may optionally be replaced by an oxygen atom.

1.11 A compound according to any one of Embodiments 1.1 to 1.5 wherein $R^1$ is cyclopropyl-$C_{1-3}$ alkyl.

1.12 A compound according to any one of Embodiments 1.1 to 1.5 wherein $R^1$ is methyl-bicyclo[2.2.2]octanyl.

1.13 A compound according to any one of Embodiments 1.1 to 1.5 wherein $R^1$ is selected from groups A to AS below:

2-methylpropyl — A

tert-butyl — B

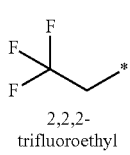

2,2,2-trifluoroethyl — C

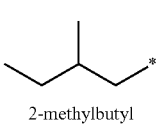

2-methylbutyl — D

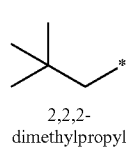

2,2,2-dimethylpropyl — E

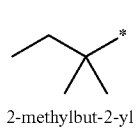

2-methylbut-2-yl — F

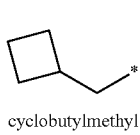

cyclobutylmethyl — G

ethyl — H

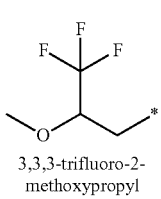

3,3,3-trifluoro-2-methoxypropyl — I

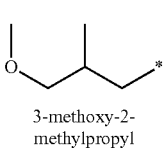

3-methoxy-2-methylpropyl — J

-continued

Tetrahydrofuran-3-ylmethyl — K

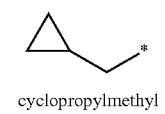

cyclopropylmethyl — L

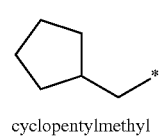

cyclopentylmethyl — M

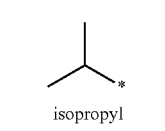

isopropyl — N

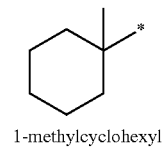

1-methylcyclohexyl — O

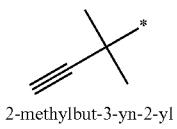

2-methylbut-3-yn-2-yl — P

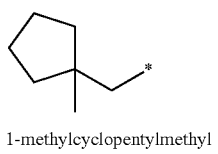

1-methylcyclopentylmethyl — Q

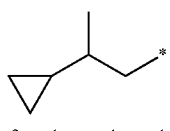

2-cyclopropylpropyl — R

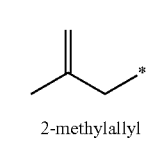

2-methylallyl — S

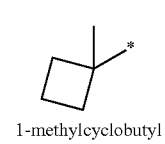

1-methylcyclobutyl — T

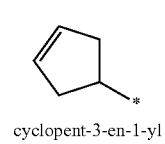

cyclopent-3-en-1-yl — U

-continued

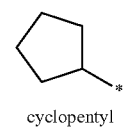
cyclopentyl — V

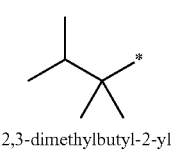
2,3-dimethylbutyl-2-yl — W

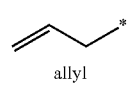
allyl — X

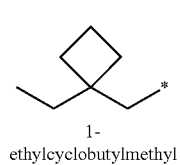
1-ethylcyclobutylmethyl — Y

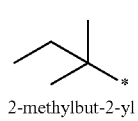
2-methylbut-2-yl — Z

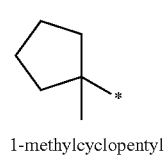
1-methylcyclopentyl — AA

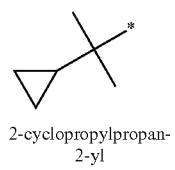
2-cyclopropylpropan-2-yl — AB

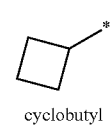
cyclobutyl — AC

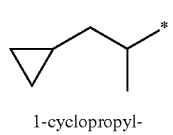
1-cyclopropyl-propan-2-yl — AD

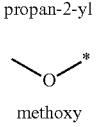
methoxy — AE

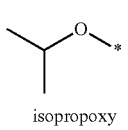
isopropoxy — AF

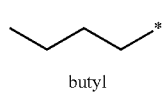
butyl — AG

-continued

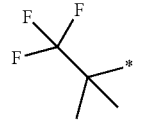
1,1,1-trifluoro-2-methyl-propan-2-yl — AH

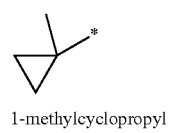
1-methylcyclopropyl — AI

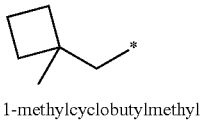
1-methylcyclobutylmethyl — AJ

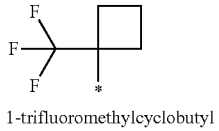
1-trifluoromethylcyclobutyl — AK

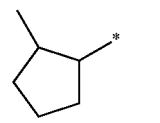
2-methylcyclopentyl — AL

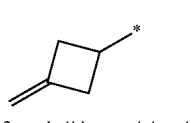
3-methylidenecyclobutyl — AM

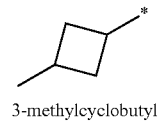
3-methylcyclobutyl — AN

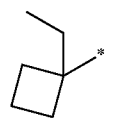
1-ethylcyclobutyl — AO

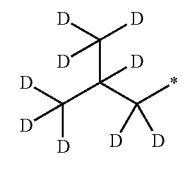
($^2H_3$)methyl($^2H_6$)propyl — AP

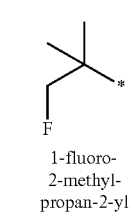
1-fluoro-2-methyl-propan-2-yl — AQ

-continued

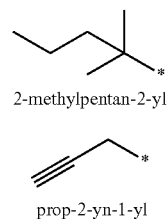

2-methylpentan-2-yl AR prop-2-yn-1-yl AS where the asterisk denotes the point of attachment of the group to the amide nitrogen atom.

1.14 A compound according to Embodiment 1.13 wherein $R^1$ is selected from groups A, B, D, E, F, G, L, M, N, O, Q, R, T, V, W, Y, AA, AB, AC, AJ, AK, AO, AP and AR (wherein $R^1$ is selected from 2-methylpropyl, tert-butyl, 2-methylbutyl, 2,2-dimethylpropyl, 2-methylbut-2-yl, cyclobutyl methyl, cyclopropylmethyl, cyclopentylmethyl, isopropyl, 1-methylcyclohexyl, 1-methylcyclopentyl methyl, 2-cyclopropylpropyl, 1-methylcyclobutyl, cyclopentyl, 2,3-dimethylbutan-2-yl, 1-ethylcyclobutylmethyl, 1-methylcyclopentyl, 2-cyclopropylpropan-2-yl, cyclobutyl, 1-methylcyclobutylmethyl, 1-(trifluoromethyl)cyclobutyl, 1-ethylcyclobutyl, ($^2$H$_3$)methyl($^2$H$_6$)propyl and 2-methylpentan-2-yl groups).

1.15 A compound according to any one of Embodiments 1.1 to 1.6 wherein $R^1$ is selected from 2-methylpropyl; 2,2-dimethylpropyl; tert-butyl; 2-methyl-but-2-yl; 2,3-dimethylbut-2-yl; cyclopropylmethyl; cyclobutylmethyl; cyclopentyl; cyclopentylmethyl; 1-methylcyclobutyl; 1-methylcyclopentyl; 1 methylcyclohexyl; 1-methylcyclopentylmethyl; cyclopropyl-prop-2-yl; and 1-ethyl-cyclobutylmethyl groups.

1.15a A compound according to 1.14 wherein $R^1$ is selected from groups A, F, G, O, R, T, V, W, Y, AA, AB, AJ, AO and AP (wherein R' is selected from 2-methylpropyl, 2-methylbutyl, cyclobutylmethyl, 1-methylcyclohexyl, 2-cyclopropylpropyl, 1-methylcyclobutyl, cyclopentyl, 2,3-dimethylbutan-2-yl, 1-ethylcyclobutylmethyl, 1-methylcyclopentyl, 2-cyclopropylpropan-2-yl, 1-methylcyclobutylmethyl and 1-ethylcyclobutyl and ($^2$H$_3$)methyl($^2$H$_6$)propyl groups).

1.16 A compound according to Embodiment 1.15 or 1.15a wherein $R^1$ is selected from 2-methylpropyl and 1-methylcyclobutyl.

1.17 A compound according to Embodiment 1.16 wherein $R^1$ is 2-methylpropyl.

1.18 A compound according to Embodiment 1.16 wherein $R^1$ is 1-methylcyclobutyl.

1.19 A compound according to any one of Embodiments 1.1 to 1.18 wherein $R^2$ is selected from hydrogen and $C_{1-6}$ alkyl.

1.20 A compound according to Embodiment 1.19 wherein $R^2$ is selected from hydrogen, methyl, ethyl and isopropyl.

1.21 A compound according to Embodiment 1.20 wherein $R^2$ is hydrogen.

1.22 A compound according to any one of Embodiments 1.1 to 1.21 wherein $R^3$ is selected from hydrogen, halogen, cyano, hydroxy, $C_{1-3}$alkoxy and $C_{1-4}$ alkyl.

1.23 A compound according to Embodiment 1.22 wherein $R^3$ is selected from hydrogen, fluorine and methyl, cyano and methoxy.

1.23a A compound according to Embodiment 1.22 wherein $R^3$ is selected from hydrogen, fluorine and methyl, cyano and methoxy and $R^1$ is 1-methylcyclobutyl.

1.24 A compound according to Embodiment 1.23 or 1.23a wherein $R^3$ is selected from hydrogen and fluorine.

1.25 A compound according to Embodiment 1.24 wherein $R^3$ is hydrogen.

1.26 A compound according to Embodiment 1.24 wherein $R^3$ is fluorine.

1.27 A compound according to any one of Embodiments 1.1 to 1.26 wherein $R^4$ is an acyclic $C_{1-6}$ hydrocarbon group.

1.28 A compound according to Embodiment 1.27 wherein $R^4$ is an acyclic $C_{1-3}$ hydrocarbon group.

1.29 A compound according to Embodiment 1.20 wherein $R^4$ is a $C_{1-3}$ alkyl group or a $C_{2-3}$ alkynyl group.

1.30 A compound according to Embodiment 1.29 wherein $R^4$ is selected from methyl, ethyl, ethynyl and 1-propynyl.

1.31 A compound according to Embodiment 1.30 wherein $R^4$ is methyl.

1.32 A compound according to any one of Embodiments 1.1 to 1.31 wherein $R^5$ is fluorine.

1.33 A compound according to any one of Embodiments 1.1 to 1.32 wherein p is 0 or 1.

1.34 A compound according to any one of Embodiments 1.1 to 1.31 wherein p is 0.

1.35 A compound according to any one of Embodiments 1.1 to 1.32 wherein p is 1.

1.36 A compound according to any one of Embodiments 1.1 to 1.35 wherein $R^6$ is fluorine.

1.37 A compound according to any one of Embodiments 1.1 to 1.36 wherein q is 0 or 1.

1.38 A compound according to any one of Embodiments 1.1 to 1.35 wherein q is 1.

1.39 A compound according to any one of Embodiments 1.1 to 1.36 wherein q is 1.

1.40 A compound according to Embodiment 1.1 having the formula (2):

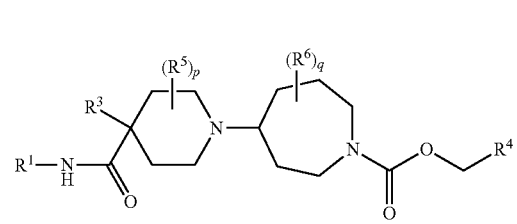

(2)

wherein $R^1$, $R^3$, $R^4$, $R^5$, $R^6$, p and q are as defined in any one of Embodiments 1.1 and 1.3 to 1.39.

1.41 A compound according to Embodiment 1.40 having the formula (3):

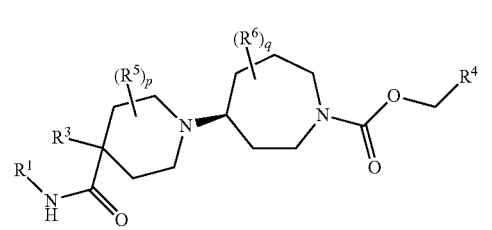

(3)

wherein $R^1$, $R^3$, $R^4$, $R^5$, $R^6$, p and q are as defined in any one of Embodiments 1.1 and 1.3 to 1.39.

1.42 A compound according to Embodiment 1.40 having the formula (4):

$$\text{(4)}$$

wherein $R^1$, $R^3$, $R^4$, $R^5$, $R^6$, p and q are as defined in any one of Embodiments 1.1 and 1.3 to 1.39.

1.43 A compound according to Embodiment 1.1 which is as defined in any one of Examples 1 to 64.

1.43a A compound according to Embodiment 1.1 which is as defined in any one of Examples 65 to 82.

1.43b A compound according to Embodiment 1.1 which is as defined in any one of Examples 1 to 82.

1.44 A compound according to Embodiment 1.43 which is selected from the compounds of Examples 6, 7, 8, 9, 10, 11, 15, 16, 17, 18, 27, 30, 31, 37, 39, 40, 41, 42, 43, 44, 45, 46, 48, 49, 50, 51, 52, 53, 54, 55, 56, 57, 58, 63 and 64 and salts thereof or a compound according to Embodiment 1.43a which is selected from the compounds of Examples 65, 66, 67, 73, 74, 75, 77, 78, 79, 80, 81 and 82 and salts thereof.

1.45 A compound according to Embodiment 1.44 which is ethyl 4-(4-((2-methylpropyl)carbamoyl)piperidin-1-yl)azepane-1-carboxylate or a salt thereof.

1.46 A compound according to Embodiment 1.45 which is ethyl (4S)-4-[4-((2-methylpropyl)methylcarbamoyl)piperidin-1-yl]azepane-1-carboxylate or a salt thereof.

1.47 A compound according to Embodiment 1.45 which is ethyl (4R)-4-[4-((2-methylpropyl)methylcarbamoyl)piperidin-1-yl]azepane-1-carboxylate or a salt thereof.

1.48 A compound according to Embodiment 1.44 which is ethyl 4-(4-((1-methylcyclobutyl)carbamoyl)piperidin-1-yl)azepane-1-carboxylate or a salt thereof.

1.48a A compound according to Embodiment 1.48 which is ethyl (4S)-4-[4-[(1-methylcyclobutyl)carbamoyl]-1-piperidyl]azepane-1-carboxylate or a salt thereof.

1.49 A compound according to any one of Embodiments 1.1 to 1.48a having a molecular weight of less than 550, for example less than 500, or less than 450.

1.50 A compound according to any one of Embodiments 1.1 to 1.49 which is in the form of a salt.

1.51 A compound according to Embodiment 1.50 wherein the salt is an acid addition salt.

1.52 A compound according to Embodiment 1.50 or Embodiment 1.51 wherein the salt is a pharmaceutically acceptable salt.

Definitions

In this application, the following definitions apply, unless indicated otherwise.

The term "treatment" in relation to the uses of the compounds of the formula (1), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "non-aromatic hydrocarbon group" (as in "$C_{1-10}$ non-aromatic hydrocarbon group" or "acyclic $C_{1-5}$ non-aromatic hydrocarbon group") refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

Salts

Many compounds of the formula (1) can exist in the form of salts, for example acid addition salts or, in certain cases salts of organic and inorganic bases such as carboxylate, sulfonate and phosphate salts. All such salts are within the scope of this invention, and references to compounds of the formula (1) include the salt forms of the compounds as defined in Embodiments 1.50 to 1.53.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.51) may be formed with a wide variety of acids, both inorganic and organic. Examples of acid addition salts falling within Embodiment 1.51 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1 S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, acetyl leucine, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, (−)-D-tartaric, (−)-dibenzoyltartaric, thiocyanic, p-toluenesulfonic, undecylenic and valeric acids, as well as acylated amino acids and cation exchange resins.

Where the compounds of the formula (1) contain an amine function, these may form quaternary ammonium salts, for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.53a), the invention provides a geometric isomer of a compound according to any one of Embodiments 1.1 to 1.53.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.54) the invention provides a compound according to any one of Embodiments 1.1 to 1.53 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-tartaric acid, acetyl leucine, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.55), the invention provides compositions containing a compound according to Embodiment 1.54 having one or more chiral centres, wherein at least 55% (e.g. at least 60%, 65%, 70%, 75%, 80%, 85%, 90% or 95%) of the compound of Embodiment 1.54 is present as a single optical isomer (e.g. enantiomer or diastereoisomer).

In one general embodiment (Embodiment 1.56), 99% or more (e.g. substantially all) of the total amount of the compound (or compound for use) of Embodiment 1.54 is present as a single optical isomer.

For example, in one embodiment (Embodiment 1.57) the compound is present as a single enantiomer.

In another embodiment (Embodiment 1.58), the compound is present as a single diastereoisomer.

The invention also provides mixtures of optical isomers, which may be racemic or non-racemic. Thus, the invention provides:

1.59 A compound according to Embodiment 1.54 which is in the form of a racemic mixture of optical isomers.

1.60 A compound according to Embodiment 1.54 which is in the form of a non-racemic mixture of optical isomers.

Isotopes

The compounds of the invention as defined in any one of Embodiments 1.1 to 1.60 may contain one or more isotopic substitutions, and a reference to a particular element includes within its scope all isotopes of the element. For example, a reference to hydrogen includes within its scope $^{1}$H, $^{2}$H (D), and $^{3}$H (T). Similarly, references to carbon and oxygen include within their scope respectively $^{12}$C, $^{13}$C and $^{14}$C and $^{16}$O and $^{18}$O.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.61), the compound of any one of Embodiments 1.1 to 1.60 contains no radioactive isotopes. Such compounds are preferred for therapeutic use. In another embodiment (Embodiment 1.62), however, the compound of any one of Embodiments 1.1 to 1.60 may contain one or more radioisotopes. Compounds containing such radioisotopes may be useful in a diagnostic context.

Solvates

Compounds of the formula (1) as defined in any one of Embodiments 1.1 to 1.62 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.63 and 1.64, the invention provides:

1.63 A compound according to any one of Embodiments 1.1 to 1.62 in the form of a solvate.

1.64 A compound according to Embodiment 1.63 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.65), the invention provides a compound as defined in any one of Embodiments 1.1 to 1.62 in an anhydrous form (e.g. anhydrous crystalline form).

Crystalline and Amorphous Forms

The compounds of any one of Embodiments 1.1 to 1.65 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. J. Pharm. Sci. (1997), 86, 1).

Accordingly, in further embodiments, the invention provides:

1.66 A compound according to any one of Embodiments 1.1 to 1.65 in a crystalline form.

1.67 A compound according to any one of Embodiments 1.1 to 1.65 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.68 A compound according to any one of Embodiments 1.1 to 1.65 which is in an amorphous form.

Prodrugs

The compounds of the formula (1) as defined in any one of Embodiments 1.1 to 1.62 may be presented in the form of a pro-drug. By "prodrugs" is meant for example any compound that is converted in vivo into a biologically active compound of the formula (1), as defined in any one of Embodiments 1.1 to 1.62.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.69), the invention provides a pro-drug of a compound as defined in any one of Embodiments 1.1 to 1.62 wherein the compound contains a functional group which is convertable under physiological conditions to form a hydroxyl group or amino group.

Complexes and Clathrates

Also encompassed by formula (1) in Embodiments 1.1 to 1.69 are complexes (e.g. inclusion complexes or clathrates with compounds such as cyclodextrins, or complexes with metals) of the compounds of Embodiments 1.1 to 1.69.

Accordingly, in another embodiment (Embodiment 1.70), the invention provides a compound according to any one of Embodiments 1.1 to 1.69 in the form of a complex or clathrate.

Biological Activity and Therapeutic Uses

The compounds of the present invention have activity as muscarinic M1 receptor agonists. The muscarinic activity of the compounds can be determined using the Phospho-ERK1/2 assay described in Example A below.

A significant advantage of compounds of the invention is that they have selectivity for the M1 receptor relative to the M2 and M3 receptor subtypes. For example, whereas compounds of the invention typically have $pEC_{50}$ values of at least 6 (preferably at least 6.5) and $E_{max}$ values of greater than 80 (preferably greater than 100) against the M1 receptor in the functional assay described in Example A, they may have $pEC_{50}$ values of less than 6 (and usually less than 5) and $E_{max}$ values of less than 50% when tested against the M2 and M3 subtypes in the functional assay of Example A.

Accordingly, in Embodiments 2.1 to 2.9, the invention provides:

2.1 A compound according to any one of Embodiments 1.1 to 1.70 for use in medicine.

2.2 A compound according to any one of Embodiments 1.1 to 1.70 for use as a muscarinic M1 receptor agonist.

2.3 A compound according to any one of Embodiments 1.1 to 1.70 which is a muscarinic M1 receptor agonist having a $pEC_{50}$ in the range from 6.0 to 7.9 and an $E_{max}$ of at least 90 against the M1 receptor in the assay of Example A herein or an assay substantially similar thereto.

2.4 A compound according to Embodiment 2.3 which is a muscarinic M1 receptor agonist having a $pEC_{50}$ in the range from 6.5 to 7.5.

2.4a A compound according to Embodiment 2.3 which is a muscarinic M1 receptor agonist having a pEC50 in the range from 6.8 to 7.9.

2.4b A compound according to Embodiment 2.3 which is a muscarinic M1 receptor agonist having a pEC50 in the range from 7.1 to 7.9.

2.5 A compound according to Embodiment 2.3, Embodiment 2.4, Embodiment 2.4a or Embodiment 2.4b having an $E_{max}$ of at least 100 against the M1 receptor.

2.6 A compound according to any one of Embodiments 2.3 to 2.5 which is selective for the M1 receptor compared to the muscarinic M2 and M3 receptors.

2.7 A compound according to any one of Embodiments 2.3 to 2.6 which has a $pEC_{50}$ of less than 5 and an $E_{max}$ of less than 50 against the muscarinic M2 and M3 receptor subtypes.

2.8 A compound according to Embodiment 2.7 which has a $pEC_{50}$ of less than 4.5 and/or an $E_{max}$ of less than 30 against the muscarinic M2 and M3 receptor subtypes.

2.9 A compound according to any one of Embodiments 1.1 to 1.70 and Embodiments 2.3 to 2.8 for use in the treatment of a disease or condition mediated by the muscarinic M1 receptor.

By virtue of their muscarinic M1 receptor agonist activity, compounds of the invention can be used in the treatment of Alzeimer's disease, schizophrenia and other psychotic disorders, cognitive disorders and other diseases mediated by the muscarinic M1 receptor.

Accordingly, in Embodiments 2.10 to 2.13, the invention provides:

2.10 A compound according to any one of Embodiments 1.1 to 1.70 for use in the treatment of a cognitive disorder or psychotic disorder.

2.11 A compound for use in according to Embodiment 2.10 wherein the cognitive disorder or psychotic disorder comprises, arises from or is associated with a condition selected from cognitive impairment, mild cognitive impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as multiinfarct dementia, alcoholic dementia, hypothyroidism-related dementia, and dementia associated with other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and schizo-affective disorder.

2.12 A compound according to any one of Embodiments 1.1 to 1.70 for use in the treatment of Alzheimer's disease.

2.13 A compound according to any one of Embodiments 1.1 to 1.70 for use in the treatment of Schizophrenia.

2.14 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.70.

2.15 A method according to Embodiment 2.14 wherein the cognitive disorder comprises, arises from or is associated with a condition as defined in Embodiment 2.11.

2.16 A method according to Embodiment 2.15 wherein the cognitive disorder arises from or is associated with Alzheimer's disease.

2.17 A method according to Embodiment 2.16 wherein the cognitive disorder is Schizophrenia.

2.18 The use of a compound according to any one of Embodiments 1.1 to 1.70 for the manufacture of a medicament for the treatment of a cognitive disorder.

2.19 The use according to Embodiment 2.10 wherein the cognitive disorder comprises, arises from or is associated with a condition as defined in Embodiment 2.11.

2.20 The use according to Embodiment 2.19 wherein the cognitive disorder arises from or is associated with Alzheimer's disease.

2.21 The use according to Embodiments 2.19 wherein the cognitive disorder is Schizophrenia.

2.22 A compound according to any one of Embodiments 1.1 to 1.70 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.23 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.70.

2.24 A compound according to any one of Embodiments 1.1 to 1.70 for the treatment of peripheral disorders such as reduction of intra ocular pressure in glaucoma and treatment of dry eyes and dry mouth including Sjogren's Syndrome.

2.25 A method of treatment of peripheral disorders such as reduction of intra ocular pressure in glaucoma and treatment of dry eyes and dry mouth including Sjogren's Syndrome, which method comprises the administration of a therapeutically effective dose of a compound according to any one of Embodiments 1.1 to 1.70.

2.26 The use of a compound according to any one of Embodiments 1.1 to 1.70 for the manufacture of a medicament for the treatment or lessening the severity of acute, chronic, neuropathic, or inflammatory pain, arthritis, migraine, cluster headaches, trigeminal neuralgia, herpetic neuralgias, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain or for the treatment of peripheral disorders such as reduction of intra ocular pressure in glaucoma and treatment of dry eyes and dry mouth including Sjogren's Syndrome.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.70, which process comprises:

(A) the reaction of a compound of the formula (10)

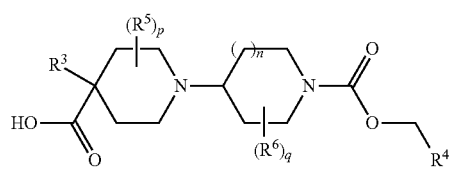

(10)

wherein $R^3$, $R^4$, $R^5$ and $R^6$ are as defined in any one of Embodiments 1.1 to 1.70 with a compound of the formula $R^1R^2NH$ under amide-forming conditions; or (B) the reaction of a compound of the formula (11):

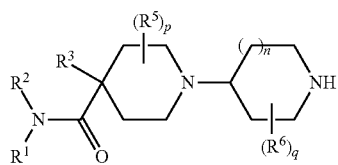

(11)

with a compound of the formula Cl—C(=O)O—CH$_2$—$R^4$, in the presence of a base; and optionally:

(C) converting one compound of the formula (1) to another compound of the formula (1).

In process variant (A), the reaction may be carried out in the presence of a reagent of the type commonly used in the formation of amide bonds. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC) (Sheehan et al, *J. Org. Chem.*, 1961, 26, 2525), uronium-based coupling agents such as O-(7-azabenzotriazol-1-yl)-N,N,N'—N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). A preferred amide coupling agent is HATU.

The coupling reaction is typically carried out in a non-aqueous, non-protic solvent such as acetonitrile, dioxane, dimethylsulphoxide, dichloromethane, dimethylformamide or N-methylpyrrolidinone, or in an aqueous solvent optionally together with one or more miscible co-solvents. The reaction can be carried out at room temperature or, where the reactants are less reactive at an appropriately elevated temperature, for example a temperature up to about 100° C., e.g. 50-80° C. The reaction may optionally be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. The acid chloride is typically reacted with the compound of formula $R^1R^2NH$ in the presence of a base such as sodium bicarbonate or sodium hydroxide. The acid chloride can be prepared using standard methods, for example by treatment of the acid with oxalyl chloride in the presence of a catalytic amount of dimethylformamide.

Process variant (B) is typically carried out in an aprotic solvent such as dichloromethane or dichloroethane in the presence of a non-interfering base such as triethylamine. The reaction may be conducted at room temperature.

Intermediate compounds of the formula (10) can be prepared by the series of reactions shown in Scheme 1 below.

Scheme 1

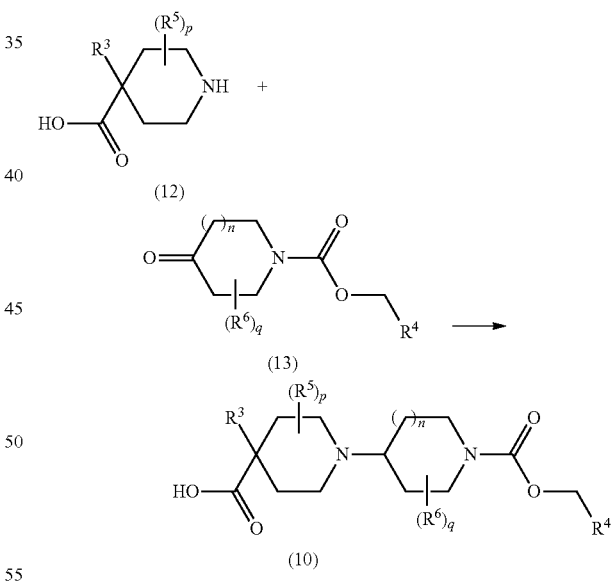

In reaction Scheme 1, the piperidine carboxylic acid (12) is reacted with the substituted ketone (13) under reductive amination conditions. The reductive amination reaction is typically carried out with mild heating (e.g. to a temperature of from about 40° C. to about 70° C.) using a borohydride reducing agent such as sodium triacetoxyborohydride in a solvent such as dichloromethane or dichloroethane containing acetic acid. In an alternative sequence of reactions, an ester (e.g. the ethyl ester) of the piperidine carboxylic acid (12) is reacted with the piperidone (13) in the presence of either sodium cyanoborohydride in combination with zinc chloride or sodium triacetoxyborohydride in combination with titanium isopropoxide to give an intermediate ester compound (not shown) which is then selectively hydrolysed under mild conditions using lithium hydroxide or sodium hydroxide to give compound (10).

Compounds of the formula (11) can be prepared by the sequence of reactions shown in Scheme 2 below.

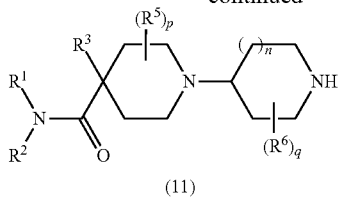

(11)

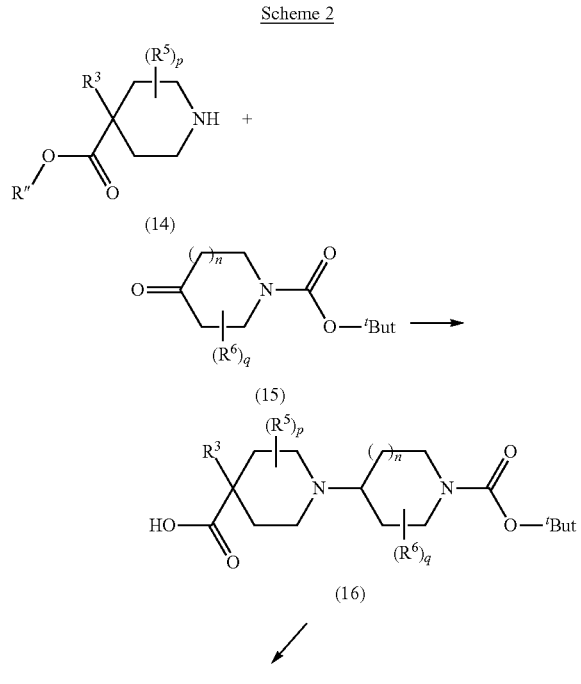

In Scheme 2, the piperidine ester (14, R″=ethyl) is reacted with the ketone (15) under reductive amination conditions of the type described above to give an intermediate ester (not shown) which is then selectively hydrolysed using lithium hydroxide to give the carboxylic acid (16). The carboxylic acid (16) is then reacted with an amine $HNR^1R^2$ under amide-forming conditions (see above) to give an intermediate amide compound (not shown) which is then deprotected by removal of the Boc group by treatment with acid (e.g. trifluoroacetic acid in dichloromethane) to give the compound (11).

In formula (1) and the formulae shown in the reaction Schemes 1 and 2 above, when "n" is 2, the right hand heterocyclic ring is an azepine ring and a chiral centre can exist at the carbon atom of the azepine ring which is attached to the piperidine ring. Although individual optical isomers can be isolated and purified by standard methods at the end of the reaction sequence, it is also possible to prepare compounds of the formula (1) wherein n is 2 having a desired stereochemistry at the chiral carbon atom by using chiral intermediates of the formula (16).

A synthetic route which provides chiral intermediate compounds of the formula (16) wherein n is 2 and $R^5$ is absent, is set out in Scheme 3 below.

Scheme 3

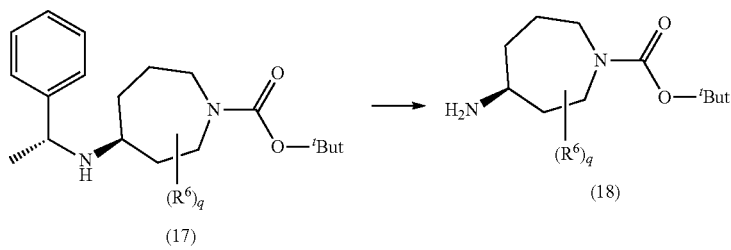

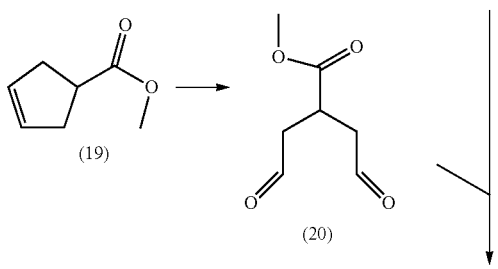

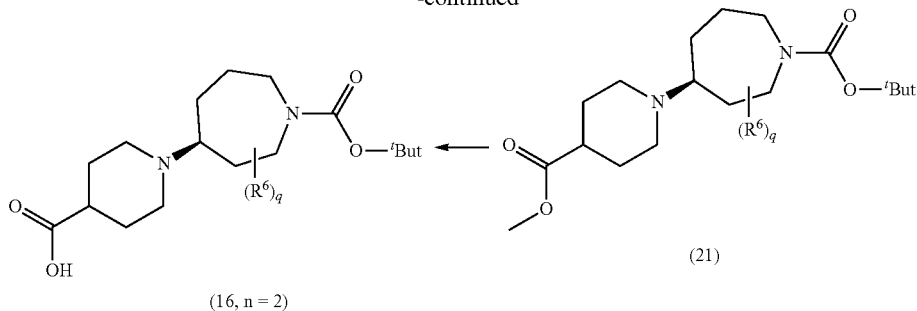

(16, n = 2) ← (21)

The starting material for the reaction sequence shown in Scheme 3 is the protected (4S)-4-aminoazepine derivative (17) in which the ring nitrogen of the azepine is protected by a Boc group and the 4-amino moiety is protected as a (1R)-1-phenethylamino group. The first step of the reaction sequence involves the removal of the phenethylamine protecting group using palladium hydroxide on carbon and ammonium formate in methanol with heating to give the 4-aminoazepine (18). The 4-aminoazepine (18) is then reacted with the dialdehyde (20) (which can be generated in situ by subjecting methyl cyclopent-3-ene-1-carboxylate to ozonolysis) under reductive amination conditions as described above (e.g. using sodium triacetoxyborohydride) to give the piperidinyl-azepine (21). Hydrolysis of the piperidine carboxylic ester group using sodium hydroxide gives the (S) optical isomer of the N-protected-azepinyl-piperidinyl carboxylic acid (16).

In order to give the corresponding (R) optical isomer of compound (16), the corresponding (4R)-4-aminoazepine isomer of compound (17) can be used as the starting material.

Once formed, one compound of the formula (1), or a protected derivative thereof, can be converted into another compound of the formula (1) by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.70 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1 to 82

The compounds of Examples 1 to 82 shown in Table 1 below have been prepared. Their NMR and LCMS properties and the methods used to prepare them are set out in Table 2.

TABLE 1

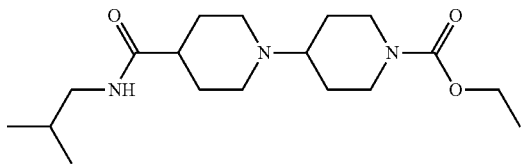

Example 1

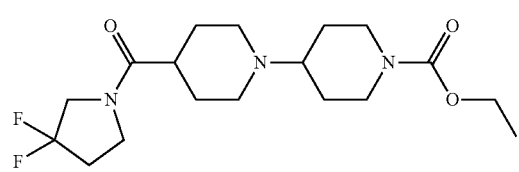 [SMILES: CCOC(=O)N1CCC(N2CCC(C(=O)N3CCC(F)(F)C3)CC2)CC1]

Example 2

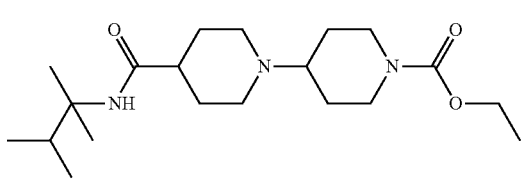 [SMILES: CCOC(=O)N1CCC(N2CCC(C(=O)NC(C)(C)C(C)C)CC2)CC1]

Example 3

TABLE 1-continued
| | |
|---|---|
| 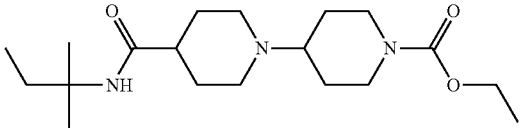 [SMILES: CCOC(=O)N1CCC(N2CCC(C(=O)NC(C)(C)CC)CC2)CC1] | Example 4 |
| 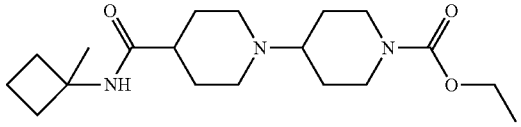 [SMILES: CCOC(=O)N1CCC(N2CCC(C(=O)NC3(C)CCC3)CC2)CC1] | Example 5 |
| 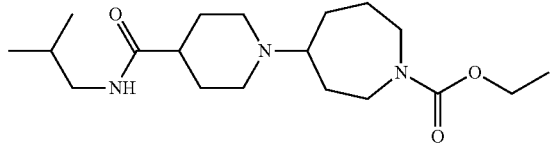 [SMILES: CCOC(=O)N1CCCC(N2CCC(C(=O)NCC(C)C)CC2)CC1] | Example 6 |
| 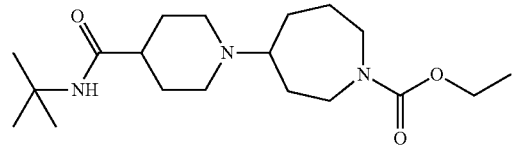 [SMILES: CCOC(=O)N1CCCC(N2CCC(C(=O)NC(C)(C)C)CC2)CC1] | Example 7 |
| 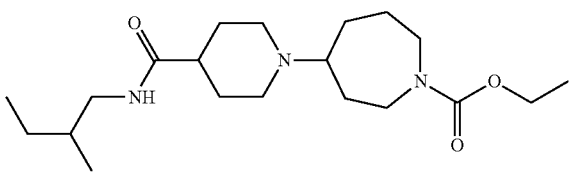 [SMILES: CCOC(=O)N1CCCC(N2CCC(C(=O)NCC(C)CC)CC2)CC1] | Example 8 |
| 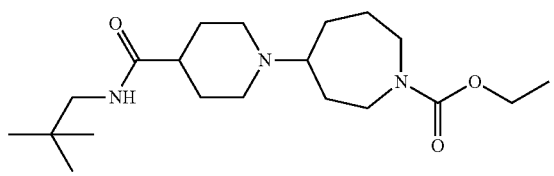 [SMILES: CCOC(=O)N1CCCC(N2CCC(C(=O)NCC(C)(C)C)CC2)CC1] | Example 9 |
| 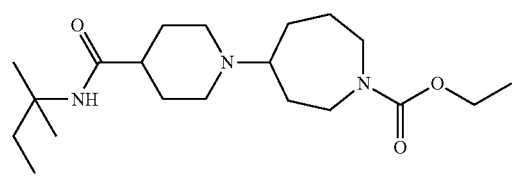 [SMILES: CCOC(=O)N1CCCC(N2CCC(C(=O)NC(C)(C)CC)CC2)CC1] | Example 10 |
| 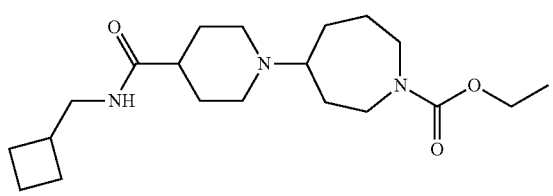 [SMILES: CCOC(=O)N1CCCC(N2CCC(C(=O)NCC3CCC3)CC2)CC1] | Example 11 |
| 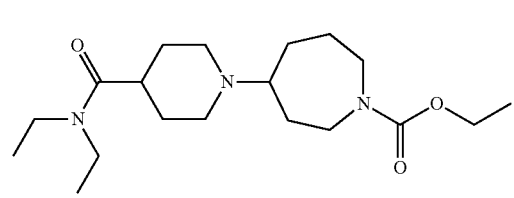 [SMILES: CCOC(=O)N1CCCC(N2CCC(C(=O)N(CC)CC)CC2)CC1] | Example 12 |

TABLE 1-continued
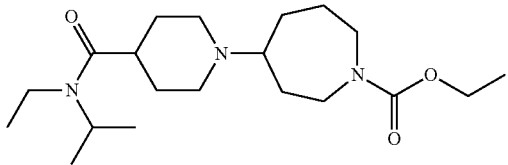
Example 13
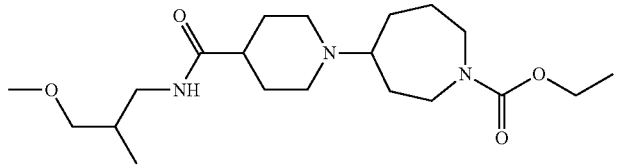 [SMILES: CCOC(=O)N1CCCC(N2CCC(C(=O)NCC(C)COC)CC2)CC1]
Example 14
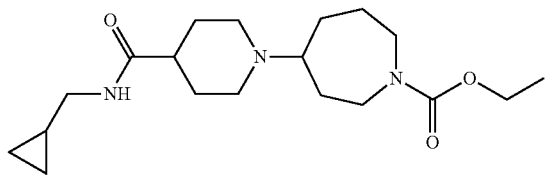 [SMILES: CCOC(=O)N1CCCC(N2CCC(C(=O)NCC3CC3)CC2)CC1]
Example 15
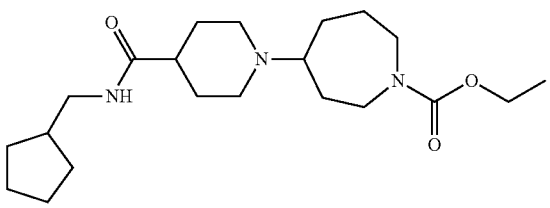 [SMILES: CCOC(=O)N1CCCC(N2CCC(C(=O)NCC3CCCC3)CC2)CC1]
Example 16
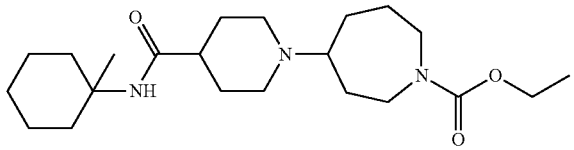 [SMILES: CCOC(=O)N1CCCC(N2CCC(C(=O)NC3(C)CCCCC3)CC2)CC1]
Example 17
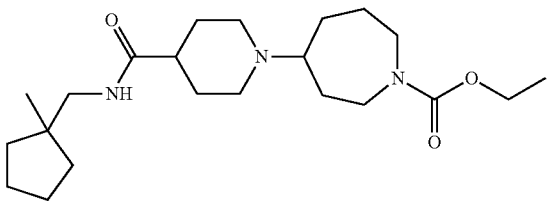 [SMILES: CCOC(=O)N1CCCC(N2CCC(C(=O)NCC3(C)CCCC3)CC2)CC1]
Example 18
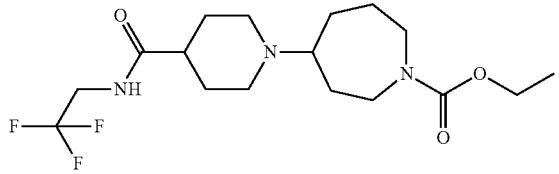 [SMILES: CCOC(=O)N1CCCC(N2CCC(C(=O)NCC(F)(F)F)CC2)CC1]
Example 19
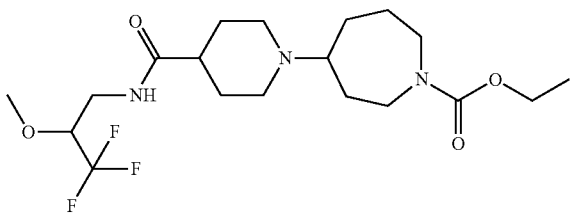 [SMILES: CCOC(=O)N1CCCC(N2CCC(C(=O)NCC(OC)C(F)(F)F)CC2)CC1]
Example 20

TABLE 1-continued
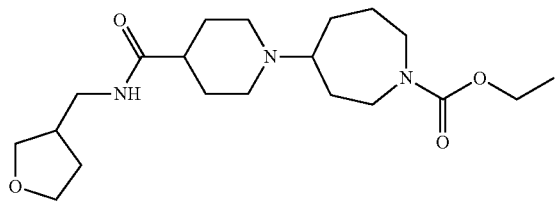 [SMILES: CCOC(=O)N1CCCC(N2CCC(C(=O)NCC3CCOC3)CC2)CC1] Example 21
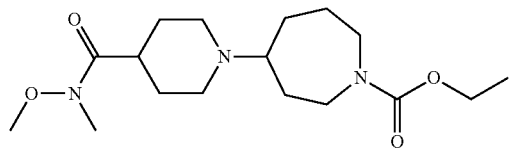 [SMILES: CCOC(=O)N1CCCC(N2CCC(C(=O)N(C)OC)CC2)CC1] Example 22
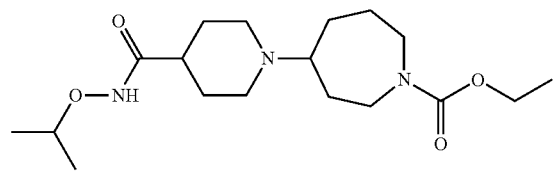 [SMILES: CCOC(=O)N1CCCC(N2CCC(C(=O)NOC(C)C)CC2)CC1] Example 23
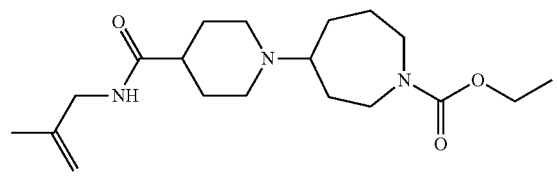 [SMILES: C=C(C)CNC(=O)C1CCN(C2CCCN(C(=O)OCC)CC2)CC1] Example 24
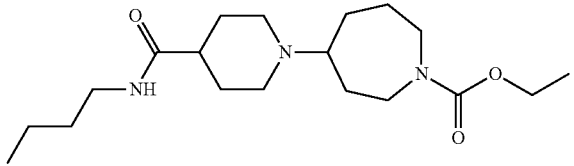 [SMILES: CCCCNC(=O)C1CCN(C2CCCN(C(=O)OCC)CC2)CC1] Example 25
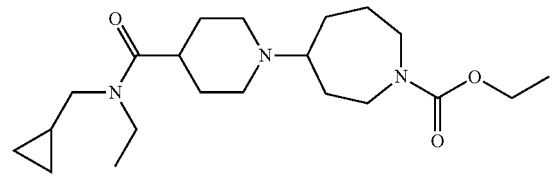 [SMILES: CCOC(=O)N1CCCC(N2CCC(C(=O)N(CC)CC3CC3)CC2)CC1] Example 26
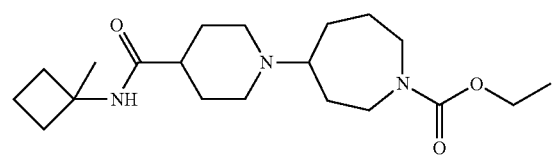 Example 27
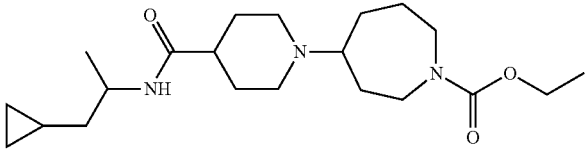 [SMILES: CCOC(=O)N1CCCC(N2CCC(C(=O)NC(C)CC3CC3)CC2)CC1] Example 28
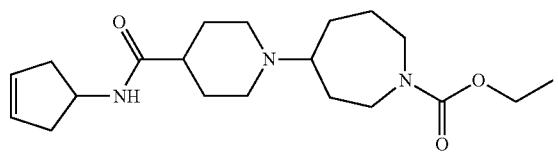 Example 29

TABLE 1-continued
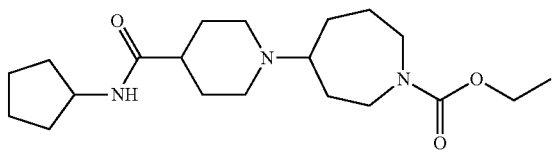 [SMILES: CCOC(=O)N1CCCC(N2CCC(C(=O)NC3CC=CC3)CC2)CC1] Example 30
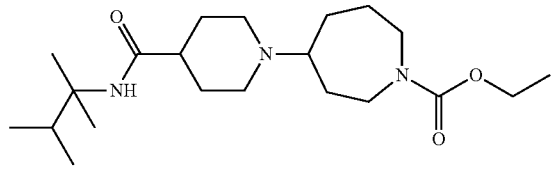 [SMILES: CCOC(=O)N1CCCC(N2CCC(C(=O)NC(C)(C)C(C)C)CC2)CC1] Example 31
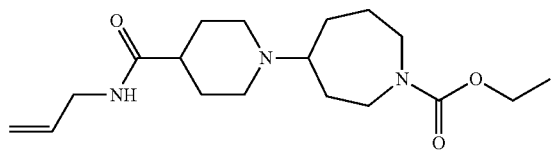 [SMILES: C=CCNC(=O)C1CCN(C2CCCN(C(=O)OCC)CC2)CC1] Example 32
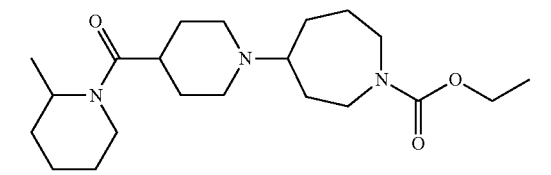 [SMILES: CCOC(=O)N1CCCC(N2CCC(C(=O)N3CCCCC3C)CC2)CC1] Example 33
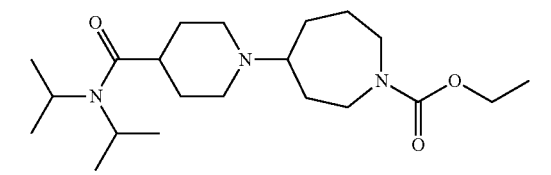 [SMILES: CCOC(=O)N1CCCC(N2CCC(C(=O)N(C(C)C)C(C)C)CC2)CC1] Example 34
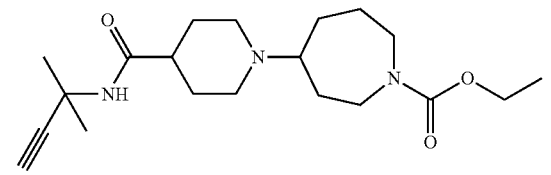 [SMILES: C#CC(C)(C)NC(=O)C1CCN(C2CCCN(C(=O)OCC)CC2)CC1] Example 35
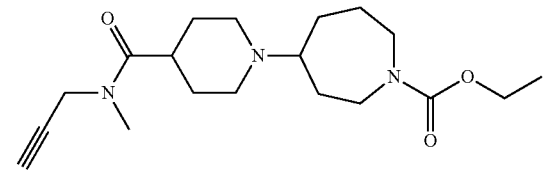 [SMILES: C#CCN(C)C(=O)C1CCN(C2CCCN(C(=O)OCC)CC2)CC1] Example 36
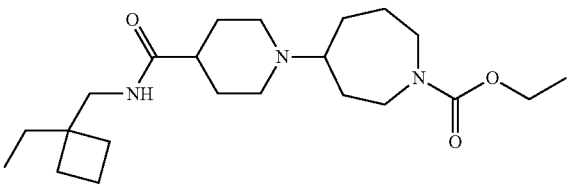 [SMILES: CCOC(=O)N1CCCC(N2CCC(C(=O)NCC3(CC)CCC3)CC2)CC1] Example 37
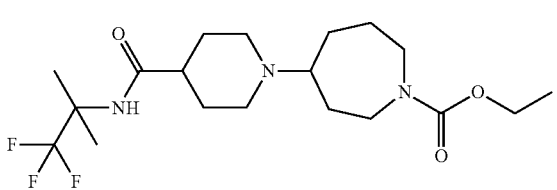 [SMILES: CCOC(=O)N1CCCC(N2CCC(C(=O)NC(C)(C)C(F)(F)F)CC2)CC1] Example 38

TABLE 1-continued
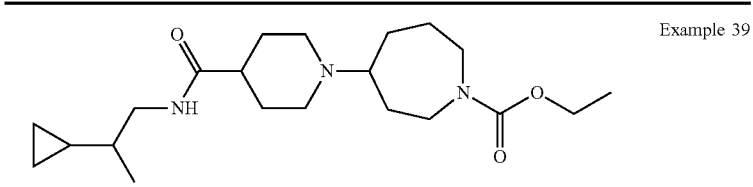
Example 39
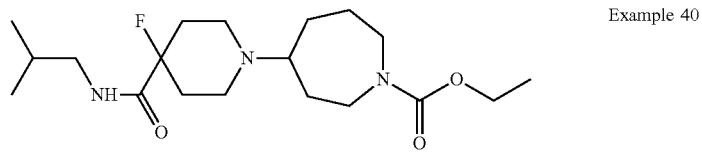
Example 40
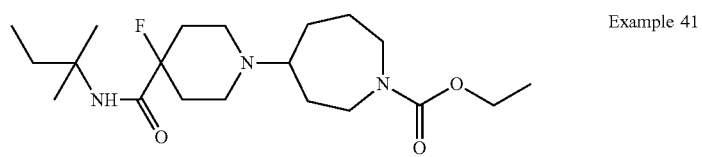
Example 41
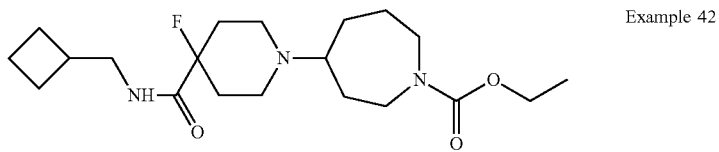
Example 42
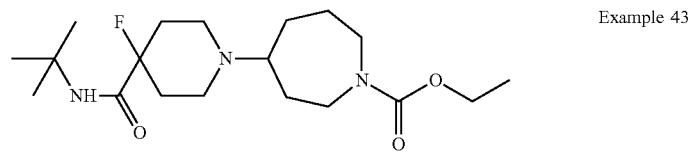
Example 43
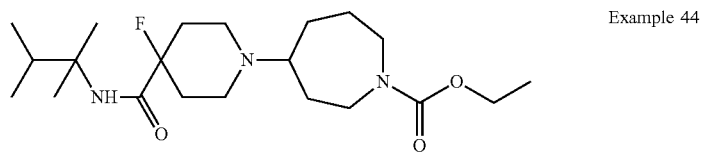
Example 44
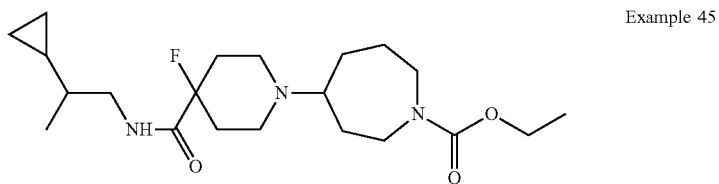
Example 45
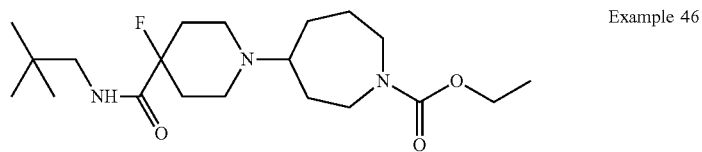
Example 46
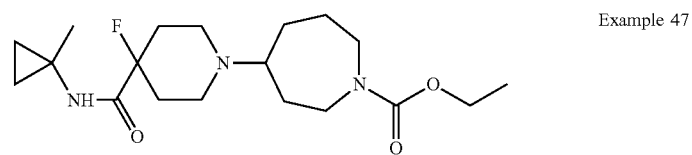
Example 47

TABLE 1-continued
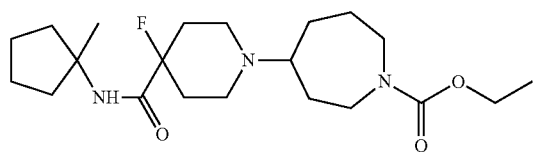 [SMILES: CCOC(=O)N1CCCC(N2CCC(F)(C(=O)NC3(C)CCCC3)CC2)CC1] Example 48
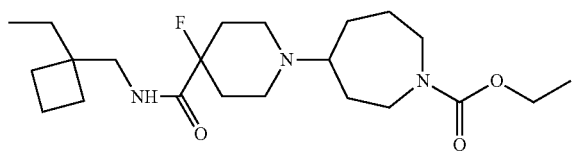 [SMILES: CCOC(=O)N1CCCC(N2CCC(F)(C(=O)NCC3(CC)CCC3)CC2)CC1] Example 49
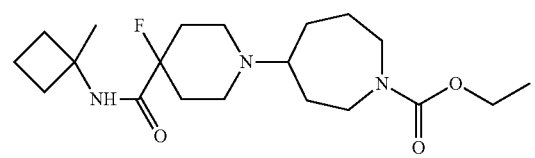 Example 50
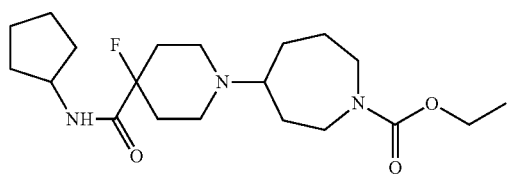 [SMILES: CCOC(=O)N1CCCC(N2CCC(F)(C(=O)NC3CCCC3)CC2)CC1] Example 51
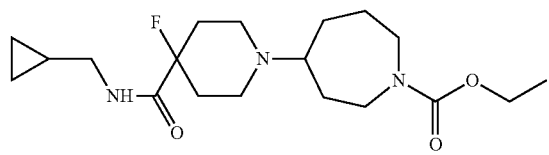 [SMILES: CCOC(=O)N1CCCC(N2CCC(F)(C(=O)NCC3CC3)CC2)CC1] Example 52
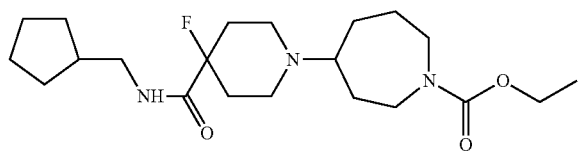 [SMILES: CCOC(=O)N1CCCC(N2CCC(F)(C(=O)NCC3CCCC3)CC2)CC1] Example 53
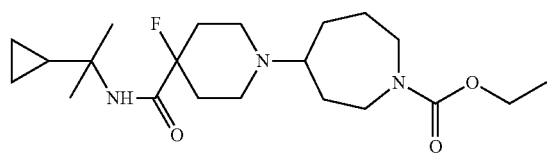 [SMILES: CCOC(=O)N1CCCC(N2CCC(F)(C(=O)NC(C)(C)C3CC3)CC2)CC1] Example 54
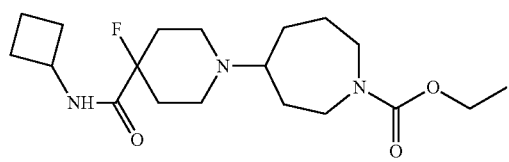 [SMILES: CCOC(=O)N1CCCC(N2CCC(F)(C(=O)NC3CCC3)CC2)CC1] Example 55
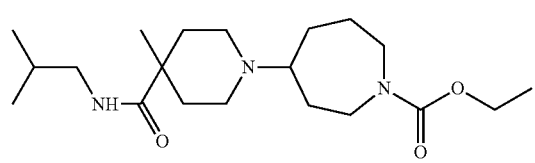 [SMILES: CCOC(=O)N1CCCC(N2CCC(C)(C(=O)NCC(C)C)CC2)CC1] Example 56

TABLE 1-continued
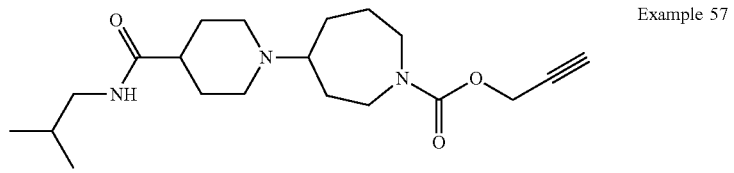
Example 57
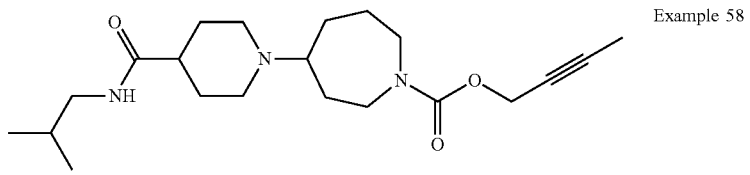
Example 58
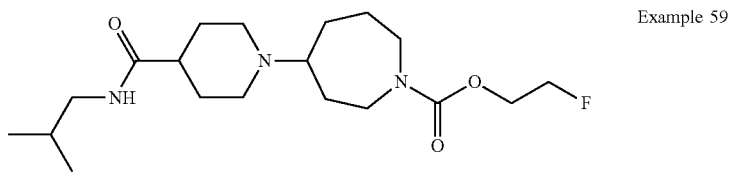
Example 59
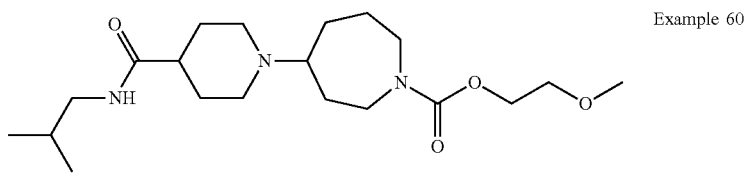
Example 60
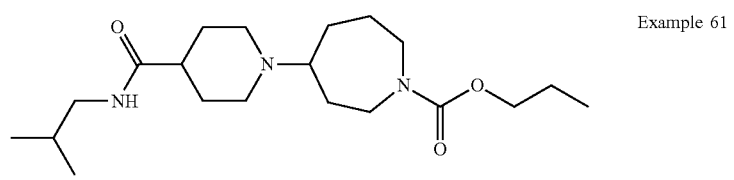
Example 61
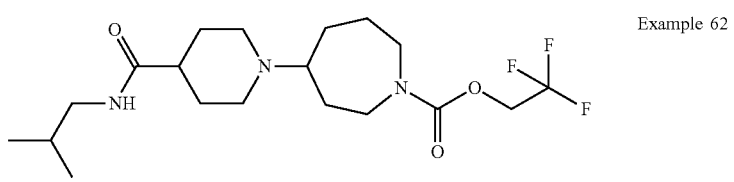
Example 62
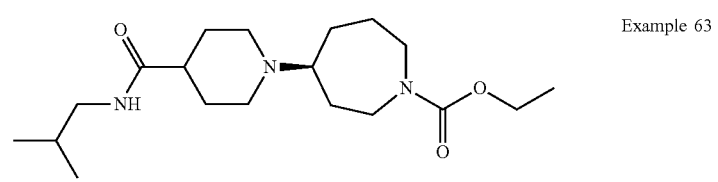
Example 63
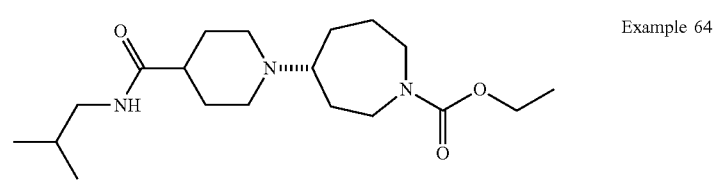
Example 64
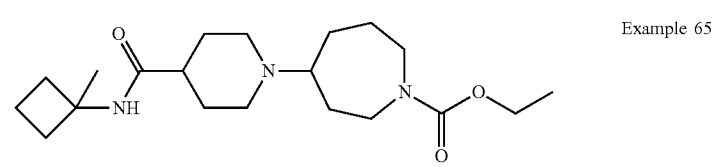
Example 65

TABLE 1-continued
| | |
|---|---|
| 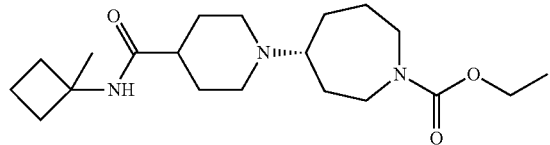 [SMILES: CCOC(=O)N1CCC[C@@H](N2CCC(C(=O)NC3(C)CCC3)CC2)CC1] | Example 66 |
| 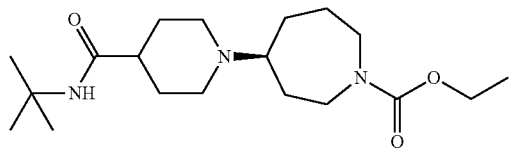 [SMILES: CCOC(=O)N1CCC[C@H](N2CCC(C(=O)NC(C)(C)C)CC2)CC1] | Example 67 |
| 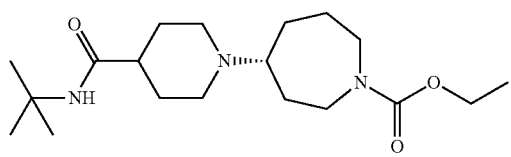 [SMILES: CCOC(=O)N1CCC[C@@H](N2CCC(C(=O)NC(C)(C)C)CC2)CC1] | Example 68 |
| 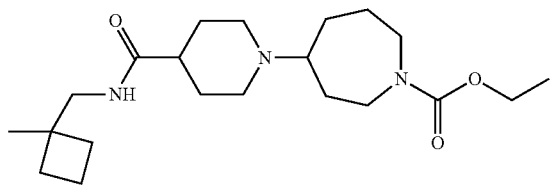 [SMILES: CCOC(=O)N1CCCC(N2CCC(C(=O)NCC3(C)CCC3)CC2)CC1] | Example 69 |
| 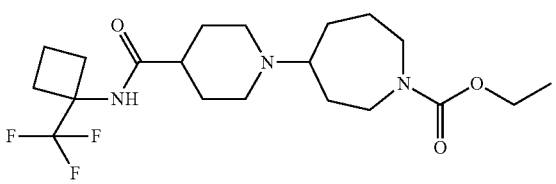 [SMILES: CCOC(=O)N1CCCC(N2CCC(C(=O)NC3(C(F)(F)F)CCC3)CC2)CC1] | Example 70 |
| 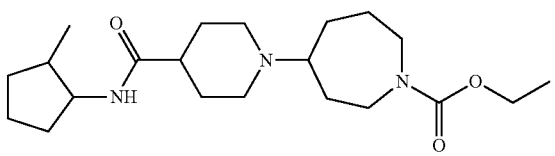 [SMILES: CCOC(=O)N1CCCC(N2CCC(C(=O)NC3CCCC3C)CC2)CC1] | Example 71 |
| 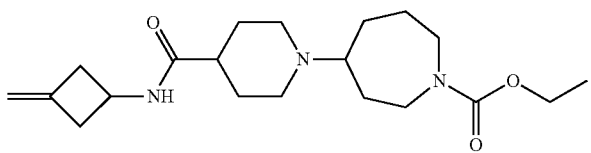 [SMILES: C=C1CC(NC(=O)C2CCN(C3CCCN(C(=O)OCC)CC3)CC2)C1] | Example 72 |
| 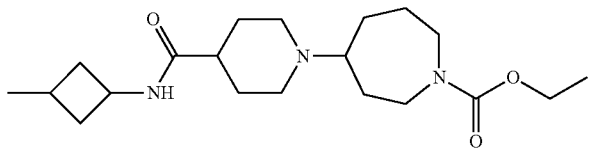 [SMILES: CCOC(=O)N1CCCC(N2CCC(C(=O)NC3CC(C)C3)CC2)CC1] | Example 73 |
| 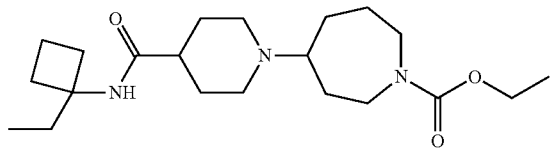 [SMILES: CCOC(=O)N1CCCC(N2CCC(C(=O)NC3(CC)CCC3)CC2)CC1] | Example 74 |

TABLE 1-continued

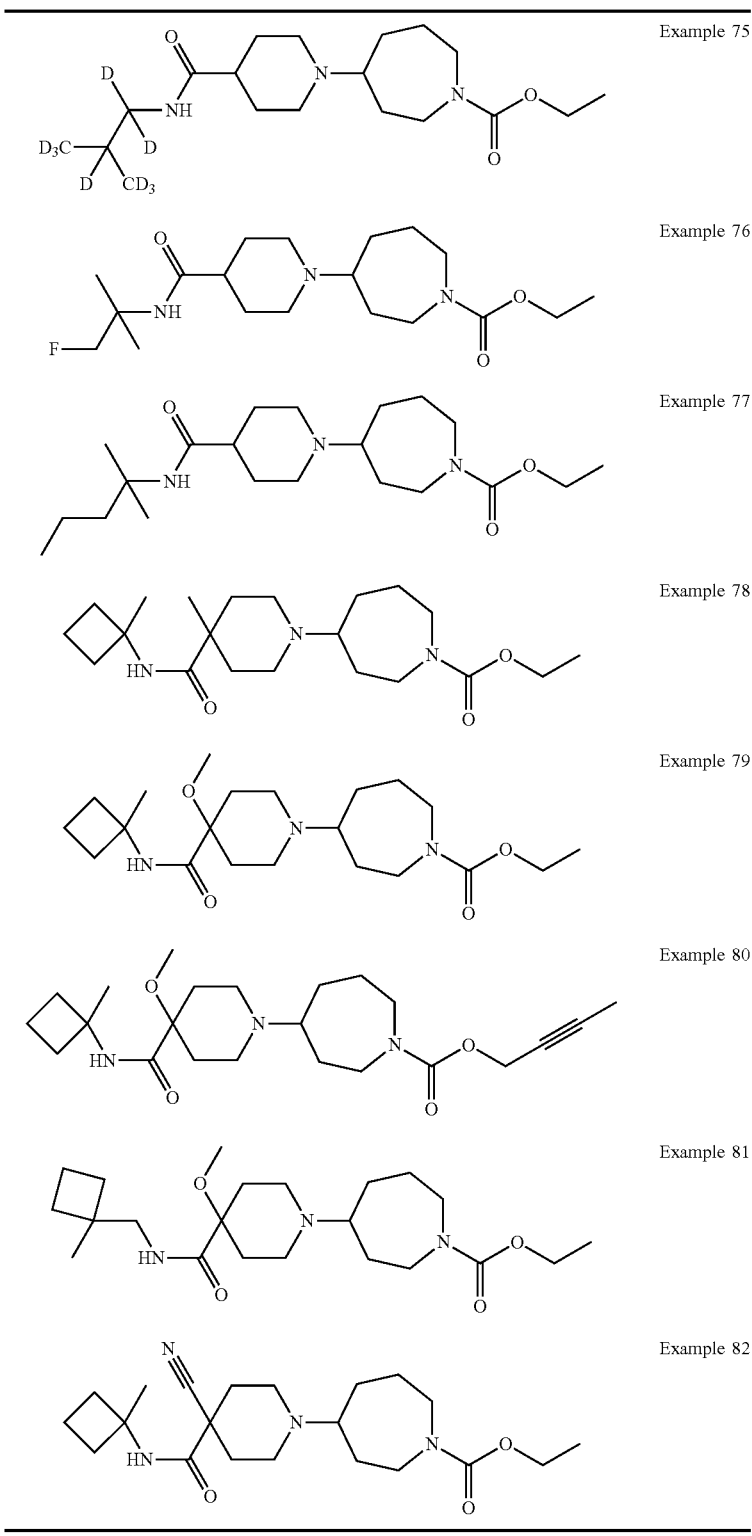

| | |
|---|---|
| | Example 75 |
| | Example 76 |
| | Example 77 |
| | Example 78 |
| | Example 79 |
| | Example 80 |
| | Example 81 |
| | Example 82 |

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. ($\delta$)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and the silica gel F254 as a stationary phase from Merck. Microwave-mediated reactions were performed in Biotage Initiator or CEM Discover microwave reactors.

Mass spectroscopy was carried out on Shimadzu LC-2010 EV, Waters ZQ-2000, UPLC-Mass SQD-3100 or Applied Biosystem API-2000 spectrometers using electrospray conditions as specified for each compound in the detailed experimental section.

Preparative HPLC was typically carried out under the following conditions, (Waters HPLC): Column: XSelect CSH Prep C-18, 19×50 mm, 5 µm; Mobile phase: Gradients of water and MeCN (each containing 0.1% Formic Acid); gradient 5% MeCN in 0.1 HCOOH in water (30 sec), 5% to 40% (over 7 min) then 95% MeCN in 0.1 HCOOH in water (1 min) then 5% MeCN in 0.1 HCOOH in water (1.5 min) at 28 mL/min.

LCMS experiments were typically carried out using electrospray conditions as specified for each compound under the following conditions:

Method A and B

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; radient [time (min)/solvent D in C (%)]: Method A: 0.00/2, 0.10/2, 2.50/95, 3.50/95, 3.55/2, 4.00/2 or Method B: 0.00/2, 0.10/2, 8.40/95, 9.40/95, 9.50/2, 10.00/2; Solvents: solvent C=2.5 L H$_2$O+2.5 mL ammonia solution; solvent D=2.5 L MeCN+135 mL H$_2$O+2.5 mL ammonia solution); Injection volume 3 uL; UV detection 230 to 400 nM; column temperature 45° C.; Flow rate 1.5 mL/min.

Method C

Instrument: Agilent 1200 LCMS. Column: Agilent Zorbax Extend RRHT, 1.8 µm, 4.6×30 mm. Detection wavelength: 254 nm. Gradient [time (min)/solvent B in A (%), flow rate]: 0.00/5 (2.5 mL/min), 3.00/95 (2.5 mL/min), 3.01/95 (4.5 mL/min), 3.50/95 (4.5 mL/min), 3.60/5 (3.5 mL/min), 3.90/95 (3.5 mL/min), 4.00/5 (2.5 mL/min) (solvent A: water with 0.1% formic acid; solvent B: MeCN with 0.1% formic acid).

Method D

Instrument: LCMS (Agilent 1200-6110) with UV and ELSD detector at 40° C. using waters X-Bridge C18 (4.6 mm*50 mm, 3.5 µm) and using water (0.05% TFA) and acetonitrile (0.05% TFA) as the mobile phase. The eluent gradient program was MECN (0.05% TFA) from 5% to 100% for 1.6 min and 100% MECN (0.05% TFA) for 1.4 min. The flow rate was 2.0 mL/min.

Method E

Instrument: LCMS (Agilent 1200-6110) with UV and ELSD detector at 40° C. using waters X-Bridge C18 (4.6 mm*50 mm, 3.5 µm) and using water (0.05% TFA) and acetonitrile (0.05% TFA) as the mobile phase. The eluent gradient program was MECN (0.05% TFA) from 5% to 100% for 5 min and 100% MeCN (0.05% TFA) for 1.0 min. The flow rate was 2.0 mL/min.

LCMS data in the experimental section are given in the format: Mass ion, retention time, approximate purity.

ABBREVIATIONS d=day(s)
DCE=dichloroethane
DCM=dichloromethane
DMF=dimethylformamide
DMSO=dimethylsulfoxide
ESI=electro spray ionisation
EtOAc=ethyl acetate
h=hour(s)
HATU=2-(7-Aza-1H-benzotriazole-1-yl)-1,1,3,3-tetramethyluronium hexafluorophosphate
HPLC=high performance liquid chromatography
LC=liquid chromatography
MeCN=acetonitrile
min=minute(s)
MS=mass spectrometry
NMR=nuclear magnetic resonance
rt=room temperature
sat.=saturated
sol.=solution
STAB=sodium triacetoxyborohydride
THF=tetrahydrofuran
TLC=thin layer chromatography Prefixes n-, s-, t- and tert- have their usual meanings: normal, secondary, iso, and tertiary.

Synthesis of Intermediates:

Intermediate 1

Preparation of 1'-(ethoxycarbonyl)-1,4'-bipiperidine-4-carboxylic acid

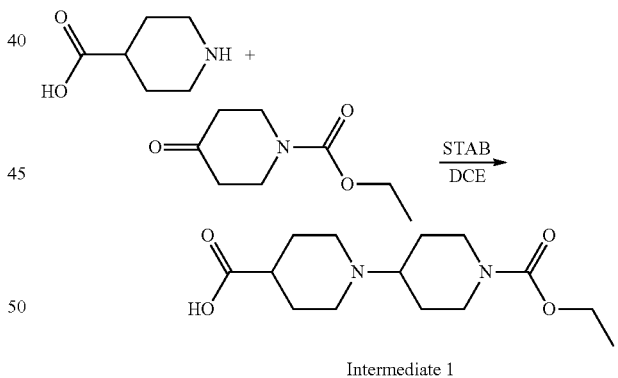

Intermediate 1

A solution of Isonipecotic acid (8.0 g, 61.0 mmol) in DCE (80 mL) was treated with acetic acid (10.7 mL, 185 mmol) and 1-carbethoxy-4-piperidone (12.7 g, 74.3 mmol). The reaction mixture was stirred for 1 hr at 40° C. Then STAB (29.2 g, 92.8 mmol) was added, the reaction mixture was stirred at 70° C. for 6 h, cooled to rt and the solvent was removed in vacuo. The residue was purified by column chromatography (gradient 0% to 50% MeOH in CHCl$_3$) to give 1'-(ethoxycarbonyl)-1,4'-bipiperidine-4-carboxylic acid (16.0 g, 92.2%), Intermediate 1, as an off white solid.

Mass spectroscopy: (ESI+ve) 285.1 [M+H]$^+$,
$^1$H NMR: (400 MHz, CD$_3$OD) δ1.26 (t, J=7.1, 3H), 1.61 (qd, J=12.3, 8.0, 2H), 1.83-2.17 (m, 5H), 2.32-2.44 (m, 1H), 2.75-3.14 (m, 4H), 3.23-3.28 (m, 2H), 3.35-3.50 (m, 2H), 4.12 (q, J=7.1, 2H), 4.26-4.30 (m, 2H), OH proton not observed.

Intermediate 2

Preparation of 1-(1-(ethoxycarbonyl)azepan-4-yl)piperidine-4-carboxylic acid

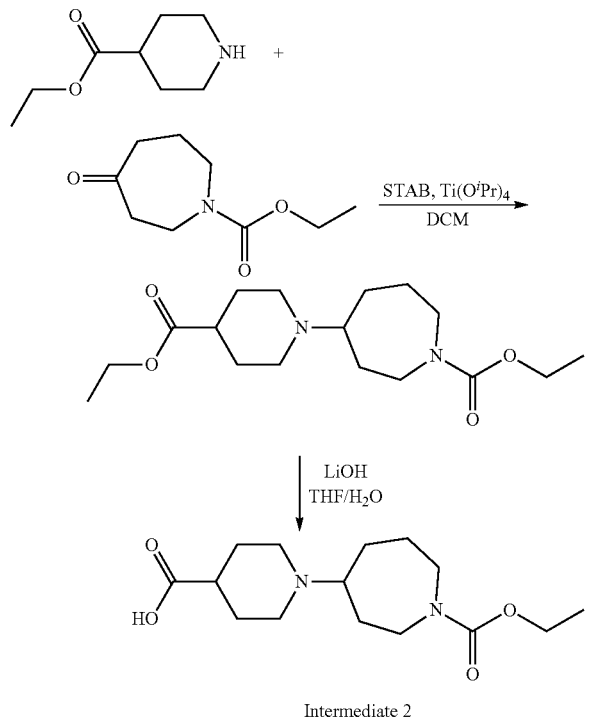

Intermediate 2

Ethyl isonipecotate (2.54 g, 2.50 mL, 16.2 mmol) and 4-oxoazepane-1-carboxylic acid ethyl ester (3.00 g, 16.2 mmol) were dissolved in DCM (100 mL) at rt and titanium isopropoxide (5.07 g, 5.40 mL, 17.8 mmol) was added. The reaction mixture was stirred at rt for 1 h. STAB (13.7 g, 32.4 mmol) and acetic acid (0.5 mL) were added and the reaction mixture was stirred at rt overnight under nitrogen. The reaction mixture was quenched with the addition of water (5 mL) and stirred for 5 minutes. The reaction mixture was diluted with DCM and filtered through a pad of celite. The filtrate was washed with sat. NaHCO₃ sol., sat. NaCl sol. and dried over MgSO₄. The solvents were removed in vacuo, and the residue was purified by column chromatography (normal phase, [Biotage SNAP cartridge KP-sil 50 g, 40-63 μm, 60 Å, 50 mL per min, gradient 2% to 4% MeOH in DCM]) to give ethyl 4-[4-(ethoxycarbonyl)piperidin-1-yl]azepane-1-carboxylate (2.56 g, 48%) as a pale yellow oil.

LCMS (Method A): m/z 327 (M+H)⁺ (ES⁺), at 1.68 min, UV inactive

¹H NMR: (400 MHz, DMSO-d₆) δ: 1.17 (t, J=7.0, 6H), 1.49-1.55 (m, 6H), 1.75-1.78 (m, 5H), 2.14-2.23 (m, 1H), 2.37 (t, J=9.1, 1H), 2.64-2.72 (m, 2H), 3.18-3.24 (m, 2H), 3.41-3.44 (m, 2H), 3.61-3.70 (m, 1H), 3.99-4.08 (m, 4H)

Ethyl 4-[4-(ethoxycarbonyl)piperidin-1-yl]azepane-1-carboxylate (1.10 g, 3.4 mmol) was dissolved in THF (60 mL) at rt and 1M LiOH sol. (10 mL) was added. The reaction mixture was stirred at rt for 5d. The pH was carefully adjusted to pH 6 by addition of concentrated hydrochloric acid, the solvents were removed in vacuo, to give 1-(1-(ethoxycarbonyl)azepan-4-yl)piperidine-4-carboxylic acid (1.5 g) as a viscous pale yellow oil, Intermediate 2, which was used crude in subsequent reactions.

LCMS (Method A): m/z 299 (M+H)⁺ (ES⁺), at 0.12 min, UV inactive

¹H NMR: (400 MHz, CD₃OD) δ: 1.22-1.32 (m, 3H), 1.60-2.38 (m, 11H), 2.08-2.22 (m, 1H), 3.13-3.26 (m, 2H), 3.33-3.51 (m, 2H), 3.52-3.76 (m, 2H), 4.08-4.18 (m, 2H), OH proton not observed.

Intermediate 3

Preparation of 1-[1-(ethoxycarbonyl)azepan-4-yl]-4-fluoropiperidine-4-carboxylic acid

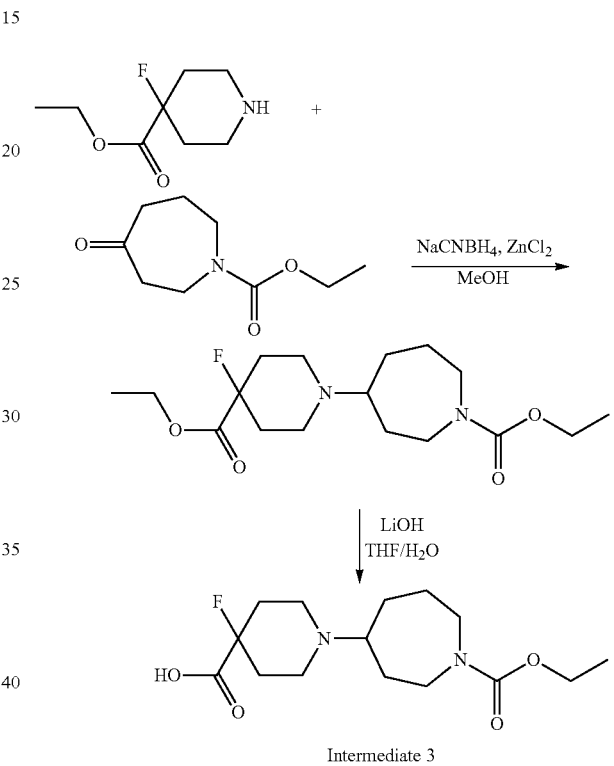

Intermediate 3

Ethyl 4-fluoropiperidine-4-carboxylate hydrochloride (3.00 g, 14.2 mmol) was dissolved in methanol (20 mL) and treated with K₂CO₃ (1.95 g, 14.2 mmol) in a minimum of water to de-salt. Reaction mixture was concentrated in vacuo and azeotroped to dryness with toluene. The residue and 4-oxoazepane-1-carboxylic acid ethyl ester (2.62 g, 14.2 mmol) were dissolved in methanol (50 mL) and zinc chloride (7.23 g, 56.7 mmol) was added. The reaction mixture was stirred at 50° C., under a nitrogen atmosphere, for 2 h then cooled to rt. NaCNBH₄ (1.78 g, 28.4 mmol) was added and the reaction mixture was stirred at 50° C. overnight under nitrogen. The reaction mixture was cooled to rt and the solvents were removed in vacuo, the residue was diluted with DCM and treated with sat. NaHCO₃ sol., the resulting heterogeneous mixture was filtered through a celite pad and the filtrate was washed with sat. NaHCO₃ sol., sat. NaCl sol. and dried over MgSO₄. The solvents were removed in vacuo, and the residue was purified by column chromatography (normal phase, [Biotage SNAP cartridge KP-sil 50 g, 40-63 μm, 60 Å, 50 mL per min, gradient 0% to 4% MeOH in DCM]) to give ethyl 4-[4-fluoro-4-(ethoxycarbonyl)piperidin-1-yl]azepane-1-carboxylate (2.26 g, 46%) as a colourless oil.

LCMS (Method A): m/z 331 (M+H)⁺ (ES⁺), at 1.84 min, UV inactive

¹H NMR: (400 MHz, CDCl₃) δ: 1.24-1.31 (m, 6H), 1.43-1.59 (m, 2H), 1.61-1.69 (m, 2H), 1.86-2.15 (m, 7H), 2.54-2.67 (m, 4H), 3.32-3.32 (m, 2H), 3.48-3.61 (m, 2H), 4.12 (q, J=6.8, 2H), 4.22 (q, J=7.2, 2H)

Ethyl 4-[4-fluoro-4-(ethoxycarbonyl)piperidin-1-yl]azepane-1-carboxylate (2.26 g, 6.85 mmol) was dissolved in THF (60 mL) at rt and 1M LiOH sol. (6.5 mL) was added. The reaction mixture was stirred at rt overnight. The pH was carefully adjusted to pH 6 by addition of concentrated hydrochloric acid, the solvents were removed in vacuo, to give 1-[1-(ethoxycarbonyl)azepan-4-yl]-4-fluoropiperidine-4-carboxylic acid (3.21 g) as a white waxy solid, Intermediate 3, which was used crude in subsequent reactions.

LCMS (Method A): m/z 317 (M+H)⁺ (ES⁺), at 0.24 min, UV inactive

Intermediate 4

Preparation of 1-[1-(ethoxycarbonyl)azepan-4-yl]-4-methylpiperidine-4-carboxylic acid

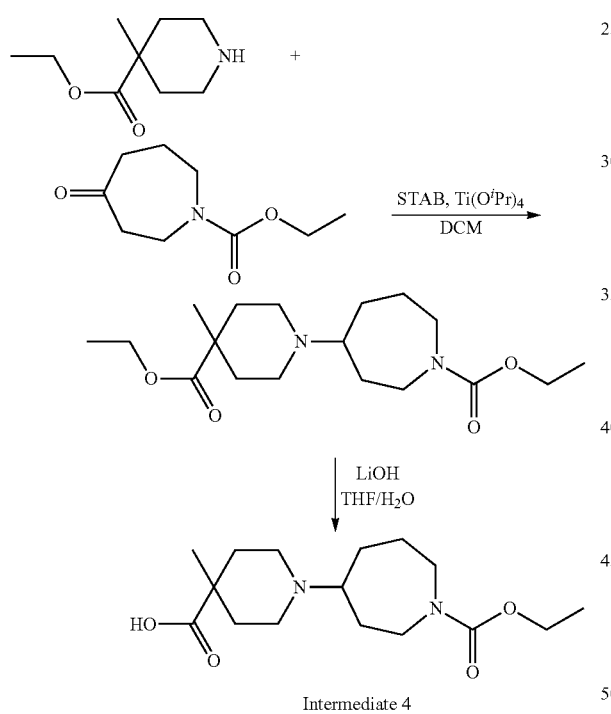

Intermediate 4

Ethyl-4-methylpiperidine-4-carboxylate hydrochloride (0.50 g, 2.42 mmol) was dissolved in methanol (10 mL) and treated with K₂CO₃ (0.33 g, 2.42 mmol) in a minimum of water to de-salt. Reaction mixture was concentrated in vacuo and azeotroped to dryness with toluene. The residue and 4-oxoazepane-1-carboxylic acid ethyl ester (0.45 g, 2.42 mmol) were dissolved in DCM (20 mL) at rt and titanium isopropoxide (0.76 g, 0.8 mL, 2.66 mmol) was added. The reaction mixture was stirred at rt for 5 h. STAB (2.05 g, 9.66 mmol) and acetic acid (0.3 mL) were added and the reaction mixture was stirred at rt overnight under nitrogen. The reaction mixture was quenched with the addition of water (5 mL) and stirred for 5 minutes. The reaction mixture was diluted with DCM and filtered through a pad of celite. The filtrate was washed with sat. NaHCO₃ sol., sat. NaCl sol. and dried over MgSO₄. The solvents were removed in vacuo, and the residue was purified by column chromatography (normal phase, [Biotage SNAP cartridge KP-sil 25 g, 40-63 μm, 60 Å, 25 mL per min, gradient 0% to 4% MeOH in DCM]) to give ethyl 4-[4-methyl-4-(ethoxycarbonyl)piperidin-1-yl]azepane-1-carboxylate (0.37 g, 45.0%) as a pale yellow oil.

LCMS (Method A): m/z 341 (M+H)⁺ (ES⁺), at 1.73 min, UV inactive

¹H NMR: (400 MHz, CDCl₃) δ: 1.16 (s, 3H), 1.23-1.27 (t, J=7.2, 6H), 1.40-1.89 (m, 5H), 1.92-1.93 (m, 4H), 2.11-2.62 (m, 6H), 3.25-3.51 (m, 4H), 4.09-4.17 (m, 4H).

Ethyl 4-[4-methyl-4-(ethoxycarbonyl)piperidin-1-yl]azepane-1-carboxylate (0.37 g, 1.09 mmol) was dissolved in THF (10 mL) at rt and 1M LiOH sol. (3.3 mL) was added. The reaction mixture was stirred at rt overnight. The pH was carefully adjusted to pH 6 by addition of concentrated hydrochloric acid, the solvents were removed in vacuo, to give 1-[1-(ethoxycarbonyl)azepan-4-yl]-4-methylpiperidine-4-carboxylic acid (0.66 g) as a viscous colourless oil, Intermediate 4, which was used crude in subsequent reactions.

LCMS (Method A): m/z 317 (M+H)⁺ (ES⁺), at 0.24 min, UV inactive

Intermediate 5

Preparation of 1-(azepan-4-yl)-N-(2-methylpropyl)piperidine-4-carboxamide TFA Salt

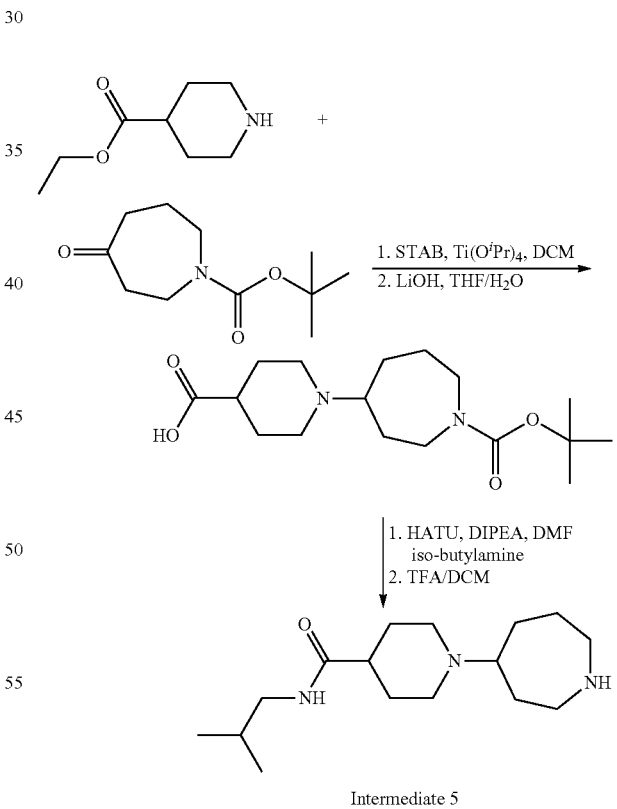

Intermediate 5

Ethyl isonipecotate (2.28 g, 2.25 mL, 14.5 mmol) and 4-oxoazepane-1-carboxylic acid tert-butyl ester (3.00 g, 14.5 mmol) were dissolved in DCM (60 mL) at rt and titanium isopropoxide (4.12 g, 4.40 mL, 14.5 mmol) was added. The reaction mixture was stirred at rt for 1 h. STAB (13.74 g, 32.4 mmol) and acetic acid (0.5 mL) were added and the reaction mixture was stirred at rt overnight under nitrogen. The reaction mixture was quenched with the addition of water (5 mL) and stirred for 5 minutes. The reaction mixture was diluted with DCM and filtered through a pad of celite. The filtrate was washed with sat. NaHCO$_3$ sol., sat. NaCl sol. and dried over MgSO$_4$. The solvents were removed in vacuo, and the residue was purified by column chromatography (normal phase, [Biotage SNAP cartridge KP-sil 50 g, 40-63 μm, 60 Å, 50 mL per min, gradient 0% to 4% MeOH in DCM]) to give ethyl 4-[4-(tert-butoxycarbonyl)piperidin-1-yl]azepane-1-carboxylate (2.61 g, 50.8%) as a pale yellow oil.

LCMS (Method A): m/z 355 (M+H)$^+$ (ES$^+$), at 1.93 min, UV inactive

Ethyl 4-[4-(tert-butoxycarbonyl)piperidin-1-yl]azepane-1-carboxylate (2.61 g, 7.4 mmol) was dissolved in THF (60 mL) at rt and 1M LiOH sol. (10 mL) was added. The reaction mixture was stirred at rt overnight. The solvents were removed in vacuo, to give 1-(1-(tert-butoxycarbonyl)azepan-4-yl)piperidine-4-carboxylic acid which was used crude is subsequent reaction.

LCMS (Method A): m/z 327 (M+H)$^+$ (ES$^+$), at 0.15 min, UV inactive

Residue was dissolved in DMF (30 mL) and isobutylamine (0.81 g, 1.1 mL, 11.0 mmol), HATU (4.20 g, 11.0 mmol) and DIPEA (4.76 g, 6.41 mL, 36.8 mmol) were added. The reaction mixture was stirred at rt for 48 h under nitrogen. The solvents were removed in vacuo, and the residue was partitioned between DCM and sat. NaHCO$_3$ sol., organic layer washed with sat. NaCl sol. and dried over MgSO$_4$. The solvents were removed in vacuo, and the residue was purified by column chromatography (normal phase, [Biotage SNAP cartridge KP-sil 50 g, 40-63 μm, 60 Å, 50 mL per min, gradient 0% to 10% MeOH in DCM]) to give tert-butyl 4-(4-((2-methylpropyl)carbamoyl)piperidin-1-yl)azepane-1-carboxylate (1.95 g, 69.4%) as a pale yellow oil.

LCMS (Method A): m/z 382 (M+H)$^+$ (ES$^+$), at 1.76 min, UV inactive tert-Butyl 4-(4-((2-methylpropyl)carbamoyl)piperidin-1-yl)azepane-1-carboxylate (1.95 g, 5.1 mmol) was dissolved in DCM (16 mL) and TFA (4 mL) was added. The reaction mixture was stirred at rt for 2 h under nitrogen, then the solvents were removed in vacuo, to give 1-(azepan-4-yl)-N-(2-methylpropyl)piperidine-4-carboxamide TFA salt (2.02 g), Intermediate 5, as a dark yellow oil which was used directly without further purification.

LCMS (Method A): m/z 282 (M+H)$^+$ (ES$^+$), at 1.34 min, UV inactive

Intermediate 6-(R) and 6-(S)

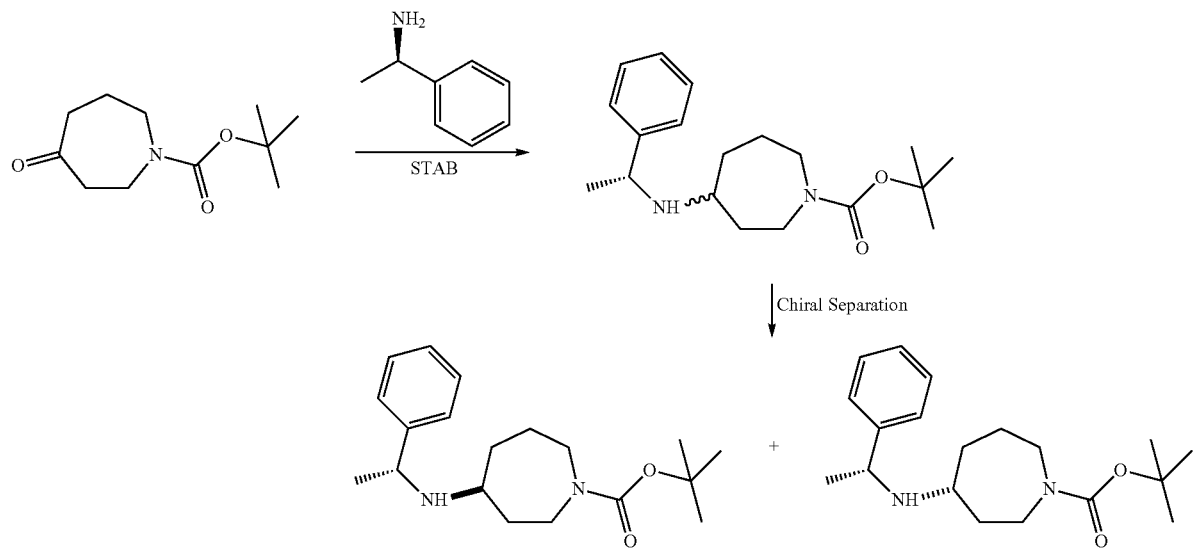

A mixture of 4-oxoazepane-1-carboxylic acid tert-butyl ester (90 g, 422 mmol) and (R)-1-phenylethanamine (56.4 g, 465 mmol) in THF (1000 mL) was stirred at rt for 15 min and STAB (107.4 g, 510 mmol) was added. The mixture was cooled to 0° C. in an ice bath, then acetic acid (26.7 g, 450 mmol) was added. The mixture was stirred overnight at rt then concentrated in vacuo, residue dissolved in DCM (800 mL) and washed with sat. NaHCO$_3$ sol. (2×300 mL), dried (Na$_2$SO$_4$). The solvents were removed in vacuo, and the residue was purified by column chromatography (gradient 0% to 3% MeOH in DCM) to give tert-butyl 4-{[(1R)-1-phenylethyl]amino}azepane-1-carboxylate (90 g, 67.0%) as a mixture of two diastereoisomers.

LCMS (Method D): m/z 319 (M+H)$^+$ (ES$^+$), at 1.25 min, 95%

70 g of this mixture was separated by chiral prep. HPLC [Instrument: Waters Thar-SFC 200 with UV detector GILSON UV-1(-151/152/155/156) at 35° C. using CHIRALPAK AY-H (2.0 cm I.D.×25 cm L. 5 μm) and using (Acetonitrile/isopropanol) (0.2% DEA)/CO2=1.2/4.8/94 (V/VV) as the mobile phase. Flow rate was 120 mL/min (all solvents were HPLC grade). The system back pressure was 100 bar. The SFC system was monitored at 214 nm.] to afford tert-butyl (4S)-4-{[(1R)-1-phenylethyl]amino}azepane-1-carboxylate (26 g, 24.9% yield) as a yellow oil and tert-butyl (4R)-4-{[(1R)-1-phenylethyl]amino}azepane-1-carboxylate (30 g, 28.6% yield) as a yellow oil.

tert-butyl (4S)-4-{[(1R)-1-phenylethyl]amino}azepane-1-carboxylate $^1$H NMR: (400 MHz, CDCl$_3$) δ: 1.26 (d, J=7.1, 3H), 1.33 (s, 9H), 1.34-1.43 (m, 3H), 1.72-1.97 (m, 3H), 2.34-2.39 (m, 1H), 3.01-3.45 (m, 4H), 3.80 (q, J=7.2, 1H), 7.15-7.25 (m, 5H), NH proton not observed $[\alpha]_D^{20}$=+57.0 (c=0.5 in MeOH)

The absolute configuration was determined by X-ray analysis of the p-bromobenzoate salt of tert-butyl (4S)-4-{[(1R)-1-phenylethyl]amino}azepane-1-carboxylate. (A. Alker et al. Bioorg. Med. Chem. Lett. 20 (2010) 4521-4525)

tert-butyl (4R)-4-{[(1R)-1-phenylethyl]amino}azepane-1-carboxylate $^1$H NMR: (400 MHz, CDCl$_3$) δ: 1.27 (d, J=7.0, 3H), 1.34 (s, 9H), 1.34-1.42 (m, 3H), 1.74-1.96 (m, 3H), 2.35-2.41 (m, 1H), 3.02-3.45 (m, 4H), 3.81 (q, J=7.1, 1H), 7.16-7.26 (m, 5H), NH proton not observed $[\alpha]_D^{20}$=−31.8 (c=0.5 in MeOH)

Intermediate 6-(S)

Preparation of tert-butyl (4S)-4-[4-(methoxycarbonyl)piperidin-1-yl]azepane-1-carboxylate

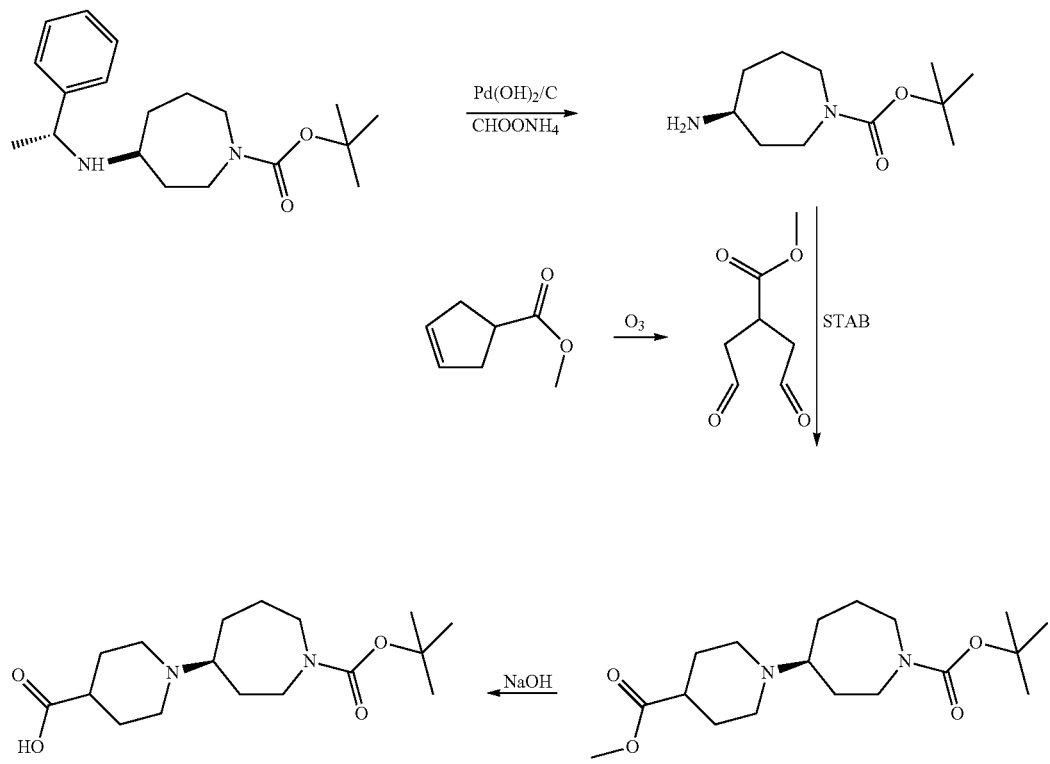

Intermediate 6-(S)

A suspension of Pd(OH)$_2$/C (10%, 550 mg), tert-butyl (4S)-4-{[(1R)-1-phenylethyl]amino}azepane-1-carboxylate (5.5 g, 17.3 mmol) and HCOONH$_4$ (3.3 g, 51.9 mmol) in MeOH (80 mL) was heated at reflux for 1.5 h. The reaction mixture was cooled to rt and filtered, the solvents of the filtrate were removed in vacuo. The residue was purified by column chromatography (gradient 0% to 10% MeOH in DCM) to give tert-butyl (4S)-4-aminoazepane-1-carboxylate (3.2 g, 87.3%).

LCMS (Method E): m/z 215 (M+H)$^+$ (ES$^+$), at 1.53 min, UV inactive $^1$H NMR: (400 MHz, CDCl$_3$) δ: 1.34-1.42 (m, 3H), 1.39 (s, 9H), 1.45-1.53 (m, 2H), 1.60-1.86 (m, 3H), 2.80-2.90 (m, 1H), 3.08-3.53 (m, 4H)

$[\alpha]_D^{20}$=+21.3 (c=1.0 in MeOH)

Methyl cyclopent-3-ene-1-carboxylate (4.42 g, 35 mmol) was dissolved in DCM/MeOH (160 mL, 3:1) and cooled to −78° C. Ozone was passed through the solution until a blue colour persisted. Excess ozone was purged from the reaction mixture with dry N$_2$. Dimethylsulfide (10 mL) was added and the reaction mixture was warmed to rt, the solvent was removed in vacuo. The residue was added to a solution of tert-butyl (4S)-4-aminoazepane-1-carboxylate (7.5 g, 35 mmol), STAB (18.57 g, 87.6 mmol), NEt$_3$ (4.26 g, 42.1 mmol) and acetic acid (1.8 mL) in DCE (200 mL). The mixture was stirred for 3 hours at rt and was then poured into aqueous Na$_2$CO$_3$ solution. The mixture was extracted with EtOAc (3×200 mL), the organic phase were washed with water (100 mL) and brine (100 mL), dried over Na$_2$SO$_4$. The solvent was removed in vacuo, and the residue was purified by column chromatography (gradient 0% to 25% EtOAc in Petroleum ether) to give tert-butyl (4S)-4-[4-(methoxycarbonyl)piperidin-1-yl]azepane-1-carboxylate (7.7 g, 64.6% yield) as a yellow oil.

LCMS (Method D): m/z 341 (M+H)$^+$ (ES$^+$), at 1.49 min, UV inactive tert-Butyl (4S)-4-[4-(methoxycarbonyl)piperidin-1-yl]azepane-1-carboxylate (7.7 g, 22.7 mmol) was dissolved in THF and water (60 mL, 1:1) and cooled to 0° C. NaOH (1.0 g, 24.5 mmol) was added and the reaction mixture was stirred at rt for 3 h. The organics solvents were removed in vacuo, and the aqueous phase was acidified with acetic acid to pH=3~4, then concentrated to dryness. The residue was suspended in CHCl$_3$ (40 mL) and filtered to remove inorganic salts. The filtrate was evaporated to dryness to afford 1-{(4S)-1-[(tert-butoxycarbonyl)carbonyl]azepan-4-yl}piperidine-4-carboxylic acid (6.2 g, 84% yield) as a yellow oil.

LCMS (Method D): m/z 327 (M+H)$^+$ (ES$^+$), at 1.35 min, UV inactive

¹H NMR: (400 MHz, DMSO-d₆) δ: 1.38 (s, 9H), 1.45-1.53 (m, 6H), 1.70-1.78 (m, 4H), 2.08-2.20 (m, 3H), 2.35-2.42 (m, 1H), 2.65-2.69 (m, 2H), 3.12-3.19 (m, 2H), 3.30-3.41 (m, 2H), 8.32 (br. s, 1H)

$[\alpha]_D^{20} = +11.0$ (c=1.8 in MeOH)

Intermediate 6-(R)

Preparation of tert-butyl (4R)-4-[4-(methoxycarbonyl)piperidin-1-yl]azepane-1-carboxylate

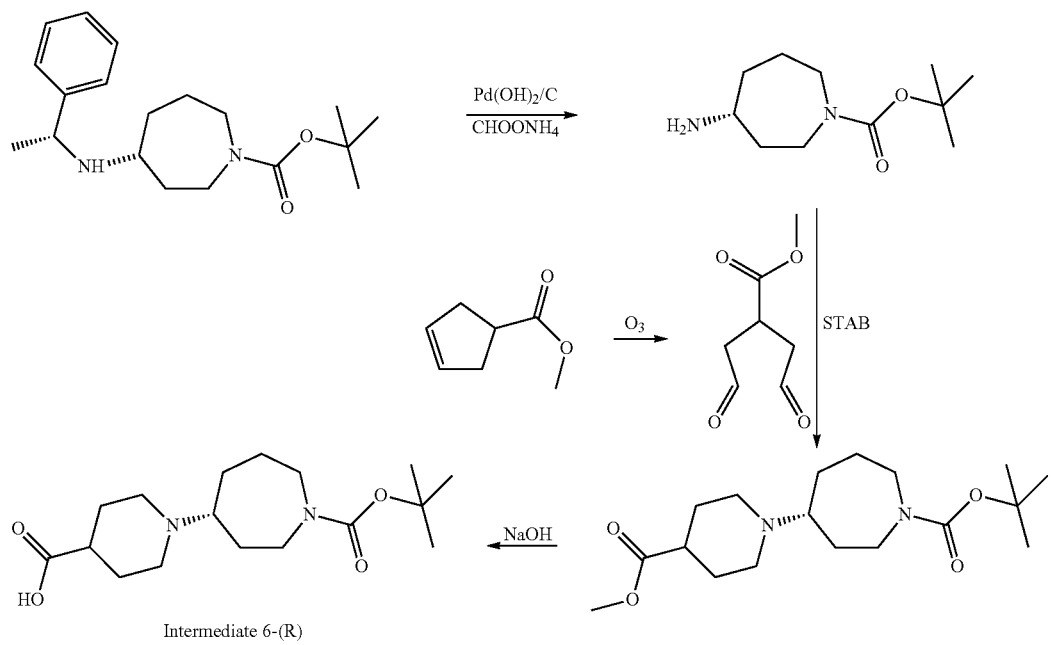

Intermediate 6-(R)

The title compound (6.1 g, 18.7 mmol) was prepared from tert-butyl (4R)-4-{[(1R)-1-phenylethyl]amino}azepane-1-carboxylate (5.5 g, 17.3 mmol) using the method outlined above for Intermediate 6-(S).

LCMS (Method D): m/z 327 (M+H)⁺ (ES⁺), at 1.35 min, UV inactive

¹H NMR: (400 MHz, DMSO-d₆) δ: 1.39 (s, 9H), 1.45-1.53 (m, 6H), 1.70-1.78 (m, 4H), 2.08-2.20 (m, 3H), 2.35-2.41 (m, 1H), 2.64-2.69 (m, 2H), 3.12-3.19 (m, 2H), 3.30-3.41 (m, 2H), 8.32 (br. s, 1H)

$[\alpha]_D^{20} = -10.7$ (c=2.0 in MeOH).

Intermediate 7

Preparation of 1-(azepan-4-yl)-4-methoxy-N-(1-methylcyclobutyl)piperidine-4-carboxamide TFA Salt

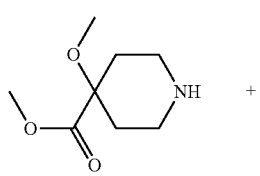

+

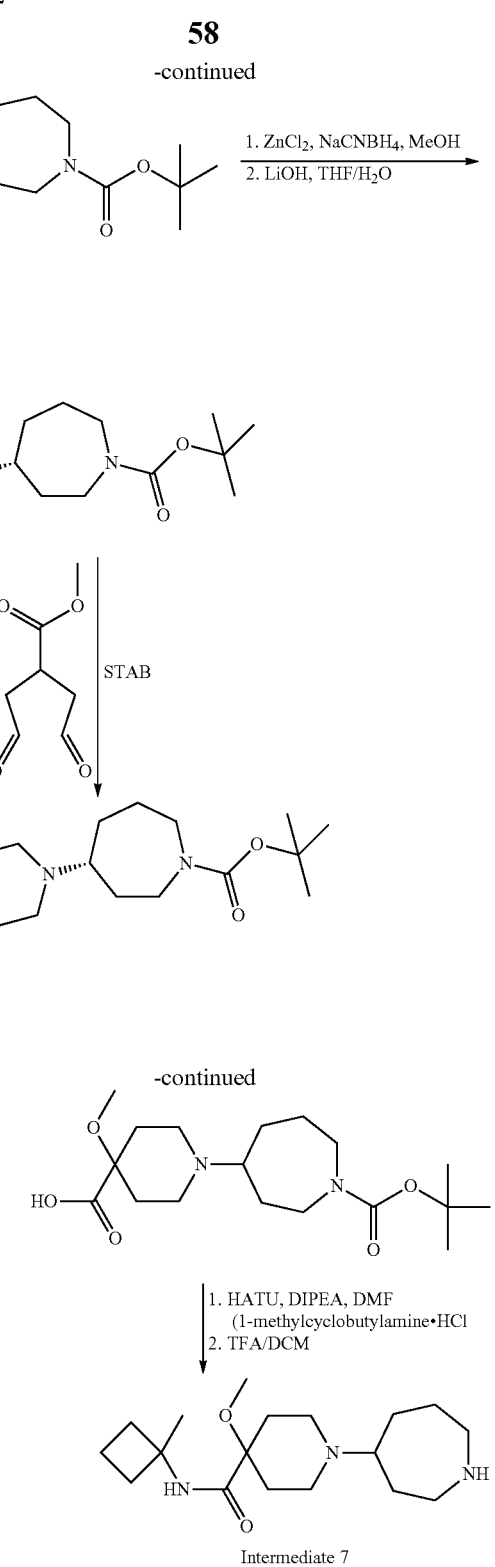

Intermediate 7

4-Methoxypiperidine-4-carboxylic acid methyl ester hydrochloride (0.50 g, 2.38 mmol) was dissolved in methanol (10 mL) and treated with K₂CO₃ (0.328 g, 2.38 mmol) in a minimum of water to de-salt. The reaction mixture was concentrated in vacuo and azeotroped to dryness with toluene. The residue and 4-oxoazepane-1-carboxylic acid tert-butyl ester (0.745 g, 2.38 mmol) were dissolved in methanol (20 mL) at rt and treated with zinc chloride (0.975 g, 7.15 mmol). The reaction mixture was stirred at 50° C. for 3 h. The solution was cooled to room temperature, sodium cyanoborohydride (0.299 g, 4.77 mmol) was added and the reaction mixture was stirred at 50° C. overnight under nitrogen. The solvents were removed in vacuo, and the residue was partitioned between DCM and sat. NaHCO₃ sol. The aqueous phase was extracted with DCM (2×20 mL). The organics were combined, washed with sat. NaCl sol. and dried by passing through a Biotage Phase Separator cartridge. The solvents were removed in vacuo and the residue was purified by column chromatography (normal phase, [Biotage SNAP cartridge KP-sil 25 g, 40-63 μm, 60 Å, 50 mL per min, gradient 1% to 10% MeOH in DCM]) to give tert-butyl 4-[4-methoxy-4-(methoxycarbonyl)piperidin-1-yl]azepane-1-carboxylate (0.163 g, 15.5%) as a colourless oil.

LCMS (Method A): m/z 371 (M+H)⁺ (ES⁺), at 1.72 min, UV inactive tert-butyl 4-[4-methoxy-4-(methoxycarbonyl)piperidin-1-yl]azepane-1-carboxylate (0.06 g, 0.17 mmol) was dissolved in THF (5 mL) at rt and 1M LiOH sol. (0.35 mL) was added. The reaction mixture was stirred at rt for 8 days. The pH was carefully adjusted to pH 6 by addition of concentrated hydrochloric acid, the solvents were removed in vacuo, to give 1-[1-(tert-butoxycarbonyl)azepan-4-yl]-4-methoxypiperidine-4-carboxylic acid which was used crude in subsequent reaction.

LCMS (Method A): m/z 357 (M+H)⁺ (ES⁺), at 0.24 min, UV inactive

1-[1-(tert-butoxycarbonyl)azepan-4-yl]-4-methoxypiperidine-4-carboxylic acid (0.163 g, 0.44 mmol) was dissolved in DMF (5 mL) and (1-methyl)cyclobutylamine hydrochloride (0.08 g, 0.66 mmol), HATU (0.25 g, 0.66 mmol) and DIPEA (0.284 g, 0.38 mL, 2.20 mmol) were added. The reaction mixture was stirred at rt overnight under nitrogen. The solvents were removed in vacuo, and the residue was partitioned between DCM and sat. NaHCO₃ sol., organic layer washed with sat. NaCl sol. and dried over MgSO₄. The solvents were removed in vacuo, and the residue was purified by column chromatography (normal phase, [Biotage SNAP cartridge KP-sil 25 g, 40-63 μm, 60 Å, 50 mL per min, gradient 1% to 6% MeOH in DCM]) to give tert-butyl 4-{4-methoxy-4-[(1-methylcyclobutyl)carbamoyl]piperidin-1-yl}azepane-1-carboxylate (0.025 g, 13.4%) as a pale yellow oil.

LCMS (Method A): m/z 424 (M+H)⁺ (ES⁺), at 1.88 min, UV inactive tert-butyl 4-{4-methoxy-4-[(1-methylcyclobutyl)carbamoyl]piperidin-1-yl}azepane-1-carboxylate (0.25 g, 0.06 mmol) was dissolved in DCM (4 mL) and TFA (1 mL) was added. The reaction mixture was stirred at rt overnight under nitrogen, then the solvents were removed in vacuo, to give 1-(azepan-4-yl)-4-methoxy-N-(1-methylcyclobutyl)piperidine-4-carboxamide TFA salt (0.26 g), Intermediate 7, as a dark yellow oil which was used directly without further purification.

LCMS (Method A): m/z 324 (M+H)⁺ (ES⁺), at 0.18 min, UV inactive

Intermediate 8

Preparation of 1-[1-(ethoxycarbonyl)azepan-4-yl]-4-methoxypiperidine-4-carboxylic acid

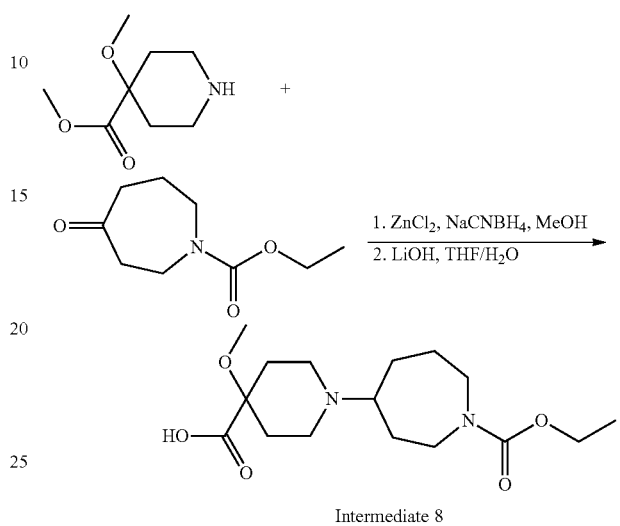

Intermediate 8

4-Methoxypiperidine-4-carboxylic acid methyl ester hydrochloride (0.50 g, 2.38 mmol) was dissolved in methanol (10 mL) and treated with K₂CO₃ (0.328 g, 2.38 mmol) in a minimum of water to de-salt. Reaction mixture was concentrated in vacuo and azeotroped to dryness with toluene. The residue and 4-oxoazepane-1-carboxylic acid ethyl ester (0.441 g, 2.38 mmol) were dissolved in methanol (20 mL) at rt and treated with zinc chloride (0.975 g, 7.15 mmol). The reaction mixture was stirred at 50° C. for 2 h. The solution was cooled to room temperature, sodium cyanoborohydride (0.299 g, 4.77 mmol) was added and the reaction mixture was stirred at 50° C. overnight under nitrogen. The solvents were removed in vacuo, and the residue was suspended between DCM and sat. NaHCO₃ sol. The turbid mixture, was passed through a pad of celite which was washed with DCM. The organics layers were combined, washed with sat. NaCl sol. and dried by passing through a Biotage Phase Separator cartridge. The solvents were removed in vacuo and the residue was purified by column chromatography (normal phase, [Biotage SNAP cartridge KP-sil 25 g, 40-63 μm, 60 Å, 50 mL per min, gradient 1% to 6% MeOH in DCM]) to give ethyl 4-[4-methoxy-4-(methoxycarbonyl)piperidin-1-yl]azepane-1-carboxylate (0.136 g, 16.4%) as a colourless oil.

LCMS (Method A): m/z 343 (M+H)⁺ (ES⁺), at 1.46 min, UV inactive

Ethyl 4-[4-methoxy-4-(methoxycarbonyl)piperidin-1-yl]azepane-1-carboxylate (0.136 g, 0.39 mmol) was dissolved in THF (5 mL) at rt and 1M LiOH sol. (0.4 mL) was added. The reaction mixture was stirred at rt for 2 days. The pH was carefully adjusted to pH 6 by addition of concentrated hydrochloric acid, the solvents were removed in vacuo, to give 1-[1-(ethoxycarbonyl)azepan-4-yl]-4-methoxypiperidine-4-carboxylic acid (0.131 g), Intermediate 8, as a yellow oil which was used directly without further purification.

LCMS (Method A): m/z 329 (M+H)⁺ (ES⁺), at 0.13 min, UV inactive

Intermediate 9

Preparation of 4-cyano-1-[1-(ethoxycarbonyl)azepan-4-yl]piperidine-4-carboxylic acid

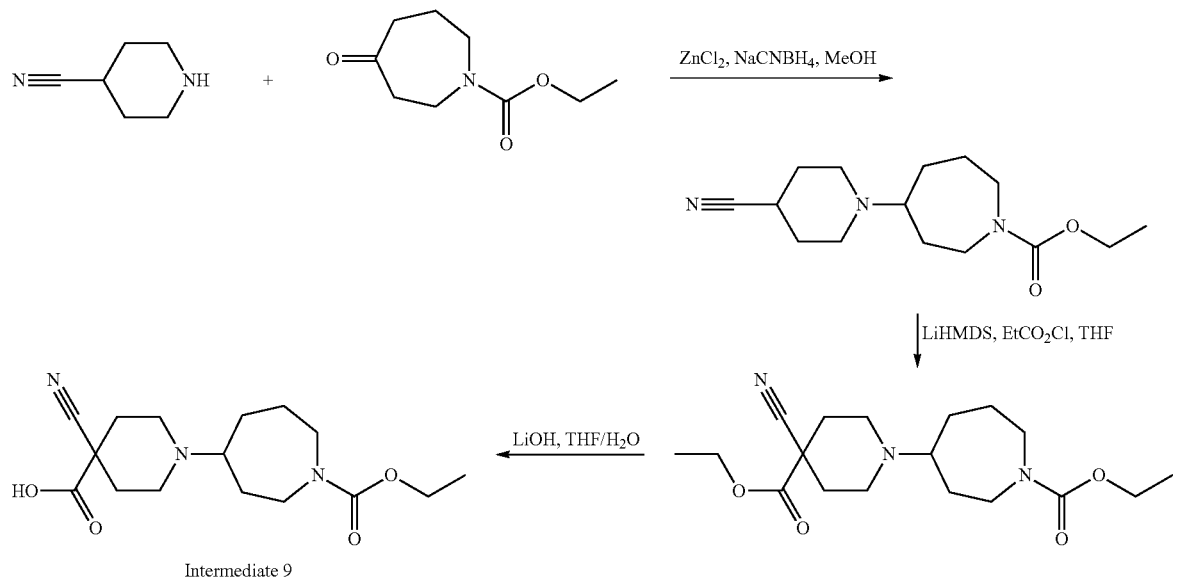

Intermediate 9

4-cyanopiperidine (0.40 g, 3.62 mmol) was dissolved in MeOH (15 mL), 4-oxoazepane-1-carboxylic acid ethyl ester (0.672 g, 3.62 mmol) and zinc chloride (1.98 g, 14.48 mmol) were added. The reaction mixture was heated for 2 h at 50° C. The solution was then cooled on ice and treated portionwise with sodium cyanoborohydride (0.456 g, 7.24 mmol) and reheated to 50° C. overnight. The reaction mixture was concentrated in vacuo to a white solid. This was dissolved in sat. NH$_4$Cl sol. and extracted with EtOAc (3×50 mL). The combined organics were washed with sat. NaCl sol., dried over MgSO$_4$, filtered and concentrated in vacuo. The residue was purified by column chromatography (normal phase, [Biotage SNAP cartridge KP-sit 25 g, 40-63 μm, 60 Å, 50 mL per min, gradient 0% to 4% MeOH in DCM]) to give ethyl 4-(4-cyanopiperidin-1-yl)azepane-1-carboxylate as an oil (0.090 g, 8.9%).

LCMS (Method A): m/z 280 (M+H)$^+$ (ES$^+$), at 1.67 min, UV inactive 1.0 M Lithium bis(trimethylsilyl)amide (4.48 mL, 7.17 mmol) was added to anhydrous THF (20 mL) under nitrogen and cooled to −78° C. The solution was treated drop wise with ethyl 4-(4-cyanopiperidin-1-yl)azepane-1-carboxylate (0.400 g, 1.43 mmol) as a solution in anhydrous THF (2 mL). The solution was stirred at −78° C. under nitrogen for 1 h, ethyl chloroformate (0.17 g, 1.57 mmol) was added drop wise. The solution was stirred at −78° C. for a further 2 h and then allowed to warm to rt overnight. The reaction mixture was quenched with the addition of water and the solvents were removed in vacuo. The residue was partitioned between DCM and sat. NaHCO$_3$ sol. The organic layer was washed with sat. NaCl sol. and dried by passing through a Biotage Phase Separator cartridge. The solvents were removed in vacuo and the residue was purified by column chromatography (normal phase, [Biotage SNAP cartridge KP-sil 10 g, 40-63 μm, 60 Å, 50 mL per min, gradient 2% to 4% MeOH in DCM]) to give ethyl 4-[4-cyano-4-(ethoxycarbonyl)piperidin-1-yl]azepane-1-carboxylate (0.067 g, 12.7%) as an amber oil.

LCMS (Method A): m/z 352 (M+H)$^+$ (ES$^+$), at 1.70 min, UV inactive

Ethyl 4-[4-cyano-4-(ethoxycarbonyl)piperidin-1-yl]azepane-1-carboxylate (0.067 g, 0.182 mmol) was dissolved in methanol (4 mL) at rt and 1M LiOH sol. (0.2 mL) was added. The reaction mixture was stirred at rt for 1.5 h. The pH was carefully adjusted to pH 6 by addition of concentrated hydrochloric acid, the solvents were removed in vacuo, to give 4-cyano-1-[1-(ethoxycarbonyl)azepan-4-yl]piperidine-4-carboxylic acid, (0.62 g), Intermediate 9, as a yellow oil which was used directly without further purification.

LCMS (Method A): m/z 324 (M+H)$^+$ (ES$^+$), at 0.10 min, UV inactive

Route a

Typical Procedure for the Preparation of Amides Via Schotten-Baumann Reaction, as Exemplified by the Preparation of Example 1, ethyl 4-(2-methylpropyl)-carbamoyl)-1,4′-bipiperidine-1′-carboxylate

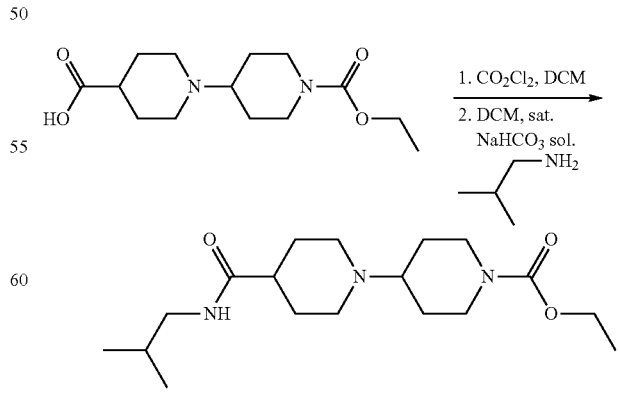

Example 1

1'-(ethoxycarbonyl)-1,4'-bipiperidine-4-carboxylic acid (0.60 g, 2.11 mmol) was dissolved in DCM (30 mL) the reaction mixture was cooled to 0° C. and oxalyl chloride (0.27 mL, 3.17 mmol) and DMF (0.1 mL) was added. The solution was stirred at rt for 2 h and then concentrated in vacuo. A portion of the residue (0.53 mmol) was dissolved in DCM (5 mL) and iso-butylamine (0.06 g, 0.08 mL, 0.79 mmol) and sat. NaHCO$_3$ sol. (5 ml) were added. The reaction mixture was stirred at rt overnight and then partitioned between DCM and sat.NaHCO$_3$ sol. The organic layer was washed with sat. NaCl sol. and dried (MgSO$_4$) and the solvent was removed in vacuo. The residue was purified by trituration from diethyl ether to give ethyl 4-(2-methylpropyl)carbamoyl)-1,4'-bipiperidine-1'-carboxylate (0.01 g, 9%) as a white solid.

Data in Table 2

Route b

Typical Procedure for the Preparation of Amides Via HATU Coupling, as Exemplified by the Preparation of Example 6, ethyl 4-(4-((2-methylpropyl)carbamoyl)piperidin-1-yl)azepane-1-carboxylate

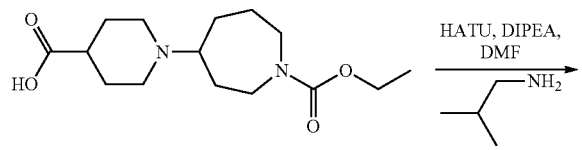

Example 6

1-(1-(ethoxycarbonyl)azepan-4-yl)piperidine-4-carboxylic acid (0.26 g assumed 0.89 mmol) was dissolved in DMF (4 mL) and isobutylamine (0.81 g, 1.1 mL, 11.0 mmol), HATU (0.51 g, 1.34 mmol) and DI PEA (0.46 g, 0.62 mL, 3.56 mmol) were added. The reaction mixture was stirred at rt overnight and the solvents were removed in vacuo. The residue was partitioned between DCM and sat. NaHCO$_3$ sol., the organic layer was washed with sat. NaCl sol. and dried (MgSO$_4$). The solvents were removed in vacuo, and the residue was purified by column chromatography (normal phase, [Biotage SNAP cartridge KP-sil 25 g, 40-63 µm, 60 Å, 25 mL per min, gradient 0% to 3% MeOH in DCM]) to give ethyl 4-(4-((2-methylpropyl)carbamoyl)piperidin-1-yl)azepane-1-carboxylate (17 mg, 2%) as a pale yellow gum.

Data in Table 2

Examples 7-16, 19 and 20 Purified by Prep HPLC

Route c

Typical Procedure for the Preparation of Amides Via Acid Chloride Coupling, as Exemplified by the Preparation of Example 27, ethyl 4-(4-((1-methylcyclobutyl)carbamoyl)piperidin-1-yl)azepane-1-carboxylate

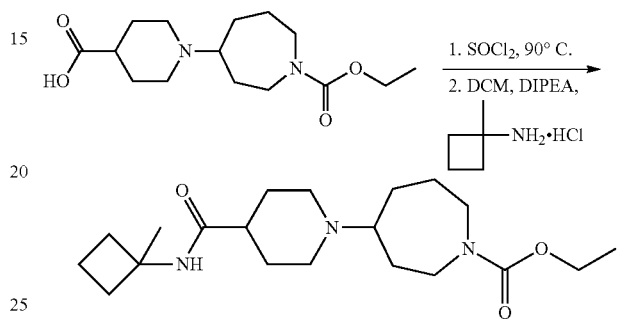

Example 27

Thionyl chloride (5 mL) was added to 1-(1-(ethoxycarbonyl)azepan-4-yl)piperidine-4-carboxylic acid (0.2 g, assume 0.34 mmol) and the reaction was stirred at 90° C. for 3 h. The reaction mixture was cooled to rt and concentrated in vacuo. The residue was dissolved in DCM (5 mL) and (1-methylcyclobutyl)amine.HCl (60.1 mg, 0.50 mmol) and DIPEA (0.23 ml, 1.34 mmol) were added, the reaction mixture was stirred at rt for 48 hours. The solvents were removed in vacuo, and the residue was purified by prep HPLC, the resulting product was loaded onto a SCX column (1 g) in 5% AcOH in MeOH. The column was washed with MeOH and then the product was eluted with 0.7 M ammonia in MeOH to give the titled compound (26 mg, 21%) as a white solid.

An alternate work up procedure would be: the reaction mixture was partitioned between DCM and sat. NaHCO$_3$ sol., the organic layer was washed with sat. NaCl sol. and dried over MgSO$_4$. The residue was purified by column chromatography (normal phase, [Biotage SNAP cartridge KP-sil 25 g, 40-63 µm, 60 Å, 12 mL per min, gradient 0% to 6% MeOH in DCM]) to give titled compound.

Data in Table 2

Route d

Typical Procedure for the Preparation of Amides via Acid Chloride Coupling, as Exemplified by the Preparation of Example 43, ethyl 4-(4-fluoro-4-((tert-butyl)carbamoyl)piperidin-1-yl)azepane-1-carboxylate

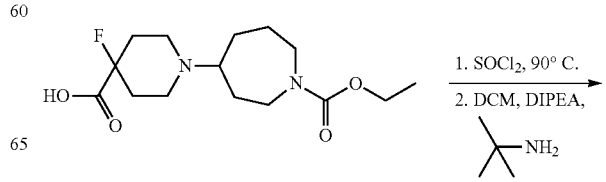

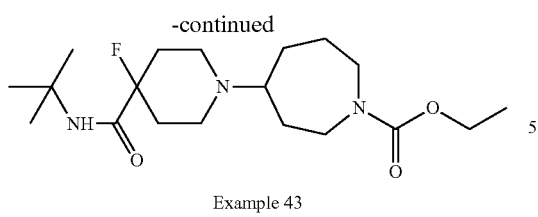

Example 43

Thionyl chloride (4 mL) was added to a solution of 1-[1-(ethoxycarbonyl)azepan-4-yl]-4-fluoropiperidine-4-carboxylic acid (1.24 g, assume 3.92 mmol) and the reaction was stirred at 90° C. for 3 h. The reaction mixture was cooled to rt and concentrated in vacuo. DCM (4 mL) was added to a portion of the residue (0.65 mmol) followed by tert-butylamine (0.14 mL, 1.31 mmol) and DIPEA (0.57 ml, 3.27 mmol), the reaction mixture was stirred at rt for 48 h. The solvents were removed in vacuo, and the residue was partitioned between DCM (50 mL) and sat. NaHCO$_3$ sol. (25 mL), organic layer washed with sat. NaCl sol. (25 mL) and dried over MgSO$_4$. The residue was purified by column chromatography (normal phase, [Biotage SNAP cartridge KP-sil 25 g, 40-63 μm, 60 Å, 25 mL per min, gradient 0% to 7% MeOH in DCM]) to give ethyl 4-(4-fluoro-4-((tert-butyl)carbamoyl)piperidin-1-yl)azepane-1-carboxylate (0.11 g, 46.8%) as a yellow oil.

Data in Table 2

Route e

Typical Procedure for the Preparation of Carbamates via Chloroformate Coupling, as Exemplified by the Preparation of Example 57, prop-2-yn-1-yl-4-(4-((2-methylpropyl)carbamoyl)piperidin-1-yl)azepane-1-carboxylate

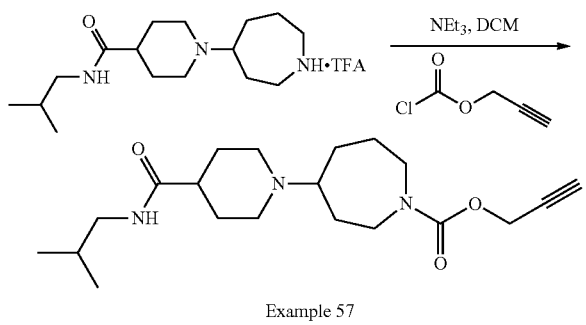

Example 57

1-(azepan-4-yl)-N-(2-methylpropyl)piperidine-4-carboxamide TFA salt (0.15 g, 0.38 mmol) was dissolved in DCM (8 mL) at rt. NEt$_3$ (0.16 mL, 1.14 mmol) and propargyl chloroformate (0.06 mL, 0.57 mmol) were added and the reaction mixture was stirred at rt for 2 h under nitrogen. The solvents were removed in vacuo, and the residue was partitioned between DCM and sat. NaHCO$_3$ sol.), organic layer washed with sat. NaCl sol. and dried over MgSO$_4$. The residue was purified by column chromatography (normal phase, [Biotage SNAP cartridge KP-sil 10 g, 40-63 μm, 60 Å, 12 mL per min, gradient 0% to 10% MeOH in DCM]) to give prop-2-yn-1-yl-4-(4-((2-methylpropyl)carbamoyl)piperidin-1-yl)azepane-1-carboxylate (0.04 g, 31%) as a yellow gum.

Data in Table 2

Route f

Typical Procedure for the Preparation of Chiral Derivatives, as Exemplified by the Preparation of Example 63, ethyl (4S)-4-[4-((2-methylpropyl)methylcarbamoyl)-piperidin-1-yl]azepane-1-carboxylate

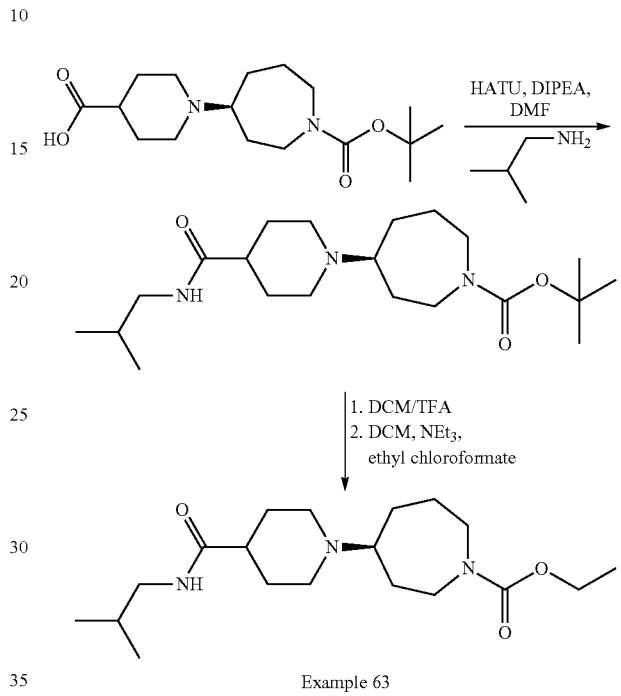

Example 63 tert-butyl (4S)-4-[4-(methoxycarbonyl)piperidin-1-yl]azepane-1-carboxylate (0.3 g, 0.92 mmol) was dissolved in DMF (4 mL) and isobutylamine (0.14 g, 0.18 mL, 1.84 mmol), HATU (0.53 g, 1.38 mmol) and DI PEA (0.36 g, 0.48 mL, 2.76 mmol) were added. The reaction mixture was stirred at rt for 48 h and the solvents were removed in vacuo. The residue was partitioned between DCM and sat. NaHCO$_3$ sol., the organic layer was washed with sat. NaCl sol. and dried (MgSO$_4$). The solvents were removed in vacuo, and the residue was purified by column chromatography (normal phase, [Biotage SNAP cartridge KP-sil 10 g, 40-63 μm, 60 Å, 12 mL per min, gradient 0% to 10% MeOH in DCM]) to give tert-butyl (4S)-4-[4-((2-methylpropyl)methylcarbamoyl)piperidin-1-yl]azepane-1-carboxylate (0.12 g, 35%) as a pale yellow gum.

LCMS (Method A): m/z 382 (M+H)$^+$ (ES$^+$), at 1.72 min, UV inactive

1-[(4S)-azepan-4-yl]-N-(2-methylpropyl)piperidine-4-carboxamide

Residue was dissolved in DCM (4 mL) and TFA (1 mL) was added. The reaction mixture was stirred at rt for 2 h under nitrogen, then the solvents were removed in vacuo. The residue was dissolved in DCM (8 mL) at rt. NEt$_3$ (0.13 mL, 0.96 mmol) and ethyl chloroformate (0.05 mL, 0.48 mmol) were added and the reaction mixture was stirred at rt overnight under nitrogen. The solvents were removed in vacuo, and the residue was partitioned between DCM and sat. NaHCO$_3$ sol.), organic layer washed with sat. NaCl sol.

and dried over MgSO$_4$. The residue was purified by column chromatography (normal phase, [Biotage SNAP cartridge KP-sil 10 g, 40-63 μm, 60 Å, 12 mL per min, gradient 0% to 10% MeOH in DCM]) to give ethyl (4S)-4-[4-((2-methylpropyl)methylcarbamoyl)piperidin-1-yl]azepane-1-carboxylate (0.24 g, 21%) as a yellow gum.

Data in Table 2

TABLE 2

| Ex. No. | Name | Intermediate | Synthetic method | ¹H NMR | LCMS Method | LCMS data |
|---|---|---|---|---|---|---|
| 1 | ethyl 4-(2-methylpropyl)carbamoyl)-1,4'-bipiperidine-1'-carboxylate | 1 | a | (400 MHz, DMSO-d₆) δ: 0.80 (d, J = 6.5, 6H), 1.16 (t, J = 7.0, 3H), 1.25-1.29 (m, 2H), 1.50-1.76 (m, 7H), 1.94-2.20 (m 3H), 2.64-2.67 (m, 1H), 2.83 (t, J = 6.3, 3H), 3.14-3.18 (m, 1H), 3.28-3.30 (m, 2H), 3.93-3.99 (m, 2H), 4.00 (q, J = 7.0, 2H), 7.68 (br. s, 1H) | B | m/z 340 (M + H)⁺ (ES⁺), at 1.21 min, UV inactive |
| 2 | ethyl 4-((3,3-difluoropyrrolidin-1-yl)carbamoyl)-1,4'-bipiperidine-1'-carboxylate | 1 | a | (400 MHz, CDCl₃) δ: 1.26 (t, J = 7.1, 3H), 1.38-1.50 (m, 1H), 1.63-1.89 (m, 5H), 2.15-2.51 (m, 9H), 2.65-2.78 (m, 2H), 2.91-3.05 (m, 2H), 3.68-3.83 (m, 5H), 4.12 (q, J = 7.2, 2H) | B | m/z 374 (M + H)⁺ (ES⁺), at 3.91 min, UV inactive |
| 3 | ethyl 4-(2,3-dimethylbutan-2-yl)carbamoyl)-1,4'-bipiperidine-1'-carboxylate | 1 | a | (400 MHz, DMSO-d₆) δ: 0.75 (d, J = 6.8, 6H), 1.09 (s, 6H), 1.13 (d, J = 7.2, 3H), 1.21-2.32 (m, 12H), 2.69-3.10 (m, 5H), 3.94-4.01 (m, 4H), 7.09 (br. s, 1H) | B | m/z 368 (M + H)⁺ (ES⁺), at 3.78 min, UV inactive |
| 4 | ethyl 4-(1,1-dimethylpropyl)carbamoyl)-1,4'-bipiperidine-1'-carboxylate | 1 | a | (400 MHz, DMSO-d₆) δ: 0.69 (t, J = 7.1, 3H), 1.12-1.15 (m, 9H), 1.26-2.36 (m, 13H), 2.60-2.93 (m, 5H), 3.94-4.01 (m 4H), 7.07 (br. s, 1H) | B | m/z 354 (M + H)⁺ (ES⁺), at 3.46 min, UV inactive |
| 5 | ethyl 4-(1-methylcyclobutyl)carbamoyl)-1,4'-bipiperidine-1'-carboxylate | 1 | a | (400 MHz, DMSO-d₆) δ: 1.13 (t, J = 7.1, 3H), 1.28 (s, 3H), 1.20-2.30 (m, 17H), 2.69-2.85 (m, 5H), 3.94-4.01 (m 4H), 7.66 (br. s, 1H) | B | m/z 352 (M + H)⁺ (ES⁺), at 3.14 min, UV inactive |
| 6 | ethyl 4-(4-((2-methylpropyl)carbamoyl)piperidin-1-yl)azepane-1-carboxylate | 2 | b | (400 MHz, DMSO-d₆) δ: 0.92 (d, J = 6.5, 6H), 1.20 (m, 3H), 1.25-2.05 (m, 14H), 2.55-2.88 (m, 3H), 2.80-2.90 (m, 2H), 3.20-3.29 (m, 2H), 3.40-3.48 (m, 2H), 4.02-4.07 (m, 2H), 7.96 (m, 1H) | C | m/z 354 (M + H)⁺ (ES⁺), at 2.90 min, UV inactive |
| 7 | ethyl 4-(4-((1,1-dimethylethyl)carbamoyl)piperidin-1-yl)azepane-1-carboxylate | 2 | b | (400 MHz, DMSO-d₆) δ: 1.17 (td, J = 7.1, 2.1, 3H), 1.22 (s, 9H), 1.30-1.56 (m, 7H), 1.68-1.83 (m, 3H), 1.93-2.16 (m, 3H), 2.34-2.40 (m, 1H), 2.68-2.75 (m, 2H), 3.12-3.27 (m, 2H), 3.38-3.47 (m, 2H), 4.02 (qd, J = 7.0, 3.2, 2H), 7.26 (br. s, 1H) | C | m/z 354 (M + H)⁺ (ES⁺), at 2.88 min, UV inactive |
| 8 | ethyl 4-(4-((2-methylpropyl)carbamoyl)piperidin-1-yl)azepane-1-carboxylate | 2 | b | (400 MHz, DMSO-d₆) δ: 0.79 (d, J = 6.6, 3H), 0.83 (t, J = 7.4, 3H), 0.95-1.08 (m, 1H), 1.17 (td, J = 7.0, 2.0, 3H), 1.27-1.62 (m, 8H), 1.68-1.85 (m, 3H), 2.07-2.17 (m, 3H), 2.32-2.42 (m, 1H), 2.68-2.76 (m, 2H), 2.77-2.87 (m, 1H), 2.88-2.99 (m, 2H), 3.15-3.28 (m, 2H), 3.44-3.51 (m, 2H), 4.02 (qd, J = 7.1, 3.0, 2H), 7.67 (t, J = 6.1, 1H) | C | m/z 368 (M + H)⁺ (ES⁺), at 3.07 min, UV inactive |
| 9 | ethyl 4-(4-((2,2-dimethylpropyl)carbamoyl)piperidin-1-yl)azepane-1-carboxylate | 2 | b | (400 MHz, DMSO-d₆) δ: 0.81 (s, 9H), 1.17 (td, J = 7.0, 2.3, 3H), 1.30-1.65 (m, 6H), 1.70-1.85 (m, 3H), 2.05-2.21 (m, 3H), 2.32-2.46 (m, 1H), 2.65-2.79 (m, 2H), 2.82-3.03 (m, 3H), 3.12-3.27 (m, 2H), 3.44-3.49 (m, 2H), 4.07 (qd, J = 7.0, 3.0, 2H), 7.63 (t, J = 6.2, 1H) | C | m/z 368 (M + H)⁺ (ES⁺), at 1.82 min, UV inactive |
| 10 | ethyl 4-(4-((1,1-dimethylpropyl)carbamoyl)piperidin-1-yl)azepane-1-carboxylate | 2 | b | (400 MHz, DMSO-d₆) δ: 0.72 (t, J = 7.4, 3H), 1.10-1.22 (m, 9H), 1.30-1.65 (m, 9H), 1.70-1.85 (m, 3H), 2.00-2.19 (m, 3H), 2.32-2.46 (m, 1H), 2.65-2.76 (m, 2H), 3.12-3.27 (m, 2H), 3.39-3.48 (m, 2H), 4.02 (qd, J = 6.9, 3.1, 2H), 7.11 (br. s, 1H) | C | m/z 368 (M + H)⁺ (ES⁺), at 1.87 min, UV inactive |
| 11 | ethyl 4-(4-((cyclobutylmethyl)carbamoyl)piperidin-1-yl)azepane-1-carboxylate | 2 | b | (400 MHz, DMSO-d₆) δ: 1.18 (t, J = 6.8, 3H), 1.30-1.68 (m, 8H), 1.70-1.86 (m, 5H), 1.89-2.18 (m, 5H), 2.32-2.46 (m, 3H), 2.67-2.76 (m, 2H), 3.02-3.09 (m, 2H), | C | m/z 366 (M + H)⁺ (ES⁺), at 1.77 min, UV inactive |

TABLE 2-continued

| Ex. No. | Name | Intermediate | Synthetic method | ¹H NMR | LCMS Method | LCMS data |
|---|---|---|---|---|---|---|
| 12 | ethyl 4-(4-((diethyl)carbamoyl)piperidin-1-yl)azepane-1-carboxylate | 2 | b | (400 MHz, DMSO-d₆) δ: 0.98 (t, J = 7.0, 3H), 1.10 (t, J = 7.0, 3H), 1.17 (td, J = 7.0, 2.0, 3H), 1.30-1.65 (m, 7H), 1.70-1.85 (m, 3H), 2.17-2.22 (m, 2H), 2.37-2.45 (m, 2H), 2.67-2.78 (m, 2H), 3.16-3.29 (m, 6H), 3.41-3.45 (m, 2H), 4.02 (dq, J = 7.0, 2.2, 2H) 3.16-3.23 (m, 2H), 3.40-3.50 (m, 2H), 4.03 (q, J = 6.9, 2H), 7.62 (br. s, 1H) | C | m/z 354 (M + H)⁺ (ES⁺), at 1.888 min, UV inactive |
| 13 | ethyl 4-(4-((ethyl(propan-2-yl)carbamoyl)piperidin-1-yl)azepane-1-carboxylate | 2 | b | (400 MHz, DMSO-d₆) δ: 1.00 (t, J = 6.9, 3H), 1.05 (d, J = 6.8, 3H), 1.10-1.20 (m, 6H), 1.27-1.48 (m, 2H), 1.48-1.65 (m, 5H), 1.70-1.86 (m, 3H), 2.14-2.28 (m, 2H), 2.30-2.42 (m, 2H), 2.65-2.77 (m, 2H), 3.09-3.28 (m, 4H), 3.40-3.49 (m, 2H), 4.03 (qd, J = 7.0, 2.0, 2H), 4.10 (quint, J = 6.8, 0.5H), 4.50 (quint, J = 6.8, 0.5H) | C | m/z 368 (M + H)⁺ (ES⁺), at 3.56 min, UV inactive |
| 14 | ethyl 4-(4-((3-methoxy-2-methylpropyl)carbamoyl)piperidin-1-yl)azepane-1-carboxylate | 2 | b | (400 MHz, CDCl₃) δ: 0.90 (d, J = 7.0, 3H), 1.26 (td, J = 7.1, 2.3, 3H), 1.39-1.72 (m, 5H), 1.75-2.00 (m, 6H), 2.01-2.09 (m, 1H), 2.15-2.34 (m, 2H), 2.44-2.52 (m, 1H), 2.74-2.89 (m, 2H), 3.06 (ddd, J = 13.2, 8.4, 4.3, 1H), 3.19-3.32 (m, 3H), 3.35 (s, 3H), 3.38-3.55 (m, 3H), 3.56-3.66 (m, 1H), 4.13 (qd, J = 7.0, 1.6, 2H), 6.32 (br. s, 1H) | C | m/z 384 (M + H)⁺ (ES⁺), at 1.73 min, UV inactive |
| 15 | ethyl 4-(4-((cyclopropylmethyl)carbamoyl)piperidin-1-yl)azepane-1-carboxylate | 2 | b | (400 MHz, CDCl₃) δ: 0.17-0.23 (m, 2H), 0.47-0.52 (m, 2H), 0.88-0.97 (m, 1H), 1.26 (t, J = 7.1, 2.1, 3H), 1.35-1.78 (m, 5H), 1.80-2.15 (m, 6H), 2.18-2.35 (m, 2H), 2.44-2.53 (m, 1H), 2.75-2.90 (m, 2H), 3.08-3.13 (m, 2H), 3.22-3.32 (m, 2H), 3.48-3.63 (m, 4H), 4.10-4.16 (m, 2H), 5.64 (br. s, 1H) | C | m/z 352 (M + H)⁺ (ES⁺), at 1.71 min, UV inactive |
| 16 | ethyl 4-(4-((cyclopentylmethyl)carbamoyl)piperidin-1-yl)azepane-1-carboxylate | 2 | b | (400 MHz, DMSO-d₆) δ: 1.13-1.21 (m, 3H), 1.26 (td, J = 7.1, 2.0, 3H), 1.36-2.50 (m, 21H), 2.75-2.92 (m, 2H), 3.15-3.35 (m, 4H), 3.45-3.65 (m, 2H), 4.10-4.18 (m, 2H), 5.55 (br. s, 1H) | B | m/z 380 (M + H)⁺ (ES⁺), at 2.03 min, UV inactive |
| 17 | ethyl 4-(4-((1-methylcyclohexyl)carbamoyl)piperidin-1-yl)azepane-1-carboxylate | 2 | b | (400 MHz, DMSO-d₆) δ: 1.11-1.20 (m, 3H), 1.20 (s, 3H), 1.21-1.24 (m, 9H), 1.33-1.84 (m, 14H), 1.97-2.06 (m, 2H), 3.05-3.28 (m, 3H), 3.40-3.67 (m, 2H), 4.00-4.08 (m, 2H), 7.10 (br. s, 1H) | B | m/z 394 (M + H)⁺ (ES⁺), at 3.94 min, UV inactive |
| 18 | ethyl 4-(4-(([1-methylcyclopentyl]methyl)carbamoyl)piperidin-1-yl)azepane-1-carboxylate | 2 | b | (400 MHz, DMSO-d₆) δ: 0.89 (s, 3H), 1.14-1.30 (m, 6H), 1.38-1.87 (m, 21H), 2.96 (d, J = 6.3, 2H), 3.17-3.28 (m, 2H), 3.40-3.52 (m, 2H), 4.04 (q, J = 6.8, 2H), 7.70 (br. s, 1H) | B | m/z 394 (M + H)⁺ (ES⁺), at 3.87 min, UV inactive |
| 19 | ethyl 4-(4-((2,2,2-trifluoroethyl)carbamoyl)piperidin-1-yl)azepane-1-carboxylate | 2 | b | (400 MHz, DMSO-d₆) δ: 1.17 (td, J = 7.1, 2.3, 3H), 1.30-1.82 (m, 10H), 2.07-2.19 (m, 2H), 2.32-2.43 (m, 2H), 2.66-2.77 (m, 2H), 3.19-3.27 (m, 2H), 3.43-3.46 (m, 2H), 3.82-3.91 (m, 2H), 4.03 (qd, J = 6.9, 2.6, 2H), 8.42 (t, J = 6.2, 1H) | C | m/z 380 (M + H)⁺ (ES⁺), at 2.72 min, UV inactive |
| 20 | ethyl 4-(4-(3,3,3-trifluoro-2-methoxypropyl)carbamoyl)piperidin-1-yl)azepane-1-carboxylate | 2 | b | (400 MHz, DMSO-d₆) δ: 1.17 (td, J = 7.0, 2.0, 3H), 1.30-1.85 (m, 10H), 2.03-2.19 (m, 2H), 2.35-2.45 (m, 2H), 2.66-2.77 (m, 2H), 3.10-3.27 (m, 2H), 3.37-3.45 (m, 2H), 3.47 (s, 3H), 3.84-3.92 (m, 2H), 4.03 (qd, J = 7.0, 2.5, 2H), 8.05 (t, J = 5.7, 1H) | C | m/z 424 (M + H)⁺ (ES⁺), at 1.89 min, UV inactive |
| 21 | ethyl 4-(4-((tetrahydrofuran-3-yl)methyl)carbamoyl)piperidin-1-yl)azepane-1-carboxylate | 2 | b | (400 MHz, CDCl₃) δ: 1.26 (t, J = 7.0, 3H), 1.41-2.09 (m, 15H), 2.16-2.32 (m, 2H), 2.42-2.55 (m, 2H), 2.76-2.95 (m, 2H), 3.20-3.62 (m, 6H), 3.67-3.96 (m, 2H) | B | m/z 382 (M + H)⁺ (ES⁺), at 2.49 min, UV inactive |

TABLE 2-continued

| Ex. No. | Name | Intermediate | Synthetic method | ¹H NMR | LCMS Method | LCMS data |
|---|---|---|---|---|---|---|
| | 1-yl)azepane-1-carboxylate | | | 4.09-4.18 (m, 2H), 5.73 (br. s, 1H) | | |
| 22 | ethyl 4-(4-(((methoxy(methyl))carbamoyl)piperidin-1-yl)azepane-1-carboxylate | 2 | b | (400 MHz, DMSO-d$_6$) δ: 1.13-1.23 (m, 3H), 1.40-2.30 (m, 13H), 2.38-2.45 (m, 1H), 2.65-2.82 (m, 2H), 3.10 (s, 3H), 3.20-3.29 (m, 2H), 3.40-3.52 (m, 2H), 3.69 (s, 3H), 4.04 (q, J = 6.7, 2H) | B | m/z 342 (M + H)$^+$ (ES$^+$), at 2.84 min, UV inactive |
| 23 | ethyl 4-(4-((propan-2-yloxy)carbamoyl)piperidin-1-yl)azepane-1-carboxylate | 2 | b | (400 MHz, DMSO-d$_6$) δ: 1.11 (d, J = 6.3, 6H), 1.18 (td, J = 7.0, 3.1, 3H), 1.22-2.30 (m, 13H), 2.55-3.00 (m, 3H), 3.15-3.29 (m, 2H), 3.40-3.55 (m, 2H), 3.89-3.98 (m, 1H), 4.04 (m, 2H), 10.80 (br. s, 1H) | B | m/z 356 (M + H)$^+$ (ES$^+$), at 2.58 min, UV inactive |
| 24 | ethyl 4-(4-((2-methylallyl)carbamoyl)piperidin-1-yl)azepane-1-carboxylate | 2 | c | (400 MHz, CD$_3$OD) δ: 1.28 (td, J = 7.1, 3.2, 3H), 1.42-1.88 (m, 11H), 1.88-2.09 (m, 3H), 2.20-2.31 (m, 1H), 2.32-2.48 (m, 2H), 2.57 (t, J = 9.8, 1H), 2.85-2.98 (m, 2H), 3.27-3.41 (m, 2H), 3.51-3.64 (m, 2H), 3.74 (s, 2H), 4.14 (qd, J = 7.1, 3.2, 2H), 4.83 (d, J = 1.3, 2H) | C | m/z 352 (M + H)$^+$ (ES$^+$), at 0.81 min, UV inactive |
| 25 | ethyl 4-(4-(butylcarbamoyl)piperidin-1-yl)azepane-1-carboxylate | 2 | c | (400 MHz, CD$_3$OD) δ: 0.95 (t, J = 7.3, 3H), 1.28 (td, J = 7.1, 3.2, 3H), 1.32-1.42 (m, 2H), 1.42-1.84 (m, 8H), 1.86-2.07 (m, 3H), 2.18 (tt, J = 10.2, 4.9, 1H), 2.30-2.44 (m, 2H), 2.55 (t, J = 9.2, 1H), 2.84-2.94 (m, 2H), 3.18 (t, J = 7.1, 2H), 3.25-3.42 (m, 4H), 3.52-3.65 (m, 2H), 4.14 (qd, J = 7.1, 3.3, 2H) | C | m/z 354 (M + H)$^+$ (ES$^+$), at 0.86 min, UV inactive |
| 26 | ethyl 4-(((cyclopropylmethyl)(ethyl)carbamoyl)piperidin-1-yl)azepane-1-carboxylate | 2 | c | (400 MHz, CD$_3$OD) δ: 0.21-0.26 (m, 1H), 0.26-0.32 (m, 1H), 0.47 (ddd, J = 8.0, 5.9, 4.3, 1H), 0.59 (ddd, J = 8.0, 5.9, 4.6, 1H), 0.87-1.04 (m, 1H), 1.10 (t, J = 7.1, 2H), 1.17-1.32 (m, 5H), 1.35-2.08 (m, 10H), 2.30-2.66 (m, 4H), 2.78-2.93 (m, 2H), 3.20-3.38 (m, 3H), 3.41-3.62 (m, 4H), 4.11 (qd, J = 7.1, 3.5, 2H) | C | m/z 380 (M + H)$^+$ (ES$^+$), at 1.00 min, UV inactive |
| 27 | ethyl 4-(4-((1-methylcyclobutyl)carbamoyl)piperidin-1-yl)azepane-1-carboxylate | 2 | c | (400 MHz, CD$_3$OD) δ: 1.24 (m, J = 7.1, 3.4, 3H), 1.39 (s, 3H), 1.41-2.03 (m, 12H), 2.03-2.15 (m, 1H), 2.17-2.28 (m, 2H), 2.28-2.42 (m, 1H), 2.44-2.60 (m, 1H), 2.77-2.94 (m, 2H), 3.20-3.36 (m, 5H), 3.48-3.58 (m, 3H), 4.10 (qd, J = 7.1, 3.4, 2H) | C | m/z 366 (M + H)$^+$ (ES$^+$), at 0.96 min, UV inactive |
| 28 | ethyl 4-(4-((1-cyclopropylpropan-2-yl)carbamoyl)piperidin-1-yl)azepane-1-carboxylate | 2 | c | (400 MHz, CD$_3$OD) δ: -0.05-0.13 (m, 2H), 0.33-0.47 (m, 2H), 1.12 (d, J = 6.7, 3H), 1.24 (td, J = 7.1, 3.4, 3H), 1.27-1.37 (m, 2H), 1.37-1.79 (m, 8H), 1.81-2.05 (m, 3H), 2.06-2.20 (m, 1H), 2.25-2.42 (m, 2H), 2.45-2.57 (m, 1H), 2.78-2.92 (m, 2H), 3.22-3.37 (m, 3H), 3.47-3.59 (m, 2H), 3.85-4.00 (m, 1H), 4.10 (qd, J = 7.1, 3.4, 2H) | C | m/z 380 (M + H)$^+$ (ES$^+$), at 0.98 min, UV inactive |
| 29 | ethyl 4-(4-(cyclopent-3-en-1-ylcarbamoyl)piperidin-1-yl)azepane-1-carboxylate | 2 | c | (400 MHz, CD$_3$OD) δ: 1.24 (td, J = 7.1, 3.3, 3H), 1.34-1.79 (m, 7H), 1.80-2.05 (m, 3H), 2.06-2.23 (m, 3H), 2.24-2.41 (m, 2H), 2.45-2.56 (m, 1H), 2.67 (ddd, J = 16.7, 8.0, 2.1, 2H), 2.77-2.91 (m, 2H), 3.22-3.36 (m, 3H), 3.48-3.60 (m, 3H), 4.10 (qd, J = 7.1, 3.4, 2H), 4.31-4.43 (m, 1H), 5.62-5.74 (m, 2H) | C | m/z 364 (M + H)$^+$ (ES$^+$), at 0.84 min, UV inactive |
| 30 | ethyl 4-(4-(cyclopentylcarbamoyl)piperidin-1-yl)azepane-1-carboxylate | 2 | c | (400 MHz, CD$_3$OD) δ: 1.24 (td, J = 7.1, 3.4, 3H), 1.32-1.80 (m, 13H), 1.82-2.05 (m, 5H), 2.06-2.21 (m, 1H), 2.26-2.44 (m, 2H), 2.48-2.62 (m, 1H), 2.79-2.98 (m, 2H), 3.20-3.41 (m, 3H), 3.48-3.60 (m, 2H), 3.96-4.18 (m, 3H) | C | m/z 366 (M + H)$^+$ (ES$^+$), at 0.96 min, UV inactive |
| 31 | ethyl 4-(4-((2,3-dimethylbutan-2- | 2 | c | (400 MHz, CD$_3$OD) δ: 0.85 (d, J = 6.9, 6H), 1.21 (s, 6H), 1.24 (td, J = 7.1, 3.5, 3H), 1.32-1.78 (m, 7H), | C | m/z 382 (M + H)$^+$ (ES$^+$), at 1.18 min, |

TABLE 2-continued

| Ex. No. | Name | Intermediate | Synthetic method | 1H NMR | LCMS Method | LCMS data |
|---|---|---|---|---|---|---|
| | yl)carbamoyl)piperidin-1-yl)azepane-1-carboxylate | | | 1.83-2.05 (m, 3H), 2.09-2.22 (m, 1H), 2.30-2.42 (m, 2H), 2.46-2.60 (m, 1H), 2.80-2.95 (m, 2H), 3.22-3.40 (m, 4H), 3.48-3.59 (m, 2H), 4.10 (qd, J = 7.1, 3.3, 2H) | | UV inactive |
| 32 | 4-(4-(allylcarbamoyl)piperidin-1-yl)azepane-1-carboxylate | 2 | c | (400 MHz, CD3OD) δ: 1.24 (td, J = 7.1, 3.4, 3H), 1.36-2.07 (m, 10H), 2.16-2.29 (m, 1H), 2.33-2.52 (m, 2H), 2.53-2.66 (m, 1H), 2.84-3.03 (m, 2H), 3.20-3.37 (m, 3H), 3.48-3.61 (m, 2H), 3.76 (dt, J = 5.4, 1.6, 2H), 4.10 (qd, J = 7.1, 3.3, 2H), 5.08 (ddt, J = 23.4, 1.6, 1.6, 1H), 5.12 (ddt, J = 17.2, 1.6, 1.6, 1H), 5.88-5.73 (m, 1H) | C | m/z 338 (M + H)+ (ES+), at 0.74 min, UV inactive |
| 33 | ethyl 4-(4-(2-methylpiperidine-1-carbonyl)piperidin-1-yl)azepane-1-carboxylate | 2 | c | (400 MHz, CD3OD) δ: 1.13 (d, J = 7.0, 1.5H), 1.19-1.32 (m, 4.5H), 1.33-2.05 (m, 14H), 2.29-2.92 (m, 7H), 3.14-3.37 (m, 3H), 3.48-3.60 (m, 2H), 3.72-3.85 (m, 1H), 4.10 (qd, J = 7.1, 3.4, 2H), 4.23-4.42 (m, 1H), 4.73-4.81 (m, 1H) | C | m/z 380 (M + H)+ (ES+), at 1.10 min, UV inactive |
| 34 | ethyl 4-(4-(diisopropylcarbamoyl)piperidin-1-yl)azepane-1-carboxylate | 2 | c | (400 MHz, DMSO-d6 at 100° C.) δ: 1.13-1.31 (m, 17H), 1.39-1.71 (m, 5H), 1.74-1.89 (m, 4H), 2.18-2.30 (m, 2H), 2.35-2.62 (m, 2H), 2.73-2.84 (m, 2H), 3.182-3.32 (m, 2H), 3.41-3.54 (m, 2H), 3.729-3.89 (m, 2H), 4.06 (q, J = 7.0, 2H) | C | m/z 382 (M + H)+ (ES+), at 1.28 min, UV inactive |
| 35 | ethyl 4-(4-((2-methylbut-3-yn-2-yl)carbamoyl)piperidin-1-yl)azepane-1-carboxylate | 2 | c | (400 MHz, CD3OD) δ: 1.28 (td, J = 7.1, 3.3, 3H), 1.32-1.55 (m, 2H), 1.57 (s, 6H), 1.60-1.83 (m, 5H), 1.87-2.09 (m, 3H), 2.13-2.25 (m, 1H), 2.33-2.50 (m, 2H), 2.52-2.65 (s, 2H), 2.87-2.99 (m, 2H), 3.26-3.44 (m, 3H), 3.52-3.62 (m, 2H), 4.14 (qd, J = 7.1, 3.1, 2H) | C | m/z 364 (M + H)+ (ES+), at 1.19 min, UV inactive |
| 36 | ethyl 4-(4-(methyl(prop-2-yn-1-yl)carbamoyl)piperidin-1-yl)azepane-1-carboxylate | 2 | c | (400 MHz, CD3OD) δ: 1.26 (td, J = 7.1, 3.3, 3H), 1.41-1.83 (m, 6H), 1.86-2.07 (m, 3H), 2.36-2.82 (m, 5H), 2.83-2.94 (m, 2H), 2.96 (s, 1H), 3.15-3.18 (m, 2H), 3.24-3.28 (m, 1H), 3.33-3.42 (m, 2H), 3.50-3.62 (m, 2H), 4.12 (qd, J = 7.1, 3.1, 2H), 4.18 (d, J = 2.4, 1H), 4.24 (d, J = 2.4, 1H) | C | m/z 350 (M + H)+ (ES+), at 1.05 min, UV inactive |
| 37 | ethyl 4-(4-(((1-ethylcyclobutyl)methyl)carbamoyl)piperidin-1-yl)azepane-1-carboxylate | 2 | c | (400 MHz, CD3OD) δ: 0.86 (t, J = 7.4, 3H), 1.28 (td, J = 7.1, 3.3, 3H), 1.42-1.53 (m, 2H), 1.53-2.08 (m, 16H), 2.20-2.31 (m, 1H), 2.32-2.47 (m, 2H), 2.49-2.62 (m, 1H), 2.84-2.96 (m, 2H), 3.24 (s, 2H), 3.26-3.44 (m, 3H), 3.52-3.63 (m, 2H), 4.14 (qd, J = 7.1, 3.3, 2H) | C | m/z 394 (M + H)+ (ES+), at 1.25 min, UV inactive |
| 38 | ethyl 4-(4-((1,1,1-trifluoro-2-methylpropan-2-yl)carbamoyl)piperidin-1-yl)azepane-1-carboxylate | 2 | c | (400 MHz, DMSO-d6) δ: 1.09-1.18 (m, 3H), 1.19-1.24 (m, 2H), 1.43 (s, 6H), 1.60-2.30 (m, 10H), 2.39-2.46 (m, 2H), 2.75-3.00 (m, 2H), 3.13-3.29 (m, 4H), 3.34-3.61 (m, 2H), 3.97-4.02 (m, 2H), 7.90 (br. s, 1H) | B | m/z 408 (M + H)+ (ES+), at 3.52 min, UV inactive |
| 39 | ethyl 4-(4-((2-cyclopropylpropyl)carbamoyl)piperidin-1-yl)azepane-1-carboxylate | 2 | b | (400 MHz, CD3OD) δ: 0.09-0.02 (m, 1H), 0.26-0.11 (m, 2H), 0.61-0.33 (m, 3H), 0.99-0.80 (m, 3H), 1.16-0.99 (m, 3H), 1.34-1.20 (m, 3H), 1.79-1.55 (m, 2H), 2.16-1.81 (m, 6H), 2.28-2.18 (m, 1H), 2.55-2.42 (m, 1H), 3.00 (s, 2H), 3.21-3.04 (m, 3H), 3.50-3.24 (m, 4H), 3.64-3.54 (m, 2H), 3.70 (dt, J = 14.5, 4.9 Hz, 1H), 4.22-4.04 (m, 2H) | C | m/z 380 (M + H)+ (ES+), at 1.06 min, UV inactive |
| 40 | ethyl 4-(4-fluoro-4-((2-methylpropyl)carbamoyl)piperidin-1-yl)azepane-1-carboxylate | 3 | b | (400 MHz, DMSO-d6) δ: 0.81 (d, J = 6.8, 6H), 1.14-1.20 (m, 3H), 1.32-2.10 (m, 10H), 2.30-2.45 (m, 2H), 2.55-2.67 (m, 2H), 2.87-2.99 (m, 4H), 3.15-3.29 (m, 2H), 3.40-3.55 (m, 2H), 4.01-4.05 (m, 2H), 8.08 (br. s, 1H) | B | m/z 372 (M + H)+ (ES+), at 3.62 min, UV inactive |

| Ex. No. | Name | Intermediate | Synthetic method | $^1$H NMR | LCMS Method | LCMS data |
|---|---|---|---|---|---|---|
| 41 | ethyl 4-(4-fluoro-4-((1,1-dimethylpropyl)carbamoyl)piperidin-1-yl)azepane-1-carboxylate | 3 | b | (400 MHz, DMSO-d$_6$) δ: 0.71 (t, J = 7.4, 3H), 1.19 (s, 6H), 1.35-2.49 (m, 15H), 3.07-3.25 (m, 4H), 3.35-3.60 (m, 2H), 4.00 (q, J = 6.8, 2H), 7.17 (br. s, 1H) | B | m/z 386 (M + H)$^+$ (ES$^+$), at 4.31 min, UV inactive |
| 42 | ethyl 4-(4-fluoro-4-((cyclobutylmethyl)carbamoyl)piperidin-1-yl)azepane-1-carboxylate | 3 | b | (400 MHz, DMSO-d$_6$) δ: 1.12-1.30 (m, 18H), 3.06-3.14 (m, 2H), 3.20-3.29 (m, 2H), 3.35-3.50 (m, 2H), 3.53-3.62 (m, 2H), 4.00 (q, J = 6.7, 2H), 8.16 (br. s, 1H) | B | m/z 384 (M + H)$^+$ (ES$^+$), at 3.96 min, UV inactive |
| 43 | ethyl 4-(4-fluoro-4-((tert-butyl)carbamoyl)piperidin-1-yl)azepane-1-carboxylate | 3 | d | (400 MHz, DMSO-d$_6$) δ: 1.10-1.17 (m, 3H), 1.24 (s, 9H), 1.30-2.05 (m, 11H), 2.24-2.43 (m, 2H), 2.53-2.69 (m, 2H), 3.10-3.29 (m, 2H), 3.32-3.45 (m, 2H), 3.96-4.02 (m, 2H), 7.06 (br. s, 1H) | B | m/z 372 (M + H)$^+$ (ES$^+$), at 3.90 min, UV inactive |
| 44 | ethyl 4-(4-fluoro-4-((2,3-dimethylbutan-2-yl)carbamoyl)piperidin-1-yl)azepane-1-carboxylate | 3 | d | (400 MHz, DMSO-d$_6$) δ: 0.76 (d, J = 6.9, 6H), 1.11-1.19 (m, 9H), 1.26-2.01 (m, 11H), 2.25-2.43 (m, 3H), 2.52-2.64 (m, 2H), 3.10-3.24 (m, 2H), 3.34-3.45 (m, 2H), 3.95-4.02 (m, 2H), 6.82 (br. s, 1H) | B | m/z 400 (M + H)$^+$ (ES$^+$), at 4.47 min, UV inactive |
| 45 | ethyl 4-(4-fluoro-4-((1-cyclopropylpropan-2-yl)carbamoyl)piperidin-1-yl)azepane-1-carboxylate | 3 | d | (400 MHz, DMSO-d$_6$) δ: −0.09–−0.03 (m, 1H), 0.03–0.08 (m, 1H), 0.26-0.32 (m, 1H), 0.33-0.48 (m, 1H), 0.79-0.94 (m, 4H), 1.13 (t, J = 6.9, 3H), 1.26-2.05 (m, 11H), 2.25-2.43 (m, 3H), 2.52-2.65 (m, 2H), 2.90-3.00 (m, 1H), 3.05-3.21 (m, 3H), 3.34-3.45 (m, 2H), 3.99 (qd, J = 6.9, 2.0, 2H), 7.95 (br. s, 1H) | B | m/z 398 (M + H)$^+$ (ES$^+$), at 4.04 min, UV inactive |
| 46 | ethyl 4-(4-fluoro-4-((2,2-dimethylpropyl)carbamoyl)piperidin-1-yl)azepane-1-carboxylate | 3 | d | (400 MHz, DMSO-d$_6$) δ: 0.78 (s, 9H), 1.13 (t, J = 6.9, 3H), 1.30-2.05 (m, 10H), 2.25-2.44 (m, 3H), 2.53-2.69 (m, 2H), 2.88 (d, J = 6.5, 2H), 3.11-3.24 (m, 2H), 3.33-3.46 (m, 2H), 3.99 (q, J = 6.9, 2H), 7.83 (br. s, 1H) | B | m/z 386 (M + H)$^+$ (ES$^+$), at 4.01 min, UV inactive |
| 47 | ethyl 4-(4-fluoro-4-((1-methylcyclopropyl)carbamoyl)piperidin-1-yl)azepane-1-carboxylate | 3 | d | (400 MHz, DMSO-d$_6$) δ: 0.45-0.49 (m, 2H), 0.56-0.61 (m, 2H), 1.13 (t, J = 6.9, 3H), 1.21 (s, 3H), 1.26-2.00 (m, 10H), 2.24-2.44 (m, 3H), 2.52-2.65 (m, 2H), 3.10-3.22 (m, 2H), 3.33-3.46 (m, 2H), 3.99 (q, J = 6.9, 2H), 8.16 (br. s, 1H) | B | m/z 370 (M + H)$^+$ (ES$^+$), at 3.25 min, UV inactive |
| 48 | ethyl 4-(4-fluoro-4-((1-methylcyclopentyl)carbamoyl)piperidin-1-yl)azepane-1-carboxylate | 3 | d | (400 MHz, DMSO-d$_6$) δ: 1.13 (t, J = 6.9, 3H), 1.26 (s, 3H), 1.30-2.05 (m, 18H), 2.25-2.44 (m, 3H), 2.53-2.65 (m, 2H), 3.10-3.23 (m, 2H), 3.33-3.45 (m, 2H), 3.95-4.02 (m, 2H), 7.23 (br. s, 1H) | B | m/z 398 (M + H)$^+$ (ES$^+$), at 4.24 min, UV inactive |
| 49 | ethyl 4-(4-fluoro-4-(((1-ethylcyclobutyl)methyl)carbamoyl)piperidin-1-yl)azepane-1-carboxylate | 3 | d | (400 MHz, DMSO-d$_6$) δ: 0.75 (t, J = 7.3, 3H), 1.13 (t, J = 6.9, 3H), 1.25-2.05 (m, 18H), 2.26-2.44 (m, 2H), 2.53-2.65 (m, 2H), 3.08 (d, J = 6.0, 2H), 3.10-3.25 (m, 2H), 3.34-3.46 (m, 2H), 3.96-4.02 (m, 2H), 7.85 (d, J = 2.7, 1H) | B | m/z 412 (M + H)$^+$ (ES$^+$), at 4.53 min, UV inactive |
| 50 | ethyl 4-(4-fluoro-4-((1-methylcyclobutyl)carbamoyl)piperidin-1-yl)azepane-1-carboxylate | 3 | d | (400 MHz, DMSO-d$_6$) δ: 1.13 (t, J = 6.9, 3H), 1.32 (s, 3H), 1.34-2.00 (m, 14H), 2.12-2.24 (m, 2H), 2.25-2.44 (m, 3H), 2.53-2.62 (m, 2H), 3.10-3.23 (m, 2H), 3.32-3.45 (m, 2H), 3.99 (q, J = 6.7, 2H), 7.84 (br. s, 1H) | B | m/z 384 (M + H)$^+$ (ES$^+$), at 3.37 min, UV inactive |
| 51 | ethyl 4-(4-fluoro-4-((cyclopentyl)carbamoyl)piperidin-1-yl)azepane-1-carboxylate | 3 | d | (400 MHz, DMSO-d$_6$) δ: 1.10-1.16 (m, 3H), 1.27-2.05 (m, 19H), 2.20-2.44 (m, 3H), 2.53-2.65 (m, 2H), 3.10-3.25 (m, 2H), 3.33-3.45 (m, 2H), 3.93-4.02 (m, 2H), 7.86 (d, J = 2.3, 1H) | B | m/z 384 (M + H)$^+$ (ES$^+$), at 3.81 min, UV inactive |
| 52 | ethyl 4-(4-fluoro-4-((cyclopropylmethyl)carbamoyl)piperidin-1-yl)azepane-1-carboxylate | 3 | d | (400 MHz, DMSO-d$_6$) δ: 0.09-0.12 (m, 2H), 0.30-0.36 (m, 2H), 0.85-0.94 (m, 1H), 1.13 (t, J = 7.1, 3H), 1.25-2.02 (m, 10H), 2.25-2.44 (m, 3H), 2.53-2.65 (m, 2H), 2.92 (t, J = 6.2, | B | m/z 370 (M + H)$^+$ (ES$^+$), at 3.48 min, UV inactive |

TABLE 2-continued

| Ex. No. | Name | Intermediate | Synthetic method | $^1$H NMR | LCMS Method | LCMS data |
|---|---|---|---|---|---|---|
|  | yl]azepane-1-carboxylate |  |  | 2H), 3.10-3.23 (m, 2H), 3.33-3.46 (m, 2H), 3.99 (q, J = 6.9, 2H), 8.10 (br. s, 1H) |  |  |
| 53 | ethyl 4-(4-fluoro-4-(((cyclopentylmethyl)carbamoyl)piperidin-1-yl)azepane-1-carboxylate | 3 | d | (400 MHz, DMSO-d$_6$) δ: 1.13 (t, J = 6.9, 3H), 1.26-2.05 (m, 19H), 2.25-2.44 (m, 3H), 2.53-2.65 (m, 2H), 2.96 (t, J = 6.4, 2H), 3.10-3.23 (m, 2H), 3.35-3.48 (m, 2H), 3.95-4.02 (m, 2H), 8.05 (br. s, 1H) | B | m/z 398 (M + H)$^+$ (ES$^+$), at 4.19 min, UV inactive |
| 54 | ethyl 4-(4-fluoro-4-(2-cyclopropylpropan-2-yl)carbamoyl)piperidin-1-yl)azepane-1-carboxylate | 3 | d | (400 MHz, DMSO-d$_6$) δ: 0.22-0.30 (m, 4H), 1.08-1.17 (m, 9H), 1.25-2.05 (m, 11H), 2.25-2.43 (m, 3H), 2.53-2.65 (m, 2H), 3.10-3.23 (m, 2H), 3.42-3.50 (m, 2H), 3.99 (q, J = 6.8, 2H), 6.83 (d, J = 2.3, 1H) | B | m/z 398 (M + H)$^+$ (ES$^+$), at 4.36 min, UV inactive |
| 55 | ethyl 4-(4-fluoro-4-(((cyclobutyl)carbamoyl)piperidin-1-yl)azepane-1-carboxylate | 3 | d | (400 MHz, DMSO-d$_6$) δ: 1.13 (td, J = 7.1, 1.7, 3H), 1.25-2.10 (m, 13H), 2.30-2.44 (m, 3H), 2.53-2.65 (m, 2H), 3.10-3.24 (m, 2H), 3.32-3.45 (m, 4H), 3.52-3.60 (m, 2H), 3.99 (qd, J = 6.9, 1.9, 2H), 8.23 (br. s, 1H) | B | m/z 370 (M + H)$^+$ (ES$^+$), at 3.36 min, UV inactive |
| 56 | ethyl 4-(4-methyl-4-(2-methylpropyl)carbamoyl)piperidin-1-yl)azepane-1-carboxylate | 4 | b | (400 MHz, DMSO-d$_6$) δ: 0.80-0.90 (m, 6H), 1.14-1.28 (m, 8H), 1.46-1.61 (m, 3H), 1.65-2.10 (m, 7H), 2.25-2.35 (m, 2H), 2.86-2.94 (m, 3H), 3.06-3.11 (m, 1H), 3.15-3.29 (m, 2H), 3.40-3.58 (m, 2H), 4.00-4.08 (m, 2H), 7.89 (t, J = 5.6, 1H) | B | m/z 368 (M + H)$^+$ (ES$^+$), at 3.23 min, UV inactive |
| 57 | prop-2-yn-1-yl-4-(4-((2-methylpropyl)carbamoyl)piperidin-1-yl)azepane-1-carboxylate | 5 | e | (400 MHz, DMSO-d$_6$) δ: 0.81 (d, J = 6.8, 6H), 1.35-1.92 (m, 14H), 2.32-2.45 (m, 1H), 2.65-2.78 (m, 2H), 2.85 (t, J = 6.2, 2H), 3.17-3.29 (m, 2H), 3.40-3.52 (m, 3H), 4.67 (t, J = 2.5, 2H), 7.70 (br. s, 1H) | B | m/z 364 (M + H)$^+$ (ES$^+$), at 3.20 min, UV inactive |
| 58 | but-2-yn-1-yl-4-(4-((2-methylpropyl)carbamoyl)piperidin-1-yl)azepane-1-carboxylate | 5 | e | (400 MHz, DMSO-d$_6$) δ: 0.81 (d, J = 6.8, 6H), 1.33-1.89 (m, 13H), 1.97-2.20 (m, 4H), 2.32-2.45 (m, 1H), 2.65-2.78 (m, 2H), 2.84 (t, J = 6.3, 2H), 3.14-3.29 (m, 2H), 3.38-3.50 (m, 2H), 4.61-4.64 (m, 2H), 7.68 (br. s, 1H) | B | m/z 378 (M + H)$^+$ (ES$^+$), at 3.39 min, UV inactive |
| 59 | 2-fluoroethyl-4-(4-((2-methylpropyl)carbamoyl)piperidin-1-yl)azepane-1-carboxylate | 5 | e | (400 MHz, CDCl$_3$) δ: 0.91 (d, J = 6.8, 6H), 1.40-2.70 (m, 15H), 2.80-2.98 (m, 2H), 3.08 (t, J = 6.4, 2H), 3.22-3.40 (m, 2H), 3.46-3.70 (m, 2H), 4.25-4.32 (m, 1H), 4.34-4.39 (m, 1H), 4.50-4.55 (m, 1H), 4.62-4.67 (m, 1H), 5.58 (br. s, 1H) | B | m/z 372 (M + H)$^+$ (ES$^+$), at 2.95 min, UV inactive |
| 60 | 2-methoxyethyl-4-(4-((2-methylpropyl)carbamoyl)piperidin-1-yl)azepane-1-carboxylate | 5 | e | (400 MHz, CDCl$_3$) δ: 0.90 (d, J = 6.8, 6H), 1.25-2.68 (m, 16H), 2.85-2.98 (m, 1H), 3.07 (t, J = 6.4, 2H), 3.22-3.35 (m, 2H), 3.38 (s, 3H), 3.47-3.68 (m, 4H), 4.20-4.27 (m, 2H), 5.60 (br. s, 1H) | B | m/z 384 (M + H)$^+$ (ES$^+$), at 2.81 min, UV inactive |
| 61 | 2-propyl-4-(4-((2-methylpropyl)carbamoyl)piperidin-1-yl)azepane-1-carboxylate | 5 | e | (400 MHz, DMSO-d$_6$) δ: 0.81 (d, J = 6.5, 6H), 0.89 (td, J = 7.3, 2.9, 3H), 1.30-1.91 (m, 12H), 2.00-2.25 (m, 2H), 2.35-2.45 (m, 2H), 2.70-2.80 (m, 2H), 2.84 (t, J = 6.2, 2H), 3.15-3.55 (m, 5H), 3.94 (td, J = 6.5, 2.7, 2H), 7.70 (br. s, 1H) | B | m/z 368 (M + H)$^+$ (ES$^+$), at 3.49 min, UV inactive |
| 62 | 2,2,2-trifluoroethyl-4-(4-((2-methylpropyl)carbamoyl)piperidin-1-yl)azepane-1-carboxylate | 5 | e | (400 MHz, DMSO-d$_6$) δ: 0.82 (d, J = 6.8, 6H), 1.30-2.45 (m, 16H), 2.68-2.79 (m, 1H), 2.85 (t, J = 5.8, 2H), 3.20-3.29 (m, 2H), 3.43-3.54 (m, 2H), 4.71 (qd, J = 9.0, 3.0, 2H), 7.70 (br. s, 1H) | B | m/z 408 (M + H)$^+$ (ES$^+$), at 3.55 min, UV inactive |
| 63 | ethyl (4S)-4-[4-((2-methylpropyl)methylcarbamoyl)piperidin-1-yl]azepane-1-carboxylate | 6-(S) | f | (400 MHz, DMSO-d$_6$) δ: 0.78 (d, J = 6.5, 6H), 1.14 (td, J = 7.0, 2.7, 3H), 1.25-2.00 (m, 14H), 2.05-2.25 (m, 3H), 2.81 (t, J = 6.2, 2H), 3.10-3.29 (m, 2H), 3.40-3.50 (m, 2H), 4.00 (q, J = 6.9, 2H), 7.71 (br. s, 1H) | B | m/z 354 (M + H)$^+$ (ES$^+$), at 3.10 min, UV inactive |

TABLE 2-continued

| Ex. No. | Name | Intermediate | Synthetic method | $^1$H NMR | LCMS Method | LCMS data |
|---|---|---|---|---|---|---|
| 64 | ethyl (4R)-4-{4-[(2-methylpropyl)methylcarbamoyl]piperidin-1-yl}azepane-1-carboxylate | 6-(R) | f | (400 MHz, DMSO-d$_6$) δ: 0.78 (d, J = 6.5, 6H), 1.12-1.18 (m, 3H), 1.32-2.00 (m, 14H), 2.05-2.30 (m, 3H), 2.83 (t, J = 6.2, 2H), 3.02-3.29 (m, 2H), 3.40-3.50 (m, 2H), 4.00 (q, J = 6.9, 2H), 7.87 (br. s, 1H) | B | m/z 354 (M + H)$^+$ (ES$^+$), at 3.30 min, UV inactive |
| 65 | ethyl (4S)-4-{4-[(1-methylcyclobutyl)carbamoyl]piperidin-1-yl}azepane-1-carboxylate | 6-(S) | f | (400 MHz, DMSO-d$_6$) δ: 1.13 (td, J = 7.1, 2.3, 3H), 1.28 (s, 3H), 1.29-1.60 (m, 7H), 1.60-1.87 (m, 7H), 1.90-1.99 (m, 1H), 2.02-2.24 (m, 4H), 2.32-2.40 (m, 1H), 2.65-2.73 (m, 2H), 3.06-3.22 (m, 2H), 3.35-3.48 (m, 2H), 3.98 (qd, J = 7.0, 2.7, 2H), 7.68 (br. s, 1H) | B | m/z 366 (M + H)$^+$ (ES$^+$), at 3.28 min, UV inactive |
| 66 | ethyl (4R)-4-{4-[(1-methylcyclobutyl)carbamoyl]piperidin-1-yl}azepane-1-carboxylate | 6-(R) | f | (400 MHz, DMSO-d$_6$) δ: 1.13 (td, J = 6.9, 1.8, 3H), 1.28 (s, 3H), 1.30-1.59 (m, 7H), 1.61-1.85 (m, 7H), 1.85-1.98 (m, 1H), 1.98-2.21 (m, 4H), 2.30-2.40 (m, 1H), 2.60-2.69 (m, 2H), 3.07-3.23 (m, 2H), 3.33-3.48 (m, 2H), 3.98 (qd, J = 7.0, 2.7, 2H), 7.65 (br. s, 1H) | B | m/z 366 (M + H)$^+$ (ES$^+$), at 3.2 min, UV inactive |
| 67 | ethyl (4S)-4-[4-(tert-butylcarbamoyl)piperidin-1-yl]azepane-1-carboxylate | 6-(S) | f | (400 MHz, DMSO-d$_6$) δ: 1.11-1.19 (m, 3H), 1.21 (s, 9H), 1.27-1.51 (m, 4H), 1.54 (m, 2H), 1.65-1.80 (m, 3H), 1.95-2.12 (m, 3H), 2.33-2.40 (m, 1H), 2.65-2.74 (m, 2H), 3.12-3.26 (m, 2H), 3.37-3.50 (m, 2H), 4.02 (qd, J = 6.9, 2.5, 2H), 7.23 (br. s, 1H) | B | m/z 354 (M + H)$^+$ (ES$^+$), at 3.17 min, UV inactive |
| 68 | ethyl (4R)-4-[4-(tert-butylcarbamoyl)piperidin-1-yl]azepane-1-carboxylate | 6-(R) | f | (400 MHz, DMSO-d$_6$) δ: 1.11-1.20 (m, 3H), 1.22 (s, 9H), 1.27-1.52 (m, 4H), 1.52-1.63 (m, 2H), 1.67-1.90 (m, 3H), 1.93-2.15 (m, 3H), 2.35-2.41 (m, 1H), 2.65-2.74 (m, 2H), 3.11-3.28 (m, 2H), 3.37-3.50 (m, 2H), 4.03 (qd, J = 7.0, 2.5, 2H), 7.23 (br. s, 1H) | B | m/z 354 (M + H)$^+$ (ES$^+$), at 3.17 min, UV inactive |
| 69 | ethyl 4-(4-{[(1-methylcyclobutyl)methyl]carbamoyl}piperidin-1-yl)azepane-1-carboxylate | 2 | c | (400 MHz, DMSO-d$_6$) δ: 1.01 (s, 3H), 1.17 (td, J = 7.0, 2.4, 3H), 1.30-1.45 (m, 2H), 1.48-1.66 (m, 7H), 1.68-1.85 (m, 7H), 2.07-2.18 (m, 2H), 2.31-2.41 (m, 2H), 2.61-2.88 (m, 2H), 3.02 (d, J = 6.3, 2H), 3.12-3.27 (m, 2H), 3.40-3.45 (m, 2H), 4.02 (qd, J = 7.0, 2.9, 2H), 7.71 (br. s, 1H) | B | m/z 380 (M + H)$^+$ (ES$^+$), at 3.63 min, UV inactive |
| 70 | ethyl 4-(4-{[1-(trifluoromethyl)cyclobutyl]carbamoyl}piperidin-1-yl)azepane-1-carboxylate | 2 | b | (300 MHz, DMSO-d$_6$) δ: 1.12 (t, J = 7.0, 3H), 1.22-1.52 (m, 4H), 1.52-1.60 (m, 2H), 1.64-1.94 (m, 5H), 1.94-2.18 (m, 3H), 2.25-2.43 (m, 4H), 2.52-2.87 (m, 4H), 3.07-3.24 (m, 2H), 3.33-3.49 (m, 2H), 3.99 (q, J = 7.0, 2H), 8.16 (br. s, 1H) | B | m/z 420 (M + H)$^+$ (ES$^+$), at 5.46 min, UV inactive |
| 71 | ethyl 4-{4-[(2-methylcyclopentyl)carbamoyl]piperidin-1-yl}azepane-1-carboxylate | 2 | b | (300 MHz, DMSO-d$_6$) δ: 0.71 (d, J = 6.9, 1H), 0.81-0.88 (m, 2H), 0.98-1.18 (m, 3H), 1.19-1.48 (m, 5H), 1.48-1.85 (m, 11H), 1.86-1.99 (m, 1H), 2.01-2.23 (m, 3H), 2.30-2.38 (m, 1H), 2.59-2.86 (m, 3H), 3.08-3.25 (m, 2H), 3.35-3.56 (m, 2H), 3.92-4.04 (m, 2H), 7.39-7.55 (m, 1H) | B | m/z 380 (M + H)$^+$ (ES$^+$), at 5.49 min, UV inactive |
| 72 | ethyl 4-{4-[(3-methylidenecyclobutyl)carbamoyl]piperidin-1-yl}azepane-1-carboxylate | 2 | b | (400 MHz, DMSO-d$_6$) δ: 1.13-1.21 (m, 3H), 1.21-1.31 (m, 4H), 1.41-1.65 (m, 2H), 2.07-1.65 (m, 7H), 2.05-2.20 (m, 1H), 2.25-2.42 (m, 1H), 2.57-2.72 (m, 1H), 2.82-2.95 (m, 2H), 2.97-3.05 (m, 1H), 3.09-3.19 (m, 1H), 3.19-3.30 (m, 2H), 3.46-3.72 (m, 2H), 4.05 (q, J = 6.8, 2H), 4.11-4.21 (m, 1H), 4.82 (s, 2H), 8.22-8.44 (m, 1H) | B | m/z 364 (M + H)$^+$ (ES$^+$), at 3.14 min, UV inactive |
| 73 | ethyl 4-{4-[(3-methylcyclobutyl)carbamoyl]piperidin- | 2 | b | (400 MHz, DMSO-d$_6$) δ: 1.01 (d, J = 7.0, 2H), 1.09 (d, J = 7.0, 1H), 1.13-1.23 (m, 3H), 1.35-1.65 (m, 9H), | B | m/z 366 (M + H)$^+$ (ES$^+$), at 3.37 min, |

TABLE 2-continued

| Ex. No. | Name | Intermediate | Synthetic method | ¹H NMR | LCMS Method | LCMS data |
|---|---|---|---|---|---|---|
|  | 1-yl}azepane-1-carboxylate |  |  | 1.72-1.87 (m, 4H), 1.89-2.05 (m, 2H), 2.09-2.37 (m, 4H), 2.70-2.79 (m, 2H), 3.07-3.27 (m, 2H), 3.41-3.47 (m, 2H), 3.94-4.12 (m, 2.5H), 4.26-4.31 (m, 0.5H), 7.88-7.96 (m, 1H) |  | UV inactive |
| 74 | ethyl 4-{4-[(1-ethylcyclobutyl)carbamoyl]piperidin-1-yl}azepane-1-carboxylate | 2 | b | (400 MHz, DMSO-d₆) δ: 0.71 (t, J = 7.3, 3H), 1.17 (td, J = 7.0, 2.8, 3H), 1.32-1.49 (m, 3H), 1.50-1.83 (m, 11H), 1.84-1.92 (m, 3H), 1.96-2.25 (m, 5H), 2.69-2.79 (m, 2H), 3.15-3.27 (m, 2H), 3.39-3.56 (m, 2H), 4.02 (qd, J = 7.0, 2.6, 2H), 7.65 (br. s, 1H) | B | m/z 380 (M + H)⁺ (ES⁺), at 3.54 min, UV inactive |
| 75 | ethyl 4-(4-{[2-(²H₃)methyl(²H₆)propyl]carbamoyl}piperidin-1-yl)azepane-1-carboxylate | 2 | b | (400 MHz, DMSO-d₆) δ: 1.11-1.16 (m, 3H), 1.23-1.55 (m, 7H), 1.65-1.80 (m, 3H), 1.92-2.22 (m, 3H), 2.23-2.41 (m, 1H), 2.65-2.75 (m, 2H), 3.07-3.23 (m, 2H), 3.36-3.42 (m, 2H), 3.96-4.00 (m, 2H), 7.63 (br. s, 1H) | B | m/z 363 (M + H)⁺ (ES⁺), at 3.08 min, UV inactive |
| 76 | ethyl 4-{4-[(1-fluoro-2-methylpropan-2-yl)carbamoyl]piperidin-1-yl}azepane-1-carboxylate | 2 | b | (400 MHz, DMSO-d₆) δ: 1.11-1.17 (m, 9H), 1.25-1.49 (m, 4H), 1.50-1.63 (m, 4H), 1.69-1.84 (m, 3H), 1.95-2.24 (m, 3H), 2.67-2.75 (m, 2H), 3.09-3.23 (m, 2H), 3.34-3.55 (m, 2H), 3.98 (qd, J = 6.9, 2.5, 2H), 4.38 (d, J = 48, 2H), 7.41 (br. s, 1H) | B | m/z 372 (M + H)⁺ (ES⁺), at 3.07 min, UV inactive |
| 77 | ethyl 4-{4-[(2-methylpentan-2-yl)carbamoyl]piperidin-1-yl}azepane-1-carboxylate | 2 | b | (400 MHz, DMSO-d₆) δ: 0.79 (t, J = 7.3, 3H), 1.09-1.20 (m, 11H), 1.28-1.63 (m, 9H), 1.65-1.85 (m, 4H), 1.91-2.18 (m, 3H), 2.64-2.74 (m, 2H), 3.13-3.22 (m, 2H), 3.34-3.48 (m, 2H), 3.98 (qd, J = 6.9, 2.7, 2H), 7.10 (br. s, 1H) | B | m/z 382 (M + H)⁺ (ES⁺), at 3.97 min, UV inactive |
| 78 | ethyl 4-{4-methyl-4-[(1-methylcyclobutyl)carbamoyl]piperidin-1-yl}azepane-1-carboxylate | 4 | b | (400 MHz, DMSO-d₆) δ: 0.97-1.25 (m, 8H), 1.29-1.38 (m, 3H), 1.40-1.60 (m, 3H), 1.62-1.75 (m, 3H), 1.77-1.96 (m, 4H), 1.99-2.07 (m, 1H), 2.09-2.33 (m, 4H), 2.69-2.89 (m, 2H), 3.07-3.20 (m, 4H), 3.40-3.56 (m, 2H), 3.82-4.12 (m, 2H), 7.21-7.56 (m, 1H) | B | m/z 380 (M + H)⁺ (ES⁺), at 3.40 min, UV inactive |
| 79 | ethyl 4-{4-methoxy-4-[(1-methylcyclobutyl)carbamoyl]piperidin-1-yl}azepane-1-carboxylate | 7 | e | (400 MHz, DMSO-d₆) δ: 1.17 (td, J = 7.1, 2.1, 3H), 1.35 (s, 3H), 1.36-1.50 (m, 2H), 1.50-1.64 (m, 1H), 1.64-1.94 (m, 11H), 2.09-2.27 (m, 2H), 2.24-2.40 (m, 4H), 3.07 (s, 3H), 3.12-3.28 (m, 2H), 3.28-3.55 (m, 3H), 4.02 (qd, J = 7.0, 2.3, 2H), 7.70 (br. s, 1H) | B | m/z 396 (M + H)⁺ (ES⁺), at 3.48 min, UV inactive |
| 80 | but-2-yn-1-yl 4-{4-methoxy-4-[(1-methylcyclobutyl)carbamoyl]piperidin-1-yl}azepane-1-carboxylate | 7 | e | (400 MHz, DMSO-d₆) δ: 1.35 (s, 3H), 1.37-1.53 (m, 2H), 1.54-1.64 (m, 1H), 1.66-1.84 (m, 12H), 1.85-1.92 (m, 3H), 2.13-2.26 (m, 2H), 2.30-2.42 (m, 4H), 3.08 (s, 3H), 3.14-3.28 (m, 2H), 3.40-3.63 (m, 2H), 4.63 (s, 2H), 7.66 (br. s, 1H) | B | m/z 420 (M + H)⁺ (ES⁺), at 3.90 min, UV inactive |
| 81 | ethyl 4-(4-methoxy-4-{[(1-methylcyclobutyl)methyl]carbamoyl}piperidin-1-yl)azepane-1-carboxylate | 8 | b | (400 MHz, DMSO-d₆) δ: 1.04 (s, 3H), 1.10-1.23 (m, 3H), 1.32-1.46 (m, 2H), 1.48-1.64 (m, 4H), 1.64-1.94 (m, 11H), 2.28-2.43 (m, 4H), 3.07 (d, J = 6.3, 2H), 3.10 (s, 3H), 3.14-3.27 (m, 2H), 3.38-3.49 (m, 2H), 3.91-4.07 (m, 2H), 7.68-7.86 (m, 1H) | B | m/z 410 (M + H)⁺ (ES⁺), at 4.22 min, UV inactive |
| 82 | ethyl 4-{4-cyano-4-[(1-methylcyclobutyl)carbamoyl]piperidin-1-yl}azepane-1-carboxylate | 9 | b | (400 MHz, DMSO-d₆) δ: 1.09-1.15 (m, 2H), 1.20-1.25 (m, 3H), 1.32 (s, 3H), 1.36-1.47 (m, 2H), 1.48-1.61 (m, 1H), 1.67-1.90 (m, 7H), 1.93-1.99 (m, 1H), 2.08-2.22 (m, 2H), 2.29-2.45 (m, 3H), 2.56-2.83 (m, 2H), 3.07-3.24 (m, 2H), 3.36-3.43 (m, 2H), 3.53-3.61 (m, 1H), 3.94-4.02 (m, 2H), 8.13 (br. s, 1H) | B | m/z 391 (M + H)⁺ (ES⁺), at 3.54 min, UV inactive |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen*, 2008). ERK1/2 phosphorylation is a downstream consequence of both Gq/11 and Gi/o protein coupled receptor activation, making it highly suitable for the assessment of M1, M3 (Gq/11 coupled) and M2, M4 receptors (Gi/o coupled), rather than using different assay formats for different receptor subtypes. CHO cells stably expressing the human muscarinic M1, M2, M3 or M4 receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader.

$pEC_{50}$ and $E_{max}$ figures were calculated from the resulting data for each receptor subtype.

The results are set out in Table 3 below.

TABLE 3

| | Muscarinic Activity | | | |
|---|---|---|---|---|
| Ex. No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| ACh | 8.31 (103) | 7.81 (104) | 8.16 (112) | 8.08 (110) |
| 3 | 6.70 (116) | <4.7 (6) | <4.7 (4) | 6.25 (85) |
| 6 | 7.07 (113) | <4.7 (10) | <4.7 (33) | 5.98 (76) |
| 7 | 7.09 (111) | <4.7 (2) | <4.7 (14) | 6.72 (80) |
| 8 | 6.82 (93) | <4.7 (3) | <4.7 (2) | 5.78 (55) |
| 9 | 6.93 (125) | <4.7 (6) | 4.88 (23) | 6.10 (41) |
| 11 | 7.22 (117) | <4.7 (7) | <4.7 (11) | 6.37 (67) |
| 15 | 6.95 (107) | <4.7 (5) | <4.7 (12) | 6.26 (67) |
| 17 | 7.21 (104) | <4.7 (0) | <4.7 (5) | 6.14 (46) |
| 18 | 7.08 (101) | <4.7 (7) | <4.7 (4) | 6.23 (39) |
| 26 | 6.35 (95) | <4.7 (7) | <4.7 (0) | 6.51 (51) |
| 27 | 7.34 (117) | <4.7 (56) | <4.7 (5) | 6.37 (88) |
| 30 | 7.24 (132) | <4.7 (3) | <4.7 (33) | 6.65 (104) |
| 31 | 7.50 (122) | <4.7 (0) | <4.7 (13) | 6.91 (90) |
| 37 | 7.86 (87) | <4.7 (8) | <4.7 (10) | 6.72 (75) |
| 39 | 7.14 (96) | <4.7 (2) | <4.7 (8) | <4.7 (13) |
| 40 | 7.34 (106) | <4.7 (13) | <4.7 (9) | 6.07 (89) |
| 41 | 7.40 (97) | <4.7 (41) | <4.7 (12) | 6.59 (88) |
| 44 | 7.50 (104) | <4.7 (19) | <4.7 (5) | 6.38 (113) |
| 45 | 6.95 (101) | <4.7 (29) | <4.7 (1) | 5.92 (59) |
| 46 | 6.98 (90) | <4.7 (9) | <4.7 (1) | 5.97 (63) |
| 48 | 7.21 (88) | <4.7 (12) | <4.7 (12) | 6.27 (73) |
| 50 | 7.71 (102) | <4.7 (17) | <4.7 (2) | 6.22 (90) |
| 51 | 7.29 (107) | <4.7 (12) | <4.7 (6) | 6.15 (93) |
| 52 | 6.64 (95) | <4.7 (9) | <4.7 (5) | 6.30 (84) |
| 53 | 7.01 (122) | <4.7 (9) | <4.7 (17) | 6.01 (90) |
| 54 | 7.31 (124) | <4.7 (15) | <4.7 (6) | 6.64 (114) |
| 55 | 6.73 (75) | <4.7 (17) | <4.7 (0) | 5.87 (69) |
| 56 | 7.19 (108) | <4.7 (4) | <4.7 (8) | 5.87 (46) |
| 57 | 7.03 (93) | <4.7 (5) | <4.7 (8) | 6.38 (82) |
| 63 | 7.16 (107) | <4.7 (5) | <4.7 (5) | 6.19 (89) |
| 64 | 6.97 (104) | <4.7 (5) | <4.7 (9) | 5.49 (81) |
| 65 | 7.50 (104) | <4.7 (7) | <4.7 (11) | 6.65 (97) |
| 66 | 6.56 (94) | <4.7 (12) | <4.7 (0) | 5.61 (66) |
| 67 | 6.90 (114) | <4.7 (48) | <4.7 (4) | 6.30 (104) |
| 68 | 6.09 (94) | NT | NT | 5.43 (64) |
| 69 | 7.98 (120) | <4.7 (12) | <4.7 (14) | 6.62 (78) |
| 70 | 6.57 (107) | <4.7 (5) | <4.7 (3) | 6.10 (55) |
| 74 | 7.28 (132) | <4.7 (19) | <4.7 (4) | 6.55 (97) |
| 75 | 7.06 (102) | <4.7 (14) | <4.7 (13) | 6.10 (87) |

TABLE 3-continued

| | Muscarinic Activity | | | |
|---|---|---|---|---|
| Ex. No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| 78 | 7.37 (115) | <4.7 (5) | <4.7 (0) | 6.38 (51) |
| 79 | 7.01 (113) | <4.7 (7) | <4.7 (27) | 6.06 (27) |
| 80 | 7.43 (89) | <4.7 (15) | <4.7 (7) | 6.28 (71) |
| 81 | 6.85 (110) | <4.7 (0) | <4.7 (7) | <4.7 (9) |
| 82 | 7.26 (89) | <4.7 (16) | <4.7 (2) | 5.79 (81) |

NT—Not tested

Example B

Passive Avoidance

Studies were carried out as described previously by Foley et al., (2004) *Neuropsychopharmacology*. In the passive avoidance task scopolamine administration (1 mg/kg, i.p.) at 6 hours following training rendered animals amnesic of the paradigm. A dose range of 3, 10, and 30 mg/kg (po) free base, administered 90 minutes prior to the training period via oral gavage, was examined.

Example 27 was found to reverse scopolamine-induced amnesia of the paradigm in a dose-dependent manner, with an approximate $ED_{50}$ of ca. 10 mg/kg (po). The effect of 30 mg/kg was similar to that produced by the cholinesterase inhibitor donepezil (0.1 mg/kg, ip) which served as a positive control (FIG. 1).

Example 65 was found to reverse scopolamine-induced amnesia of the paradigm in a dose-dependent manner, with significant effects observed after acute administration of 10 and 30 mg/kg (p<0.05; Bonferroni post hoc test). The effect at 10 and 30 mg/kg was not significantly different to that produced by the cholinesterase inhibitor donepezil (0.1 mg/kg, i.p.), which served as a positive control (FIG. 2).

Example 65 was found to reverse scopolamine-induced amnesia in a dose-dependent manner, with significant effects observed after acute administration of 10 mg/kg (po) (p<0.05; Bonferroni post hoc test). The effect at 10 mg/kg was not significantly different to that produced by the cholinesterase inhibitor donepezil (0.1 mg/kg, i.p.), which served as a positive control. Combination of Example 65 and donepezil did not result in a loss of activity, rather the combination had an additive effect at each dose combination as analysed by Mann Whitney u-test (FIG. 3).

Example C

Irwin Profile

The method, which detects the principal effects of a test substance on behaviour and physiological function, follows that described by Irwin (1968) *Psychopharmacologia*. Cholinergic side effects are potentially visible in the behavioural readout of the Irwin assay, and an absence of these side effects can be taken as an indication that agonism of the M2 and M3 receptors is not significant in vivo.

Rats are administered the test substance or its vehicle, and are observed in simultaneous comparison with a control group. Behavioural modifications, physiological and neurotoxicity symptoms, rectal temperature and pupil diameter are recorded according to a standardized observation grid derived from that of Irwin. The grid contains the following items: death, convulsions, tremor, Straub tail, altered activity, jumping, abnormal gait (rolling, tiptoe), motor incoordination, altered abdominal muscle tone, loss of grasping, akinesia, catalepsy, loss of traction, loss of balance, forepaw treading, writhing, piloerection, stereotypies (sniffing, chewing, head movements), head-twitches, scratching, altered respiration, aggression, altered fear/startle, altered reactivity to touch, ptosis, exophthalmia, loss of righting reflex, loss of corneal reflex, analgesia, defecation/diarrhea, salivation, lacrimation, rectal temperature (hypothermia/hyperthermia) and pupil diameter (myosis/mydriasis). Observations were performed at 15, 30, 60, 120, 180 minutes and 24 hours after administration of Example 27. No effects on any parameter were observed at any time point at doses of 3, 10, 30 and 75 mg/kg (po) when compared to vehicle control.

Observations were performed 15, 30, 60, 120, and 180 minutes post administration of Example 65. No significant effects on any parameter were observed at these time points at doses of 5, 10, 20 and 40 mg/kg when compared to vehicle control.

Example D

Novel Object Recognition

The novel object recognition paradigm is based on the greater spontaneous exploration of a novel object, compared with a familiar object, shown by rodents (Ennaceur and Delacour, 1988). The paradigm is considered a model of working memory and does not involve primary reinforcement such as food reward or noxious stimulus, thus making it analogous to memory tests employed in human clinical trials. Male Wistar rats were assessed for cognitive ability in a test apparatus comprising an open-field arena placed in a sound-attenuated room under dimmed lighting. Images of the open-field were captured by digital camera, and viewed on a monitor in an adjoining room. Each rat was subjected to the procedure separately and care taken to remove any olfactory/taste cues by cleaning the arena and test objects with alcohol between trials and rats. All tests are video scored blind to treatment. Following a 10-minute habituation period, each rat was placed into the test arena in the presence of two identical objects (plastic shapes). Each rat was placed facing the same direction at the same position in the arena, and the time spent actively exploring the objects during a 5-minute training period (T1) was recorded. The rat is returned to its home cage between tests. After 24 hours, each rat was again placed in the test arena for 5 minutes (T2) in the presence of one of the familiar objects and a novel object, and the time spent exploring both objects again recorded. The presentation order and position of the objects (left/right) was randomized between rats to prevent bias from order or place preference. Doses of 3, 10 or 30 mg/kg of test compound were administered by oral gavage 90 minutes prior to training (n=8). Donepezil (0.1 mg/kg) and galanthamine (3 mg/kg) were administered via intraperitoneal injection 60 minutes prior to training. Vehicle-treated controls were employed for comparison.

Statistical analysis determined that treatment with 10 and 30 mg/kg for Example 65 and 3 mg/kg of the positive control galanthamine significantly improved novel object recognition memory when compared to vehicle-treated controls (p<0.05) (FIG. 4). Donepezil (0.1 mg/kg) was without effect on novel object recognition. During the 10 minute training period in the apparatus, animals were scored for exploratory behaviour. There was no difference as regards exploration for either object or between vehicle-treated controls and any drug treatment group.

Example E

CA1 Cell Firing

Rat hippocampal slices of 400 μm thickness were cut in chilled (<4° C.) artificial cerebrospinal fluid (aCSF, composition in mM: NaCl 127, KCl 1.6, $KH_2PO_4$ 1.24, $MgSO_4$ 1.3, $CaCl_2$ 2.4, $NaHCO_3$ 26 and D-glucose 10) using vibratome. Slices were maintained in oxygenated (95% $O_2$/5% $CO_2$) aCSF at room temperature for at least 1 hr prior to electrophysiological recording, after which they were transferred to an interface chamber and constantly perfused with warmed (30° C.) oxygenated aCSF at a flow rate of 1.5-3 ml·min-1. Schaffer collaterals were then stimulated (1-20 V, 0.1 ms pulse width, 0.033 Hz) with a concentric bipolar electrode to evoke field excitatory post synaptic potentials (fEPSPs) recorded from the stratum radiatum of the CA1 region. Experiments were performed to examine the effect of compound compared to 1 μM carbachol (CCh), on the amplitude of fEPSPs in the CA1 region of rat hippocampal slices. 1 μM CCh was initially applied until steady-state, followed by wash, before performing a five point cumulative concentration-response to compound. Each compound was tested on 6 slices and results averaged. Drug preparation; compound was dissolved in 100% DMSO at a stock concentration of 30 mM, and diluted according to requirements, carbamoylcholine chloride (CCh) was purchased from Sigma (Cat#C4382) and dissolved at a stock concentration of 1 mM in dd$H_2O$.

TABLE 4

| Ex. No. | Cell Firing EC50 (mM) |
|---|---|
| 6 | 4.10E−06 ± 0.2 |
| 27 | 1.21E−06 ± 0.08 |
| 40 | 9.40E−06 ± 0.09 |
| 65 | 2.05E−06 ± 0.06 |

Example F

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and optionally 1% by weight of magnesium stearate and filling the resulting mixture into standard opaque hard gelatin capsules.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of treating a cognitive disorder, comprising administering an effective amount of the compound having the formula:

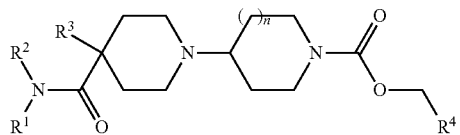

or a salt thereof, wherein:
n is 1 or 2;
$R^1$ is a $C_{1-10}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
$R^2$ is hydrogen or a $C_{1-10}$ non-aromatic hydrocarbon group;
or $R^1$ and $R^2$ together with the nitrogen atom to which they are attached form a non-aromatic heterocyclic group of four to nine ring members, wherein the heterocyclic ring may optionally contain a second heteroatom selected from O, N and S and oxidised forms thereof; and wherein the heterocyclic ring may optionally be substituted with one to six more substituents selected from $C_{1-2}$ alkyl; fluorine; and cyano;
$R^3$ is selected from hydrogen; halogen; cyano; hydroxy; $C_{1-3}$ alkoxy; and a $C_{1-5}$ non-aromatic hydrocarbon group which is optionally substituted with one to six fluorine atoms and wherein one or two, but not all, carbon atoms of the hydrocarbon group may optionally be replaced by a heteroatom selected from O, N and S; and
$R^4$ is a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof.

2. The method of claim 1, wherein $R^1$ is selected from:
$C_{1-6}$ alkyl optionally substituted with 1 to 6 fluorine atoms;
methoxy-$C_{1-4}$ alkyl optionally substituted with 1 to 6 fluorine atoms;
$C_{1-6}$ alkoxy;
$C_{2-6}$ alkenyl;
$C_{2-6}$ alkynyl;
$C_{3-6}$ cycloalkyl optionally substituted with one or two methyl groups;
$C_{4-5}$ cycloalkyl-$CH_2$— wherein the $C_{4-5}$ cycloalkyl moiety is optionally substituted with one $C_{1-2}$ alkyl group and wherein one carbon atom of the $C_{4-5}$ cycloalkyl moiety may optionally be replaced by an oxygen atom;
cyclopropyl-$C_{1-3}$ alkyl;
cyclopentenyl;
adamantyl; and
methyl-bicyclo[2.2.2]octanyl.

3. The method of claim 2, wherein $R^1$ is selected from 2-methylpropyl, tert-butyl, 2-methylbutyl, 2,2-dimethylpropyl, 2-methylbut-2-yl, cyclobutylmethyl, cyclopropylmethyl, cyclopentylmethyl, isopropyl, 1-methylcyclohexyl, 1-methylcyclopentylmethyl, 2-cyclopropylpropyl, 1-methylcyclobutyl, cyclopentyl, 2,3-dimethylbutan-2-yl, 1-ethylcyclobutylmethyl, 1-methylcyclopentyl, 2-cyclopropylpropan-2-yl, cyclobutyl, 1-methylcyclobutylmethyl, 1-(trifluoromethyl)cyclobutyl, 1-ethylcyclobutyl, ($^2H_3$)methyl($^2H_6$)propyl and 2-methylpentan-2-yl.

4. The method of claim 3, wherein $R^2$ is selected from hydrogen, methyl, ethyl and isopropyl.

5. The method of claim 4, wherein $R^3$ is selected from hydrogen, fluorine, cyano, methoxy and methyl.

6. The method of claim 5, wherein $R^4$ is selected from methyl, ethyl, ethynyl and 1-propynyl.

7. The method of claim 6, wherein n is 1.

8. The method of claim 6, wherein n is 2.

9. The method of claim 1, wherein the compound is represented by the following formula:

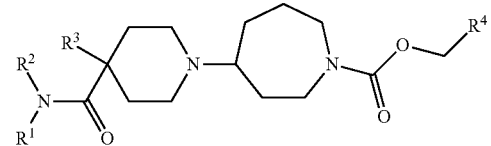

or a salt thereof, wherein:
$R^1$ is selected from 2-methylpropyl, tert-butyl, 2-methylbutyl, 2,2-dimethylpropyl, 2-methylbut-2-yl, cyclobutylmethyl, cyclopropylmethyl, cyclopentylmethyl, isopropyl, 1-methylcyclohexyl, 1-methylcyclopentylmethyl, 2-cyclopropylpropyl, 1-methylcyclobutyl, cyclopentyl, 2,3-dimethylbutan-2-yl, 1-ethylcyclobutylmethyl, 1-methylcyclopentyl, 2-cyclopropylpropan-2-yl, cyclobutyl, 1-methylcyclobutylmethyl, 1-(trifluoromethyl)cyclobutyl, 1-ethylcyclobutyl, ($^2H_3$)methyl($^2H_6$)propyl and 2-methylpentan-2-yl;
$R^2$ is selected from hydrogen, methyl, ethyl and isopropyl;
or $R^1$ and $R^2$ together with the nitrogen atom to which they are attached form a non-aromatic heterocyclic group of four to nine ring members, wherein the heterocyclic ring may optionally contain a second heteroatom selected from O, N and S and oxidised forms thereof; and wherein the heterocyclic ring may optionally be substituted with one to six more substituents selected from $C_{1-2}$ alkyl; fluorine; and cyano;
$R^3$ is selected from hydrogen; fluorine; cyano; methoxy and methyl; and
$R^4$ is selected from methyl, ethyl, ethynyl and 1-propynyl.

10. The method of claim 1, wherein the compound is represented by the following formula:

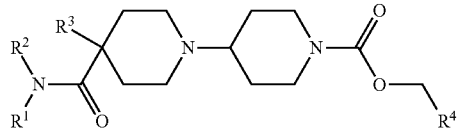

or a salt thereof, wherein:
$R^1$ is selected from 2-methylpropyl, tert-butyl, 2-methylbutyl, 2,2-dimethylpropyl, 2-methylbut-2-yl, cyclobutylmethyl, cyclopropylmethyl, cyclopentylmethyl, isopropyl, 1-methylcyclohexyl, 1-methylcyclopentylmethyl, 2-cyclopropylpropyl, 1-methylcyclobutyl, cyclopentyl, 2,3-dimethylbutan-2-yl, 1-ethylcyclobutylmethyl, 1-methylcyclopentyl, 2-cyclopropylpropan-2-yl, cyclobutyl, 1-methylcyclobutylmethyl, 1-(trifluoromethyl)cyclobutyl, 1-ethylcyclobutyl, ($^2H_3$)methyl($^2H_6$)propyl and 2-methylpentan-2-yl;

$R^2$ is selected from hydrogen, methyl, ethyl and isopropyl;

or $R^1$ and $R^2$ together with the nitrogen atom to which they are attached form a non-aromatic heterocyclic group of four to nine ring members, wherein the heterocyclic ring may optionally contain a second heteroatom selected from O, N and S and oxidised forms thereof; and wherein the heterocyclic ring may optionally be substituted with one to six more substituents selected from $C_{1-2}$ alkyl; fluorine; and cyano;

$R^3$ is selected from hydrogen; fluorine; cyano; methoxy and methyl; and $R^4$ is selected from methyl, ethyl, ethynyl and 1-propynyl.

\* \* \* \* \*